US011938227B2

United States Patent
Bao et al.

(10) Patent No.: US 11,938,227 B2
(45) Date of Patent: Mar. 26, 2024

(54) LIPID NANOPARTICLES ENCAPSULATION OF LARGE RNA

(71) Applicant: Arcturus Therapeutics, Inc., San Diego, CA (US)

(72) Inventors: Yanjie Bao, San Diego, CA (US); Brenda Clemente, San Diego, CA (US); Priya Prakash Karmali, San Diego, CA (US)

(73) Assignee: Arcturus Therapeutics, Inc., San Diego, CA (US)

( * ) Notice: Subject to any disclaimer, the term of this patent is extended or adjusted under 35 U.S.C. 154(b) by 307 days.

(21) Appl. No.: 17/473,063

(22) Filed: Sep. 13, 2021

(65) Prior Publication Data

US 2022/0168234 A1    Jun. 2, 2022

Related U.S. Application Data

(60) Provisional application No. 63/077,648, filed on Sep. 13, 2020.

(51) Int. Cl.
 *A61K 9/00* (2006.01)
 *A61K 9/51* (2006.01)
 (Continued)

(52) U.S. Cl.
 CPC ........ *A61K 9/5192* (2013.01); *A61K 31/7105* (2013.01)

(58) Field of Classification Search
 CPC ... A61K 9/00; A61K 9/50; A61K 9/51; A61K 9/519; A61K 9/5192; A61K 31/00; A61K 31/70; A61K 31/71; A61K 31/7105
 See application file for complete search history.

(56) References Cited

U.S. PATENT DOCUMENTS 8,956,572 B2    2/2015 Knopov et al.
9,592,555 B2    3/2017 Schut et al.
(Continued)

FOREIGN PATENT DOCUMENTS

WO    WO-01/05374      1/2001
WO    WO-2016/081029   5/2016
WO    WO-2018/119163   6/2018

OTHER PUBLICATIONS

International Search Report and Written Opinion received for PCT Application No. PCT/US2020/023442, dated Jun. 11, 2020 (6 pages).

*Primary Examiner* — Jacob T Minskey
*Assistant Examiner* — Matthew Hoover
(74) *Attorney, Agent, or Firm* — Mintz, Levin, Cohn, Ferris

(57) ABSTRACT

A method of producing lipid-encapsulated RNA nanoparticles includes flowing an aqueous solution comprising an RNA through a $1^{st}$ tube having a first inner diameter (ID); the RNA comprises from about 6,000 to about 13,000 nucleotides; flowing an ethanol solution comprising lipids through a $2^{nd}$ tube having a second inner diameter (ID), at a flow rate of about 0.2 to about 1 times relative to the aqueous solution through the $1^{st}$ tube, the lipids comprise a cationic lipid; and mixing the ethanol solution with the aqueous solution; the first ID and second ID and flow rates through the $1^{st}$ tube and $2^{nd}$ tube are selected to produce a shear force sufficiently low to preserve the integrity of the RNA; the mixing produces an output solution flowing in the $1^{st}$ tube comprising a turbulent flow of the RNA and the lipids in between about ethanol, the lipid-encapsulated RNA nanoparticles having a bilayer structure.

20 Claims, 4 Drawing Sheets

(51) Int. Cl.
*A61K 31/00* (2006.01)
*A61K 31/7105* (2006.01)

(56) References Cited

U.S. PATENT DOCUMENTS

| | | |
|---|---|---|
| 2004/0142025 A1 | 7/2004 | MacLachlan et al. |
| 2013/0037977 A1 | 2/2013 | Burke et al. |
| 2014/0248358 A1 | 9/2014 | Figueiredo et al. |
| 2016/0032320 A1* | 2/2016 | Yaworski ........... A61K 31/7088 514/44 A |
| 2016/0243255 A1* | 8/2016 | Nechev ................ B01F 35/92 |
| 2017/0152516 A1* | 6/2017 | Knopov .............. C12N 15/113 |

* cited by examiner

LIPID NANOPARTICLES ENCAPSULATION OF LARGE RNA

RELATED APPLICATION

This application is entitled to priority pursuant to 35 U.S.C. 119(e) to U.S. provisional patent application No. 63/077,648, filed on Sep. 13, 2020, which is herein incorporated in its entirety.

BACKGROUND

Lipids are used as materials for ribonucleic acid (RNA) delivery owing to their ability to form lipid nanoparticles that encapsulate RNA for delivery to target cells upon parenteral administration. (Zimmermann, 2006, Nature, doi: 10.1038/nature04688).

Different methods of producing lipid-encapsulated RNA nanoparticles are known. For example, WO 2001/005373 discloses techniques for preparing lipid-encapsulated RNA nanoparticles using an ethanol injection-type process with a static mixer that provides a turbulent environment, which after vesicle formation are combined with a therapeutic molecule. US 2004/0142025 discloses techniques for forming lipid-encapsulated RNA nanoparticles using non-turbulent mixing and a series of sequential stepwise dilutions. U.S. Pat. No. 6,843,942 discloses a non-turbulent mixing method of forming the particles by spraying lipids in an organic solution pipe through an orifice into nucleic acids in an aqueous solution flowing past the orifice. U.S. Pat. No. 9,005,654 discloses encapsulating siRNA in a lipid nanoparticle (LNP) using turbulent mixing, whereby lipids and RNA as opposing flows enter a T-shaped mixing chamber from opposite arms at about equal rates to produce a 45-60% ethanol solution comprising vesicles, which are collected and then further diluted (direct dilution method). U.S. Pat. No. 9,404,127 discloses that a majority of the LNPs produced by the direct dilution method have non-lamellar morphology, i.e., a non-bilayer structure.

Challenges arise in trying to apply conventional methods to form lipid-encapsulated RNA nanoparticles from large RNAs. For example, one such problem arises from the forces exerted on the RNA during LNP formation causing compromised structural integrity of the RNA. Accordingly, a need exists to improve the process and apparatus for formulating lipid-encapsulated RNA nanoparticles in the context of large RNA sequences. Such methods should also be amenable to scale up while targeting desired particle size and polydispersity. Embodiments herein address one or more of these issues and other challenges recognized by those skilled in the art.

SUMMARY

In some aspects, embodiments herein provide methods of producing a lipid-encapsulated RNA nanoparticle, comprising the steps a) flowing an aqueous solution comprising an RNA through a $1^{st}$ tube having an inner diameter (ID) of from about 0.01 inches to about 0.08 inches; wherein a pH of the aqueous solution is in a range from about 3.0 to about 4.5 with an optional NaCl concentration of up to about 300 mM; wherein the RNA comprises from about 6,000 to about 13,000 nucleotides; b) flowing an ethanol solution comprising lipids through a $2n^d$ tube having an ID of from about 0.01 inches to about 0.04 inches at a flow rate of about 0.2 to about 1 times a flow rate of the aqueous solution through the $1^{st}$ tube, wherein the lipids comprise a cationic lipid; and c) mixing the ethanol solution with the aqueous solution; wherein the mixing produces an output solution flowing in the $1^{st}$ tube comprising a turbulent flow of the RNA and the lipids in about 10% to 75% ethanol v/v; and wherein the lipid-encapsulated RNA nanoparticles have a bilayer structure.

In some aspects, embodiments herein provide methods of producing a lipid-encapsulated RNA nanoparticle, comprising the steps a) flowing an aqueous solution comprising an RNA through a $1^{st}$ tube having a first inner diameter (ID); wherein the RNA comprises from about 6,000 to about 13,000 nucleotides; b) flowing an ethanol solution comprising lipids through a $2^{nd}$ tube having a second inner diameter (ID), at a flow rate of about 0.2 to about 1 times a flow rate of the aqueous solution through the $1^{st}$ tube, wherein the lipids comprise a cationic lipid; and c) mixing the ethanol solution with the aqueous solution; wherein the first ID and second ID and flow rates through the $1^{st}$ tube and $2^{nd}$ tube are selected to produce a shear force sufficiently low to preserve the integrity of the RNA; wherein the mixing produces an output solution flowing in the $1^{st}$ tube comprising a turbulent flow of the RNA and the lipids in between about 10% to 75% ethanol v/v; and wherein the lipid-encapsulated RNA nanoparticles have a bilayer structure.

DETAILED DESCRIPTION

Figure 1:
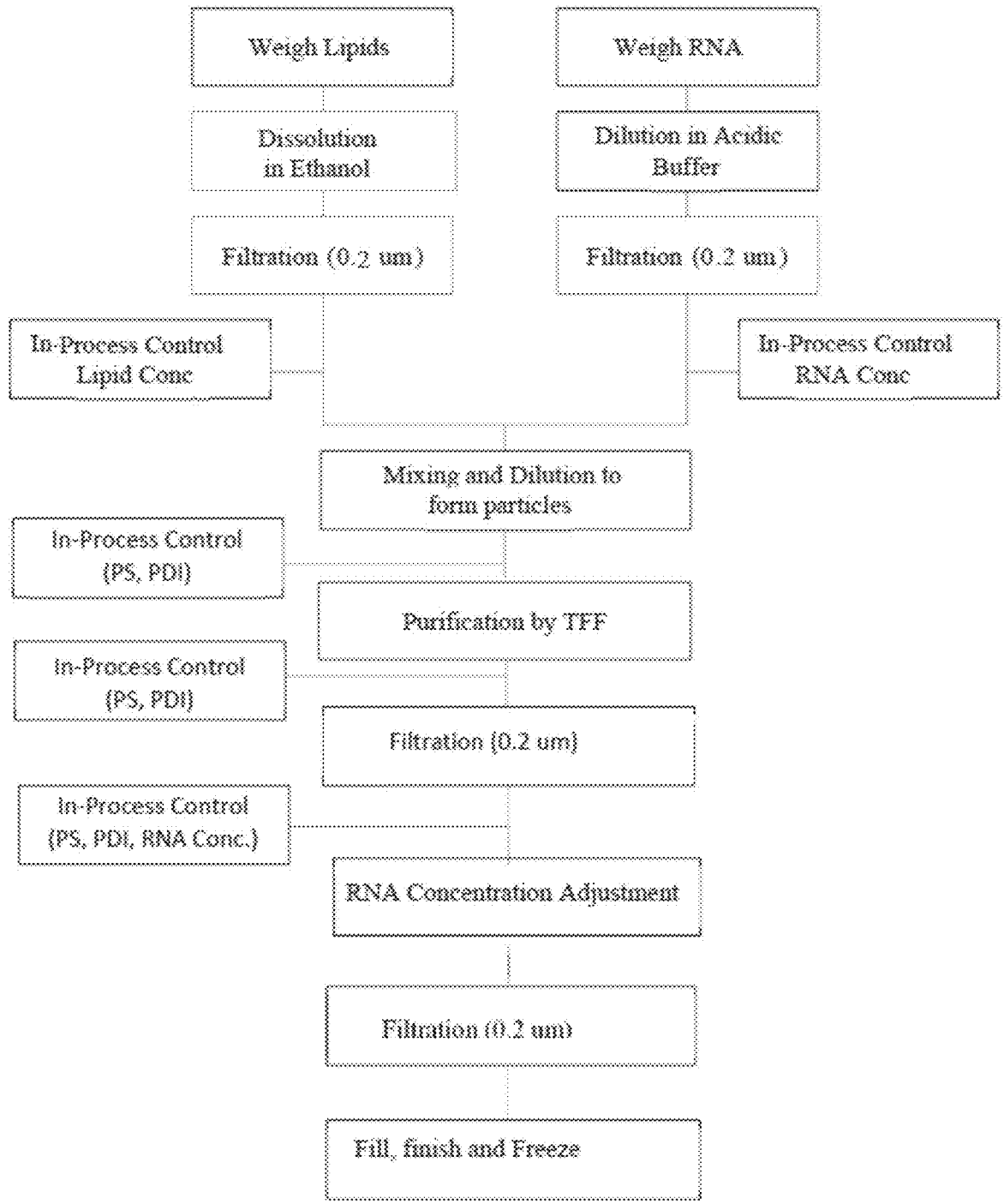
FIG. 1 shows a flow chart diagram for one embodiment of a process of producing lipid nanoparticles. Lipids are dissolved in ethanol, RNA is dissolved in an aqueous acidic buffer (e.g. citrate buffer), both are filter sterilized. The solutions are mixed by the process described herein to form particles, which are analyzed for PDI and particle size (PS). The particles are concentrated and purified by tangential flow filtration (TFF) to remove ethanol and unbound RNA, and PDI and PS is again monitored. The concentration of the particles is then adjusted according to measured total RNA concentration. The particles are filter sterilized, filled, finished, and frozen.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, figures and detailed description are to be regarded as illustrative in nature and not as restrictive.

Embodiments herein provide processes for encapsulating large RNAs (e.g. self-replicating RNA) in lipid nanoparticles. For example, large mRNAs may have sizes on the order 6,000 to about 15,000 nucleotides. As disclosed herein it was found that these large nucleotides were not compatible with typical LNP forming processes. An LNP process that is typically used for making mRNA-LNP compositions was used to try and make self replicating RNA encapsulated LNPs. The following procedure is typical for RNA containing about 1,000 to about 5,000 nucelotides. Bulk formulation is manufactured by mixing an ethanolic solution of lipids with an aqueous solution of RNA drug substance or other smaller mRNA as outlined below:

Lipid excipients (cationic lipid, phospholipid, cholesterol (Chol) and PEG-lipid conjugate are dissolved in ethanol and filtered through a 0.2 μm polyethersulfone (PES) filter.

An aqueous solution of mRNA is prepared in citrate pH 4.0 buffer followed by filtration through a 0.2 μm PES filter.

The mRNA solution is then mixed with the ethanolic solution of lipids via a stainless-steel mixing module. Nanoparticles thus formed are stabilized by sequential dilution with phosphate pH 6.0 buffer followed by HEPES pH 8.0 buffer.

Ultrafiltration and diafiltration (UF/DF) of the nanoparticle formulation is then performed by tangential flow filtration (TFF) using modified PES hollow-fiber membranes (100 kDa MWCO (molecular weight cutoff)) and HEPES pH 8.0 buffer. Post UF/DF, the formulation is filtered through a 0.2 μm PES filter and stored at 2 to 8° C. until fill.

An in-process mRNA concentration analysis is then performed. Concentration of the formulation is adjusted to the final target mRNA concentration (0.2 mg/mL) followed by filtration through a 0.2 μm PES sterilizing-grade filter.

Post sterile filtration, the bulk product is aseptically filled into glass vials, stoppered, capped, and frozen at −70±10° C.

Using this process, the resulting LNPs with larger RNAs (more than about 6,000 nucleotides) had poor size, dispersion, and encapsulation efficiency. Moreover, it was discovered that a substantial portion of these larger RNA structures were being degraded in the formulation process, which was hypothesized to be due to shear forces resulting from certain process pressures and flow rates used in this method. It was postulated that such shear forces could be modulated by altering flow rates and tube sizing. However, mixing conditions and operating pressure alone were not considered the only variables that would necessarily provide the requisite LNP-wrapped RNAs. By reducing shear forces and adjusting mixing conditions, it was possible that conditions might not be sufficient for LNP formation. Accordingly, the problem presented by large RNAs was considered complex as other parameters were considered to factor into the successful formation of LNP-wrapped large RNAs including, without limitation, buffer and salt concentrations, RNA and lipid concentrations, pH and overall back pressure in the system.

Embodiments herein provide a working solution to the formation of LNP-encapsulated large RNAs. Among the advantages of the methods disclosed herein, are (1) the large variability of composition that is tolerated with different lipid components, such as a range of phospholipid/helper lipid concentrations, cationic lipid concentrations and cholesterol, and RNA size; (2) the transferability between different scalable modules for manufacturing on small, medium, and large scales; and (3) the ability to scale up production while maintaining reduced batch volume.

In embodiments, there are provided methods of producing a lipid-encapsulated RNA nanoparticle, comprising the steps: a) flowing an aqueous solution comprising an RNA through a $1^{st}$ tube having an inner diameter (ID) of from about 0.01 inches to about 0.08 inches; wherein a pH of the aqueous solution is in a range from about 3.0 to about 4.5 with an optional NaCl concentration up to about 300 mM; wherein the RNA comprises from about 6,000 to about 13,000 nucleotides; b) flowing an ethanol solution comprising lipids through a $2^{nd}$ tube having an ID of from about 0.01 inches to about 0.04 inches at a flow rate of about 0.2 to about 1 times a flow rate the aqueous solution through the $1^{st}$ tube, wherein the lipids comprise a cationic lipid; and c) mixing the ethanol solution with the aqueous solution; wherein the mixing produces an output solution flowing in the $1^{st}$ tube comprising a turbulent flow of the RNA and the lipids in about 10% to 75% ethanol v/v; and wherein the lipid-encapsulated RNA nanoparticles have a bilayer structure.

In embodiments, there are provided methods of producing a lipid-encapsulated RNA nanoparticle, comprising the steps: a) flowing an aqueous solution comprising an RNA through a $1^{st}$ tube having a first inner diameter (ID); wherein the RNA comprises from about 6,000 to about 13,000 nucleotides; b) flowing an ethanol solution comprising lipids through a $2^{nd}$ tube having a second inner diameter (ID), at a flow rate of about 0.2 to about 1 times a flow rate the aqueous solution through the $1^{st}$ tube, wherein the lipids comprise a cationic lipid; and c) mixing the ethanol solution with the aqueous solution; wherein the first ID and second ID and flow rates through the $1^{st}$ tube and $2^{nd}$ tube are selected to produce a shear force sufficiently low to preserve the integrity of the RNA; wherein the mixing produces an output solution flowing in the $1^{st}$ tube comprising a turbulent flow of the RNA and the lipids in between about 10% to 75% ethanol v/v; and wherein the lipid-encapsulated RNA nanoparticles have a bilayer structure.

In embodiments, the mixing comprises flowing the ethanol solution and the aqueous solution into a mixing module consisting of the $2^{nd}$ tube perpendicularly joined to the $1^{st}$ tube.

In embodiments, the mixing comprises flowing the ethanol solution and the aqueous solution into a multi-inlet vortex mixer.

In embodiments, a concentration of RNA in the aqueous solution is in a range from about 85 micrograms/mL to about 2100 micrograms/mL. In embodiments, the range is from about 85 to about 200 micrograms/mL, or about 200 to about 500, or about 500 to about 800, or about 800 to about 1000, or about 1000 to about 1500, or about 1500 to about 2100 micrograms/mL, including any sub-ranges therebetween and fractions thereof.

In embodiments, a concentration of lipid in the ethanol solution is in a range from about 5.0 mg/mL to about 125 mg/mL. In embodiments, the range is from about 5.0 to about 30 mg/mL, or about 30 to about 60, or about 60 to about 90, or about 90 to about 125 mg/mL, including any sub-ranges therebetween and fractions thereof.

In embodiments, the aqueous solution is pumped through the $1^{st}$ tube by a $1^{st}$ pump with a back pressure of not more than about 200 psi, and the ethanol solution is pumped through the $2^{nd}$ tube by a $2^{nd}$ pump. In some embodiments the back pressures is not more than about 195 psi, or not more than about 190 psi, or not more than about 180 psi.

In embodiments, the $1^{st}$ tube has an ID in a range from about 0.01 inches to about 0.08 inches and the $2^{nd}$ tube has an ID in a range from about 0.01 inches to about 0.04 inches. In embodiments, the $1^{st}$ tube has an ID in a range from about 0.02 inches to about 0.03 inches and the $2^{nd}$ tube has an ID in a range from about 0.01 inches to about 0.02 inches. In embodiments, the $1^{st}$ tube has an ID of about 0.02 inches and the $2^{nd}$ tube has an ID of about 0.01 inches. In embodiments, the $1^{st}$ tube has an ID of about 0.03 inches and the $2^{nd}$ tube has an ID of about 0.01 inches. Such measurements include any sub-ranges therebetween and fractions thereof.

In embodiments, the aqueous solution is pumped at a flow rate in a range from about 40 mL/min. to about 375 mL/min. In embodiments, the flow rate is in a range from about 40 to about 80 mL/min., or about 80 to about 120, or about 120 to about 160, or about 160 to about 200, or about 200 to about 240, or about 240 to about 280, or about 280 to about 320, or about 320 to about 375 mL/min, including any sub-range therebetween and fractions thereof.

In embodiments, the ethanol solution is pumped at a flow rate in a range from about 10 mL/min. to about 75 mL/min. In some embodiments, the flow rate is in a range from about 10 to about 30 mL/min., or about 30 to about 50, or about 50 to about 75 mL/min., including any sub-ranges therebetween and fractions thereof.

In embodiments, the aqueous, ethanol, and output solutions are maintained in a temperature range from about 10° C. to about 25° C.

In embodiments, methods may further comprise pumping a first dilution buffer and mixing the dilution buffer with the output solution by introducing the dilution buffer to the output solution to produce a first diluted output solution.

In embodiments, methods may further comprise pumping a second dilution buffer into the first diluted output solution thereby forming a final diluted output solution, wherein there is a delay between pumping the first dilution buffer and second dilution buffer.

In embodiments, the delay is from about 0.1 to about 30 seconds, wherein the delay is created by a length of tubing. In some embodiments, there is no delay. In some embodiments, the delay is from 0.1 to about 5 seconds, or about 5 to about 10 seconds, or about 10 to about 15 seconds, or about 15 to about 20 seconds, or about 20 to about 30 seconds, including any sub-range therebetween and fractions thereof.

In embodiments, the first dilution buffer comprises: a buffering agent having a pH from about 5.5 to about 7.0; and optionally a sodium chloride concentration up to about 100 mM. For example, the first dilution buffer may comprise a Tris buffer up to about 20 mM, or a 40 mM to 90 mM phosphate buffer, or a 20 mM to 50 mM HEPES buffer, or a 45 mM pH 6.5 phosphate buffer.

In embodiments, the first dilution buffer may optionally comprise a sodium chloride concentration up to about 50 mM.

In embodiments, the second dilution buffer may comprise a buffering agent having a pH between about 7.4 and 8.0; and optionally a sodium chloride concentration up to about 100 mM.

In embodiments, the second dilution buffer may optionally comprise a sodium chlorides solution up to about 50 mM.

In embodiments, the second buffer comprises sucrose up to about 15% w/v. In some embodiments, sucrose is present up to about 12% w/v, or up to about 10% or up to about 8%, or up to about 5%, or up to about 1%. In some embodiment sucrose is absent.

In embodiments, the second buffer comprises an antioxidant up to about 0.5% w/v. In some embodiments, an antioxidant is absent. In some embodiments, the antioxidant is present up to about 0.4% w/v, or about 0.3%, or about 0.2%, or about 0.1% w/v.

In embodiments, the second buffer comprises up to 20 mM of a chelating agent.

In embodiments, the first diluted output solution comprises about 1.0% to about 10.0% ethanol. In some embodiments, the first diluted about comprises from about 2% to about 8% ethanol, or from about 3 to about 7% ethanol, including any sub-range therebetween and fractions thereof.

In embodiments, the first dilution buffer is pumped at a flow rate from about 80 mL/min. to about 900 mL/min. In some embodiments, the flow rate is from about 80 mL/min. to about 150 mL/min, or about 150 to about 200, or about 200 to about 250, or about 250 to about 300, or about 300 to about 400, or about 400 to about 500, or about 500 to about 600, or about 600 to about 700, or about 700 to about 900 mL/min., including any sub-range therebetween and fractions thereof.

In embodiments, the second dilution buffer is pumped at a flow rate from about 240 mL/min to about 5400 mL/min. In some embodiments, the flow rate is from about 240 to about 500 mL/min., or about 500 to about 1000, or about 1000 to about 1500, or about 1500 to about 2000, or about 2000 to about 2500, or about 2500 to about 3000, or about 3000 to about 3500, or about 3500 to about 4000, or about 4000 to about 4500, or about 4500 to about 5000, or about 5000 to about 5500 mL/min., including any sub-range therebetween and fractions thereof.

In embodiments, the output solution has a total flow rate in a range from about 120 mL/min to about 300 mL/min.

In embodiments, the cationic lipid has a structure of Formula I:

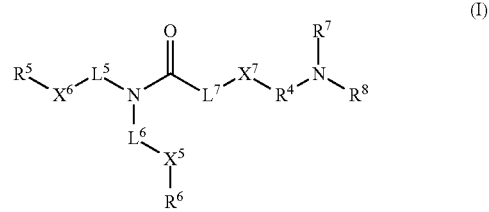

or a pharmaceutically acceptable salt or solvate thereof, wherein $R^5$ and $R^6$ are each independently selected from the group consisting of a linear or branched $C_1$-$C_{31}$ alkyl, $C_2$-$C_{31}$ alkenyl or $C_2$-$C_{31}$ alkynyl and cholesteryl;

$L^5$ and $L^6$ are each independently selected from the group consisting of a linear $C_1$-$C_{20}$ alkyl and $C_2$-$C_{20}$ alkenyl;

$X^5$ is —C(O)O— or —OC(O)—;

$X^6$ is —C(O)O— or —OC(O)—;

$X^7$ is S or O;

$L^7$ is absent or lower alkyl;

$R^4$ is a linear or branched $C_1$-$C_6$ alkyl; and $R^7$ and $R^8$ are each independently selected from the group consisting of a hydrogen and a linear or branched $C_1$-$C_6$ alkyl.

In embodiments, the lipid-encapsulated RNA nanoparticle has an average particle size in a range from about 50 nm to about 120 nm. In some embodiments the average particle size is form about 60 to about 120 nm, about 70 to about 120 nm, or about 70 to about 90 nm, including any sub-range therebetwen and fractions thereof.

In embodiments, the polydispersity lipid encapsulated RNA nanoparticles does not exceed about 0.2.

In embodiments, the lipid portion of the lipid-encapsulated RNA nanoparticle further comprises one or more agents selected from the group consisting of a helper lipid, a cholesterol, and a PEG lipid conjugate.

In embodiments, the RNA is self-replicating RNA.

In embodiments, methods may further comprise lyophilizing the final diluted output solution.

The aforementioned embodiments combined in any combination and represent exemplary embodiments. A fuller understanding of these embodiments is provided further herein below and in the Examples that follow.

Lipid-Based Formulations

Therapies based on the intracellular delivery of nucleic acids to target cells face both extracellular and intracellular barriers. Indeed, naked nucleic acid materials cannot be easily administered systemically due to their toxicity, low stability in serum, rapid renal clearance, reduced uptake by target cells, phagocyte uptake and their ability in activating the immune response, all features that preclude their clinical development. When exogenous nucleic acid material (e.g., mRNA) enters the human biological system, it is recognized by the reticuloendothelial system (RES) as foreign pathogens and cleared from blood circulation before having the chance to encounter target cells within or outside the vascular system. It has been reported that the half-life of naked nucleic acid in the blood stream is around several minutes (Kawabata K, Takakura Y, Hashida MPharm Res. 1995 Jun; 12(6):825-30). Chemical modification and a proper delivery method can reduce uptake by the RES and protect nucleic acids from degradation by ubiquitous nucleases, which increase stability and efficacy of nucleic acid-based therapies. In addition, RNAs or DNAs are anionic hydrophilic polymers that are not favorable for uptake by cells, which are also anionic at the surface. The success of nucleic acid-based therapies thus depends largely on the development of vehicles or vectors that can efficiently and effectively deliver genetic material to target cells and obtain sufficient levels of expression in vivo with minimal toxicity.

Moreover, upon internalization into a target cell, nucleic acid delivery vectors are challenged by intracellular barriers, including endosome entrapment, lysosomal degradation, nucleic acid unpacking from vectors, translocation across the nuclear membrane (for DNA), and release at the cytoplasm (for RNA). Successful nucleic acid-based therapy thus depends upon the ability of the vector to deliver the nucleic acids to the target sites inside of the cells to obtain sufficient levels of a desired activity such as expression of a gene.

While several gene therapies have been able to successfully utilize a viral delivery vector (e.g., AAV), lipid-based formulations have been increasingly recognized as one of the most promising delivery systems for RNA and other nucleic acid compounds due to their biocompatibility and their ease of large-scale production. One of the most significant advances in lipid-based nucleic acid therapies happened in August 2018 when Patisiran (ALN-TTR02) was the first siRNA therapeutic approved by both the Food and Drug Administration (FDA) and the European Commission (EC). ALN-TTR02 is an siRNA formulation based upon the so-called Stable Nucleic Acid Lipid Particle (SNALP) transfecting technology. Despite the success of Patisiran, the delivery of nucleic acid therapeutics, including mRNA, via lipid formulations is still undergoing development.

Some art-recognized lipid-formulated delivery vehicles for nucleic acid therapeutics include, according to various embodiments, polymer based carriers, such as polyethylene-imine (PEI), lipidoid-containing formulations, lipid nanoparticles and liposomes, nanoliposomes, ceramide-containing nanoliposomes, multivesicular liposomes, proteoliposomes, both natural and synthetically-derived exosomes, natural, synthetic and semi-synthetic lamellar bodies, nanoparticulates, micelles, and emulsions.

These lipid formulations vary in their structure and composition, and as can be expected in a rapidly evolving field, several different terms have been used in the art to describe a single type of delivery vehicle. At the same time, the terms for lipid formulations have frequently been conflated throughout the scientific literature, and this inconsistent use has caused confusion as to the exact meaning of several terms for lipid formulations. Among the several potential lipid formulations, liposomes, cationic liposomes, and lipid nanoparticles are specifically described in detail and defined herein for the purposes of the present disclosure.

Liposomes

Conventional liposomes are vesicles that consist of at least one bilayer and an internal aqueous compartment. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphiphilic polymers and surfactants (e.g., polymerosomes, niosomes, etc.). They generally present as spherical vesicles and can range in size from 20 nm to several microns. Liposomal formulations can be prepared as a colloidal dispersion or they can be lyophilized to reduce stability risks and to improve the shelf-life for liposome-based drugs. Methods of preparing liposomal compositions are known in the art and are within the skill of an ordinary artisan.

Liposomes that have only one bilayer are referred to as being unilamellar, and those having more than one bilayer are referred to as multilamellar. The most common types of liposomes are small unilamellar vesicles (SUV), large unilamellar vesicles (LUV), and multilamellar vesicles (MLV). In contrast to liposomes, lysosomes, micelles, and reversed micelles are composed of monolayers of lipids. Generally, a liposome is thought of as having a single interior compartment, however some formulations can be multivesicular liposomes (MVL), which consist of numerous discontinuous internal aqueous compartments separated by several non-concentric lipid bilayers.

Liposomes have long been perceived as drug delivery vehicles because of their superior biocompatibility, given that liposomes are basically analogs of biological membranes and can be prepared from both natural and synthetic phospholipids (Int. J. Nanomedicine. 2014; 9:1833-1843). In their use as drug delivery vehicles, hydrophilic solutes dissolved in the liposomal core cannot readily pass through the bilayer's hydrophobic membrane, and hydrophobic compounds will associate with the bilayer. Thus, a liposome can be loaded with hydrophobic and/or hydrophilic molecules. When a liposome is used to carry a nucleic acid such as RNA, the nucleic acid is contained within the liposomal compartment in an aqueous phase.

Cationic Liposomes

Liposomes can be composed of cationic, anionic, and/or neutral lipids. As an important subclass of liposomes, cationic liposomes are liposomes that are made in whole or part from positively charged lipids, or more specifically a lipid that comprises both a cationic group and a lipophilic portion. In addition to the general characteristics profiled above for liposomes, the positively charged moieties of cationic lipids used in cationic liposomes provide several advantages and some unique structural features. For example, the lipophilic portion of the cationic lipid is hydrophobic and thus will direct itself away from the aqueous interior of the liposome and associate with other nonpolar and hydrophobic species. Conversely, the cationic moiety will associate with aqueous media and more importantly with polar molecules and species with which it can complex in the aqueous interior of the cationic liposome. For these reasons, cationic liposomes are increasingly being researched for use in gene therapy due to their favorability towards negatively charged nucleic acids via electrostatic interactions, resulting in complexes that offer biocompatibility, low toxicity, and the possibility of the large-scale production required for in vivo clinical applications. Cationic lipids suitable for use in cationic liposomes are listed hereinbelow.

Lipid Nanoparticles

In contrast to liposomes and cationic liposomes, lipid nanoparticles (LNP) have a structure that includes a single monolayer or bilayer of lipids that encapsulates a compound in a solid phase. Thus, unlike liposomes, lipid nanoparticles do not have an aqueous phase or other liquid phase in its interior, but rather the lipids from the bilayer or monolayer shell are directly complexed to the internal compound thereby encapsulating it in a solid core. Lipid nanoparticles are typically spherical vesicles having a relatively uniform dispersion of shape and size. While the scientific literature varies on what size qualifies a lipid particle as being nanoparticulate, there is some overlap in agreement that a lipid nanoparticle can have a diameter in the range of 10 nm to 1000 nm. However, more commonly they are considered to be smaller than 120 nm or even 100 nm.

For lipid nanoparticle nucleic acid delivery systems, the lipid shell can be formulated to include an ionizable cationic lipid which can complex to and associate with the negatively charged backbone of the nucleic acid core. Ionizable cationic lipids with apparent pKa values below about 7 have the benefit of providing a cationic lipid for complexing with the nucleic acid's negatively charged backbone and loading into the lipid nanoparticle at pH values below the pKa of the ionizable lipid where it is positively charged. Then, at physiological pH values, the lipid nanoparticle can adopt a relatively neutral exterior allowing for a significant increase in the circulation half-lives of the particles following i.v. administration. In the context of nucleic acid delivery, lipid nanoparticles offer many advantages over other lipid-based nucleic acid delivery systems including high nucleic acid encapsulation efficiency, potent transfection, improved penetration into tissues to deliver therapeutics, and low levels of cytotoxicity and immunogenicity.

Prior to the development of lipid nanoparticle delivery systems for nucleic acids, cationic lipids were widely studied as synthetic materials for delivery of nucleic acid medicines. In these early efforts, after mixing together at physiological pH, nucleic acids were condensed by cationic lipids to form lipid-nucleic acid complexes known as lipoplexes. However, lipoplexes proved to be unstable and characterized by broad size distributions ranging from the submicron scale to a few microns. Lipoplexes, such as the Lipofectamine® reagent, have found considerable utility for in vitro transfection. However, these first-generation lipoplexes have not proven useful in vivo. The large particle size and positive charge (imparted by the cationic lipid) result in rapid plasma clearance, hemolytic and other toxicities, as well as immune system activation.

Lipid-mRNA Formulations

An mRNA as disclosed herein or a pharmaceutically acceptable salt thereof can be incorporated into a lipid formulation (i.e., a lipid-based delivery vehicle).

In the context of the present disclosure, a lipid-based delivery vehicle typically serves to transport a desired mRNA to a target cell or tissue. The lipid-based delivery vehicle can be any suitable lipid-based delivery vehicle known in the art. In some embodiments, the lipid-based delivery vehicle is a liposome, a cationic liposome, or a lipid nanoparticle containing an mRNA of the present disclosure. In some embodiments, the lipid-based delivery vehicle comprises a nanoparticle or a bilayer of lipid molecules and an mRNA of the present disclosure. In some embodiments, the lipid bilayer preferably further comprises a neutral lipid or a polymer. In some embodiments, the lipid formulation preferably comprises a liquid medium. In some embodiments, the formulation preferably further encapsulates a nucleic acid. In some embodiments, the lipid formulation preferably further comprises a nucleic acid and a neutral lipid or a polymer. In some embodiments, the lipid formulation preferably encapsulates the nucleic acid.

The description provides lipid formulations comprising one or more therapeutic mRNA molecules encapsulated within the lipid formulation. In some embodiments, the lipid formulation comprises liposomes. In some embodiments, the lipid formulation comprises cationic liposomes. In some embodiments, the lipid formulation comprises lipid nanoparticles.

In some embodiments, the mRNA is fully encapsulated within the lipid portion of the lipid formulation such that the mRNA in the lipid formulation is resistant in aqueous solution to nuclease degradation. In other embodiments, the lipid formulations described herein are substantially non-toxic to mammals such as humans.

The lipid formulations of the disclosure also typically have a total lipid:RNA ratio (mass/mass ratio) of from about 1:1 to about 100:1, from about 1:1 to about 50:1, from about 2:1 to about 45:1, from about 3:1 to about 40:1, from about 5:1 to about 38:1, or from about 6:1 to about 40:1, or from about 7:1 to about 35:1, or from about 8:1 to about 30:1; or from about 10:1 to about 25:1; or from about 8:1 to about 12:1; or from about 13:1 to about 17:1; or from about 18:1 to about 24:1; or from about 20:1 to about 30:1. In some preferred embodiments, the total lipid:RNA ratio (mass/mass ratio) is from about 10:1 to about 25:1. The ratio may be any value or subvalue within the recited ranges, including endpoints.

The lipid formulations of the present disclosure typically have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, about 100 nm, about 105 nm, about 110 nm, about 115 nm, about 120 nm, about 125 nm, about 130 nm, about 135 nm, about 140 nm, about 145 nm, or about 150 nm, and are substantially non-toxic. The diameter may be any value or subvalue within the recited ranges, including endpoints. In addition, nucleic acids, when present in the lipid nanoparticles of the present disclosure, are resistant in aqueous solution to degradation with a nuclease.

In preferred embodiments, the lipid formulations comprise an mRNA, a cationic lipid (e.g., one or more cationic lipids or salts thereof described herein), a phospholipid, and a conjugated lipid that inhibits aggregation of the particles (e.g., one or more PEG-lipid conjugates). The lipid formulations can also include cholesterol.

In the nucleic acid-lipid formulations, the mRNA may be fully encapsulated within the lipid portion of the formulation, thereby protecting the nucleic acid from nuclease degradation. In preferred embodiments, a lipid formulation comprising an mRNA is fully encapsulated within the lipid portion of the lipid formulation, thereby protecting the nucleic acid from nuclease degradation. In certain instances, the mRNA in the lipid formulation is not substantially degraded after exposure of the particle to a nuclease at 37° C. for at least 20, 30, 45, or 60 minutes. In certain other instances, the mRNA in the lipid formulation is not substantially degraded after incubation of the formulation in serum at 37° C. for at least 30, 45, or 60 minutes or at least 2, 3, 4, 5, 6, 7, 8, 9, 10, 12, 14, 16, 18, 20, 22, 24, 26, 28, 30, 32, 34, or 36 hours. In other embodiments, the mRNA is complexed with the lipid portion of the formulation.

In the context of nucleic acids, full encapsulation may be determined by performing a membrane-impermeable fluorescent dye exclusion assay, which uses a dye that has enhanced fluorescence when associated with a nucleic acid. Encapsulation is determined by adding the dye to a lipid formulation, measuring the resulting fluorescence, and comparing it to the fluorescence observed upon addition of a small amount of nonionic detergent. Detergent-mediated disruption of the lipid layer releases the encapsulated nucleic acid, allowing it to interact with the membrane-impermeable dye. Nucleic acid encapsulation may be calculated as $E=(I_0-I)/I_0$, where $I$ and $I_0$ refer to the fluorescence intensities before and after the addition of detergent.

In other embodiments, the present disclosure provides a nucleic acid-lipid composition comprising a plurality of nucleic acid-liposomes, nucleic acid-cationic liposomes, or nucleic acid-lipid nanoparticles. In some embodiments, the nucleic acid-lipid composition comprises a plurality of mRNA-liposomes. In some embodiments, the nucleic acid-lipid composition comprises a plurality of mRNA-cationic liposomes. In some embodiments, the nucleic acid-lipid composition comprises a plurality of mRNA-lipid nanoparticles.

In some embodiments, the lipid formulations comprise mRNA that is fully encapsulated within the lipid portion of the formulation, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99% (or any fraction thereof or range therein) of the particles have the mRNA encapsulated therein. The amount may be any value or subvalue within the recited ranges, including endpoints.

Depending on the intended use of the lipid formulation, the proportions of the components can be varied, and the delivery efficiency of a particular formulation can be measured using assays known in the art.

According to some embodiments, the expressible polynucleotides and mRNA constructs described herein are lipid formulated. The lipid formulation is preferably selected from, but not limited to, liposomes, cationic liposomes, and lipid nanoparticles. In one preferred embodiment, a lipid formulation is a cationic liposome or a lipid nanoparticle (LNP) comprising:

(a) an mRNA of the present disclosure,
(b) a cationic lipid,
(c) an aggregation reducing agent (such as polyethylene glycol (PEG) lipid or PEG-modified lipid),
(d) optionally a non-cationic lipid (such as a neutral lipid), and
(e) optionally, a sterol.

In one some embodiments, the cationic lipid is an ionizable cationic lipid. In one embodiment, the lipid nanoparticle formulation consists of (i) at least one cationic lipid; (ii) a helper lipid; (iii) a sterol (e.g., cholesterol); and (iv) a PEG-lipid, in a molar ratio of about 20% to about 40% ionizable cationic lipid: about 25% to about 45% helper lipid: about 25% to about 45% sterol; about 0.5-5% PEG-lipid. Example cationic lipids (including ionizable cationic lipids), helper lipids (e.g., neutral lipids), sterols, and ligand-containing lipids (e.g., PEG-lipids) are described hereinbelow.

The selection of specific lipids and their relative % compositions depends on several factors including the desired therapeutic effect, the intended in vivo delivery target, and the planned dosing regimen and frequency. Generally, lipids that correspond to both high potency (i.e, therapeutic effect such as knockdown activity or translation efficiency) and biodegradability resulting in rapid tissue clearance are most preferred. However, biodegradability may be less important for formulations that are intended for only one or two administrations within the subject. In addition, the lipid composition may require careful engineering so that the lipid formulation preserves its morphology during in vivo administration and its journey to the intended target, but will then be able to release the active agent upon uptake into target cells. Thus, several formulations typically need to be evaluated in order to find the best possible combination of lipids in the best possible molar ratio of lipids as well as the ratio of total lipid to active ingredient.

Suitable lipid components and methods of manufacturing lipid nanoparticles are well known in the art and are described for example in PCT/US2020/023442, U.S. Pat. Nos. 8,058,069, 8,822,668, 9,738,593, 9,139,554, PCT/US2014/066242, PCT/US2015/030218, PCT/2017/015886, and PCT/US2017/067756, the contents of which are incorporated by reference.

Cationic Lipids

The lipid formulation preferably includes a cationic lipid suitable for forming a cationic liposome or lipid nanoparticle. Cationic lipids are widely studied for nucleic acid delivery because they can bind to negatively charged membranes and induce uptake. Generally, cationic lipids are amphiphiles containing a positive hydrophilic head group, two (or more) lipophilic tails, or a steroid portion and a connector between these two domains. Preferably, the cationic lipid carries a net positive charge at about physiological pH. Cationic liposomes have been traditionally the most commonly used non-viral delivery systems for oligonucleotides, including plasmid DNA, antisense oligos, and siRNA/small hairpin RNA-shRNA. Cationic lipids, such as DOTAP, (1,2-dioleoyl-3-trimethylammonium-propane) and DOTMA (N-[1-(2,3-dioleoyloxy)propyl]-N,N,N-trimethylammonium methyl sulfate) can form complexes or lipoplexes with negatively charged nucleic acids by electrostatic interaction, providing high in vitro transfection efficiency.

In the presently disclosed lipid formulations, the cationic lipid may be, for example, N,N-dioleyl-N,N-dimethylammonium chloride (DODAC), N,N-distearyl-N,N-dimethylammonium bromide (DDAB), 1,2-dioleoyltrimethylammoniumpropane chloride (DOTAP) (also known as N-(2,3-dioleoyloxy)propyl)-N,N,N-trimethylammonium chloride and 1,2-Dioleyloxy-3-trimethylaminopropane chloride salt), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-di-γ-linolenyloxy-N,N-dimethylaminopropane (γ-DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.Cl), 1,2-Dilinoleoyl-3-trimethylaminopropane chloride salt (DLin-TAP.Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanediol (DOAP), 1,2-Dilinoleyloxo-3-(2-N,N-dimethylamino)ethoxypropane (DLin-EG-DMA), 2,2-Dilinoleyl-4-dimethylaminomethyl-[1,3]-dioxolane (DLin-K-DMA) or analogs thereof, (3aR,5s,6a5)-N,N-dimethyl-2,2-di((9Z,12Z)-octadeca-9,12-dienyl)tetrahydro-3aH-cyclopenta[d][1,3]dioxol-5-amine, (6Z,9Z,28Z,31Z)-heptatriaconta-6, 9,28,31-tetraen-19-yl4-(dim ethyl amino) butanoate (MC3), 1,1'-(2-(4-(2-((2-(bis (2-hydroxydodecyl) amino)ethyl)(2-hydroxydodecyl)amino)ethyl)piperazin-1-yl)ethylazanediyl)didodecan-2-ol (C12-200), 2,2-dilinoleyl-4-(2-dimethylaminoethyl)-[1,3]-dioxolane (DLin-K-C2-DMA), 2,2-dilinoleyl-4-dimethylaminomethyl-[1,3]-dioxolane (DLin-K-DMA), (6Z,9Z,28Z,31Z)-heptatriaconta-6, 9,28 31-tetraen-19-yl 4-(dim ethyl amino) butanoate (DLin-M-C3 -DMA), 3 -((6Z,9Z,28Z,31Z)-heptatriaconta-6, 9,28,3 1-tetraen-19-yloxy)-N,N-dimethylpropan-1-amine (MC3 Ether), 4-((6Z,9Z,28Z,31 Z)-heptatriaconta-6,9,28,31-tetraen-19-yloxy)-N,N-dimethylbutan-1-amine (MC4 Ether), or any combination thereof. Other cationic lipids include, but are not limited to, N,N-distearyl-N,N-dimethylammonium bromide (DDAB), 3P-(N-(N',N'-dimethylaminoethane)-carbamoyl)cholesterol (DC-Choi), N-(1-(2,3-dioleyloxy)propyl)-N-2-(sperminecarboxamido) ethyl)-N,N-dimethyl ammonium trifluoracetate (DOSPA), dioctadecylamidoglycyl carboxyspermine (DOGS), 1,2-dileoyl-sn-3-phosphoethanolamine (DOPE), 1,2-dioleoyl-3-dimethylammonium propane (DODAP), N-(1,2-dimyristyloxyprop-3-yl)-N,N-dimethyl-N-hydroxyethyl ammonium bromide (DMRIE), and 2,2-Dilinoleyl-4-dimethylaminoethyl-[1,3]-dioxolane (XTC). Additionally, commercial preparations of cationic lipids can be used, such as, e.g., LIPOFECTIN (including DOTMA and DOPE, available from GIBCO/BRL), and Lipofectamine (comprising DOSPA and DOPE, available from GIBCO/BRL).

Other suitable cationic lipids are disclosed in International Publication Nos. WO 09/086558, WO 09/127060, WO 10/048536, WO 10/054406, WO 10/088537, WO 10/129709, and WO 2011/153493; U.S. Patent Publication Nos. 2011/0256175, 2012/0128760, and 2012/0027803; U.S. Pat. No. 8,158,601; and Love et al., PNAS, 107(5), 1864-69, 2010, the contents of which are herein incorporated by reference.

Other suitable cationic lipids include those having alternative fatty acid groups and other dialkylamino groups, including those, in which the alkyl substituents are different (e.g., N-ethyl-N-methylamino-, and N-propyl-N-ethylamino-). These lipids are part of a subcategory of cationic lipids referred to as amino lipids. In some embodiments of the lipid formulations described herein, the cationic lipid is an amino lipid. In general, amino lipids having less saturated acyl chains are more easily sized, particularly when the complexes must be sized below about 0.3 microns, for purposes of filter sterilization. Amino lipids containing unsaturated fatty acids with carbon chain lengths in the range of $C_{14}$ to $C_{22}$ may be used. Other scaffolds can also be used to separate the amino group and the fatty acid or fatty alkyl portion of the amino lipid.

In some embodiments, the lipid formulation comprises the cationic lipid with Formula I according to the patent application PCT/EP2017/064066. In this context, the disclosure of PCT/EP2017/064066 is also incorporated herein by reference.

In some embodiments, amino or cationic lipids of the present disclosure are ionizable and have at least one protonatable or deprotonatable group, such that the lipid is positively charged at a pH at or below physiological pH (e.g., pH 7.4), and neutral at a second pH, preferably at or above physiological pH. Of course, it will be understood that the addition or removal of protons as a function of pH is an equilibrium process, and that the reference to a charged or a neutral lipid refers to the nature of the predominant species and does not require that all of the lipid be present in the charged or neutral form. Lipids that have more than one protonatable or deprotonatable group, or which are zwitterionic, are not excluded from use in the disclosure. In certain embodiments, the protonatable lipids have a pKa of the protonatable group in the range of about 4 to about 11. In some embodiments, the ionizable cationic lipid has a pKa of about 5 to about 7. In some embodiments, the pKa of an ionizable cationic lipid is about 6 to about 7.

In some embodiments, the lipid formulation comprises an ionizable cationic lipid of Formula I:

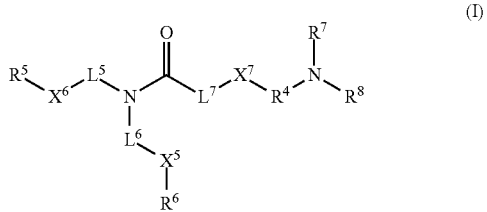

(I)

or a pharmaceutically acceptable salt or solvate thereof, wherein $R^5$ and $R^6$ are each independently selected from the group consisting of a linear or branched $C_1$-$C_{31}$ alkyl, $C_2$-$C_{31}$ alkenyl or $C_2$-$C_{31}$ alkynyl and cholesteryl; $L^5$ and $L^6$ are each independently selected from the group consisting of a linear $C_1$-$C_{20}$ alkyl and $C_2$-$C_{20}$ alkenyl; $X^5$ is —C(O)O—, whereby —C(O)O—$R^6$ is formed or —OC(O)— whereby —OC(O)—$R^6$ is formed; $X^6$ is —C(O)O— whereby —C(O)O—$R^5$ is formed or —OC(O)— whereby —OC(O)—$R^5$ is formed; $X^7$ is S or O; $L^7$ is absent or lower alkyl; $R^4$ is a linear or branched $C_1$-$C_6$ alkyl; and $R^7$ and $R^8$ are each independently selected from the group consisting of a hydrogen and a linear or branched $C_1$-$C_6$ alkyl.

In some embodiments, $X^7$ is S.

In some embodiments, $X^5$ is —C(O)O—, whereby —C(O)O—$R^6$ is formed and $X^6$ is —C(O)O— whereby —C(O)O—$R^5$ is formed.

In some embodiments, $R^7$ and $R^8$ are each independently selected from the group consisting of methyl, ethyl and isopropyl.

In some embodiments, $L^5$ and $L^6$ are each independently a $C_1$-$C_{10}$ alkyl. In some embodiments, $L^5$ is $C_1$-$C_3$ alkyl, and $L^6$ is $C_1$-$C_5$ alkyl. In some embodiments, $L^6$ is $C_1$-$C_2$ alkyl. In some embodiments, $L^5$ and $L^6$ are each a linear $C_7$ alkyl. In some embodiments, $L^5$ and $L^6$ are each a linear $C_9$ alkyl.

In some embodiments, $R^5$ and $R^6$ are each independently an alkenyl. In some embodiments, $R^6$ is alkenyl. In some embodiments, $R^6$ is $C_2$-$C_9$ alkenyl. In some embodiments, the alkenyl comprises a single double bond. In some embodiments, $R^5$ and $R^6$ are each alkyl. In some embodiments, $R^5$ is a branched alkyl. In some embodiments, $R^5$ and $R^6$ are each independently selected from the group consisting of a $C_9$ alkyl, $C_9$ alkenyl and $C_9$ alkynyl. In some embodiments, $R^5$ and $R^6$ are each independently selected from the group consisting of a $C_{11}$ alkyl, $C_{11}$ alkenyl and $C_{11}$ alkynyl. In some embodiments, $R^5$ and $R^6$ are each independently selected from the group consisting of a $C_7$ alkyl, $C_7$ alkenyl and $C_7$ alkynyl. In some embodiments, $R^5$ is —CH$((CH_2)_pCH_3)_2$ or —CH$((CH_2)_pCH_3)((CH_2)_{p-1}CH_3)$, wherein p is 4-8. In some embodiments, p is 5 and $L^5$ is a $C_1$-$C_3$ alkyl. In some embodiments, p is 6 and $L^5$ is a $C_3$ alkyl. In some embodiments, p is 7. In some embodiments, p is 8 and $L^5$ is a $C_1$-$C_3$ alkyl. In some embodiments, $R^5$ consists of —CH$((CH_2)_pCH_3)((CH_2)_{p-1}CH_3)$, wherein p is 7 or 8.

In some embodiments, $R^4$ is ethylene or propylene. In some embodiments, $R^4$ is n-propylene or isobutylene.

In some embodiments, $L^7$ is absent, $R^4$ is ethylene, $X^7$ is S and $R^7$ and $R^8$ are each methyl. In some embodiments, $L^7$ is absent, $R^4$ is n-propylene, $X^7$ is S and $R^7$ and $R^8$ are each methyl. In some embodiments, $L^7$ is absent, $R^4$ is ethylene, $X^7$ is S and $R^7$ and $R^8$ are each ethyl.

In some embodiments, $X^7$ is S, $X^5$ is —C(O)O—, whereby —C(O)O—$R^6$ is formed, $X^6$ is —C(O)O— whereby —C(O)O—$R^5$ is formed, $L^5$ and $L^6$ are each independently a linear $C_3$-$C_7$ alkyl, $L^7$ is absent, $R^5$ is —CH$((CH_2)_pCH_3)_2$, and $R^6$ is $C_7$-$C_{12}$ alkenyl. In some further embodiments, p is 6 and $R^6$ is $C_9$ alkenyl.

In some embodiments, the lipid formulation comprises an ionizable cationic lipid selected from the group consisting of

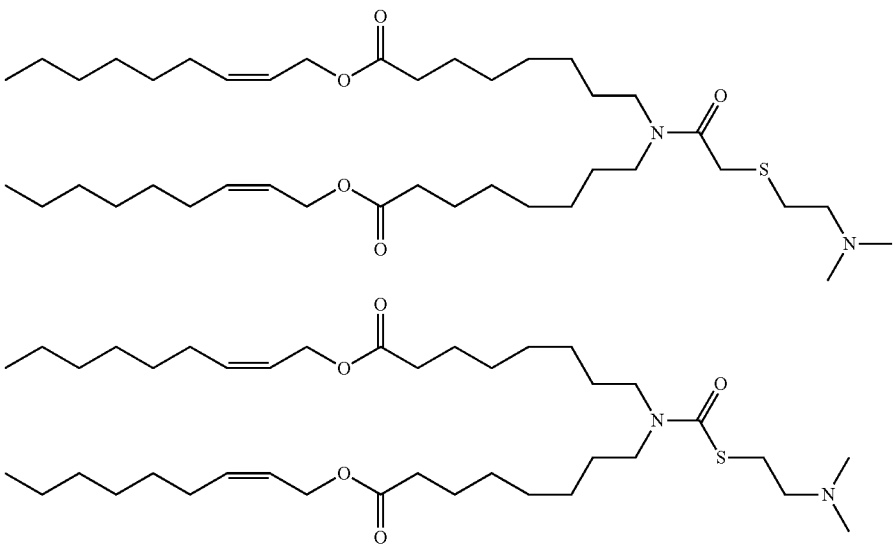

-continued
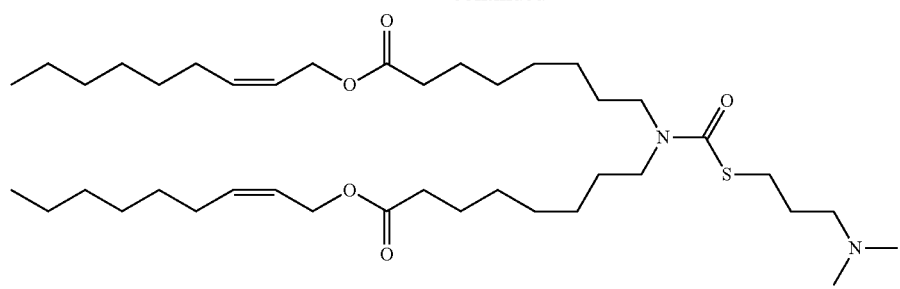
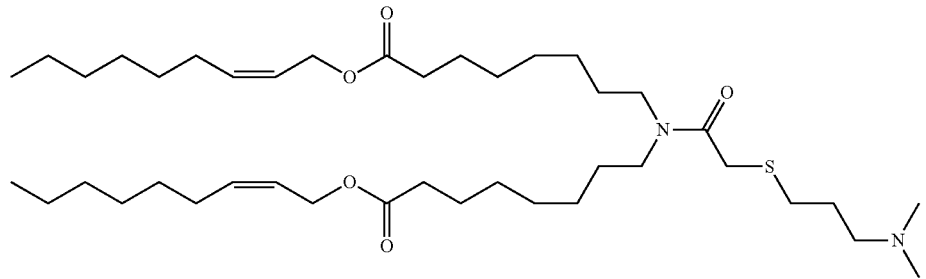
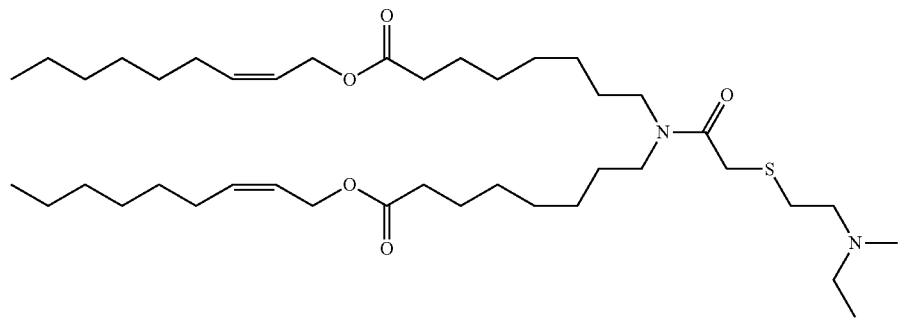
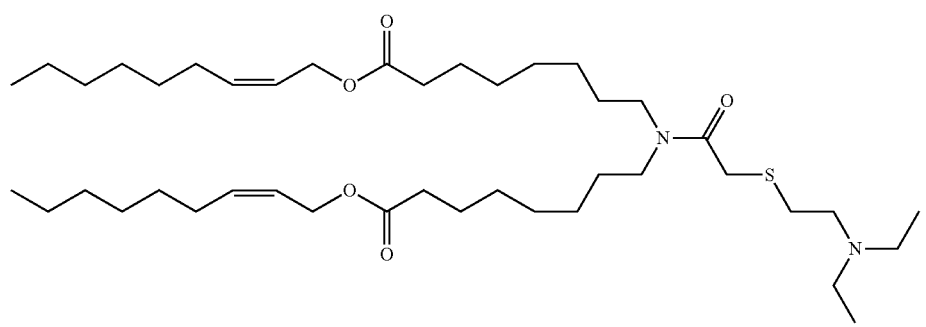
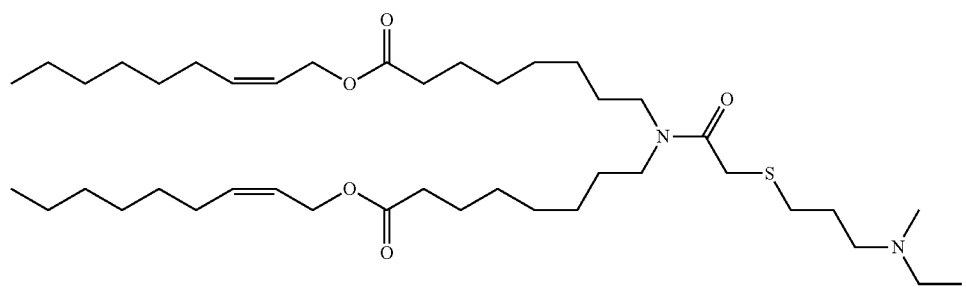

-continued
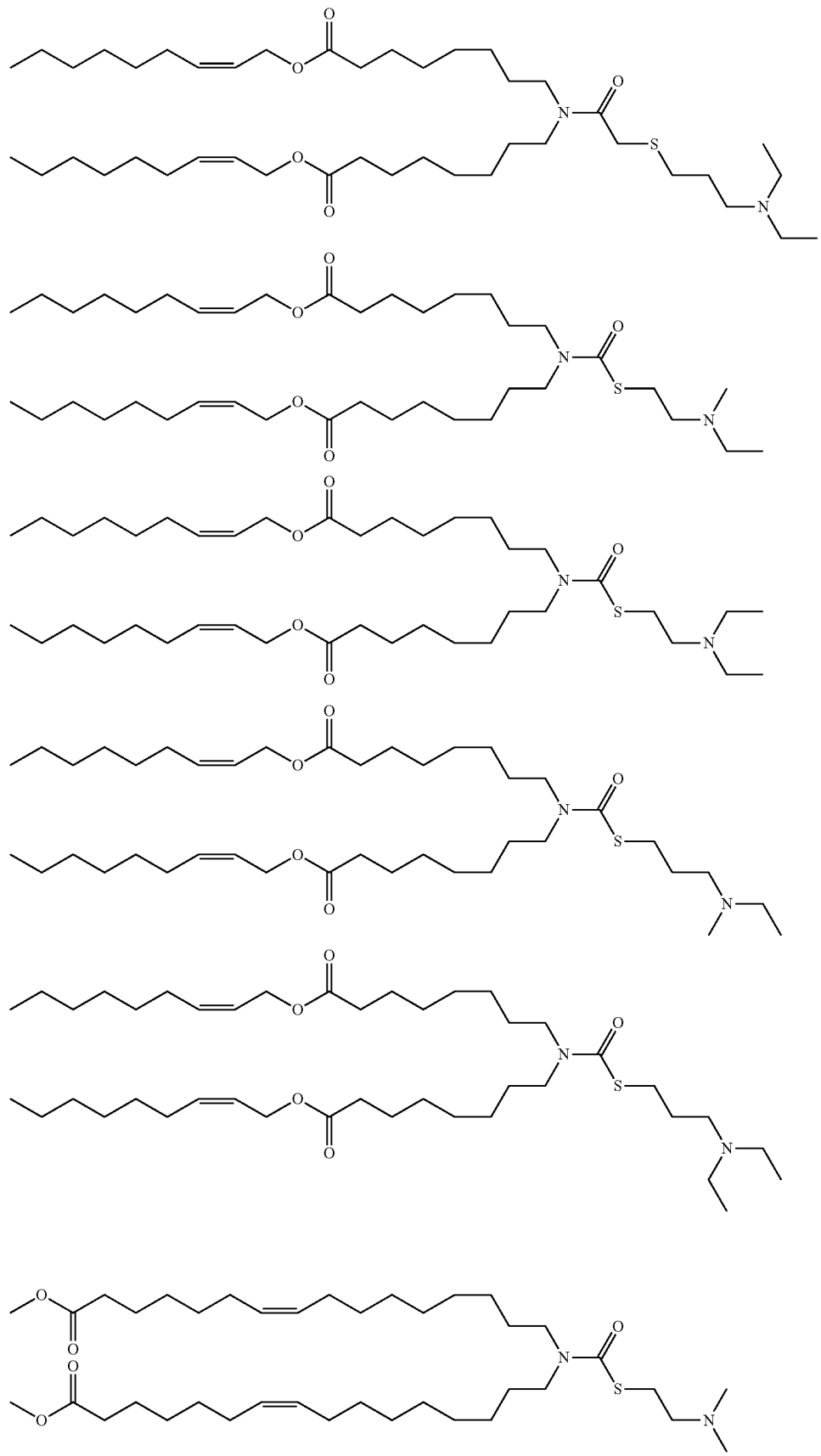

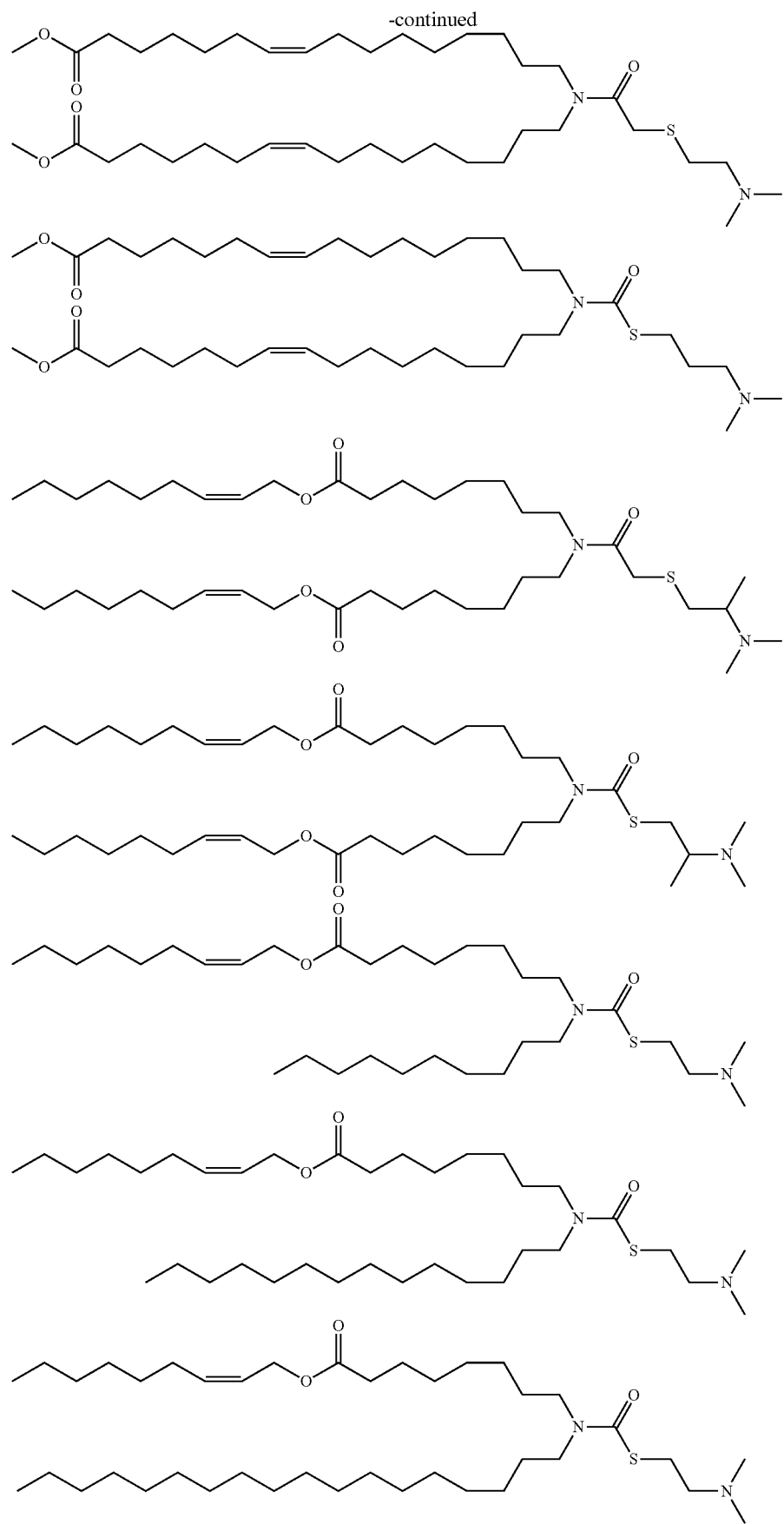

-continued
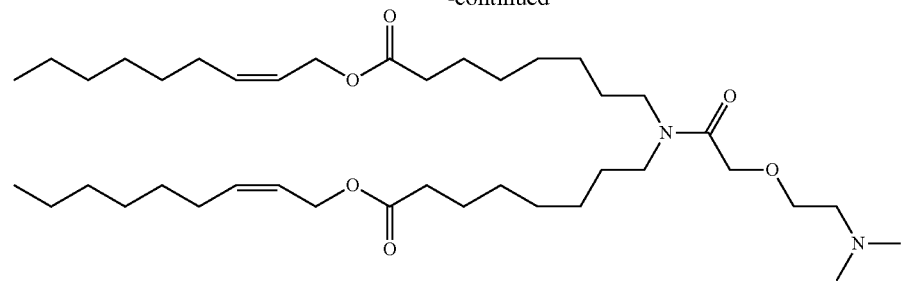
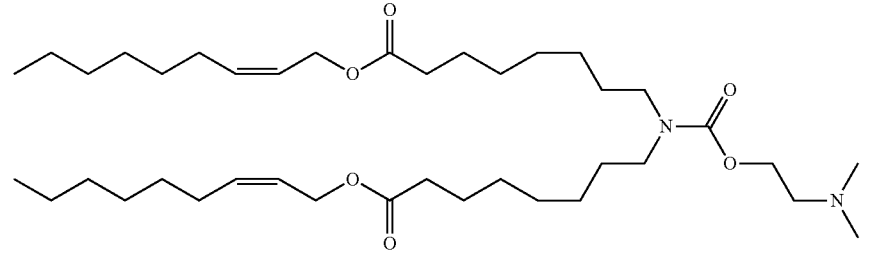
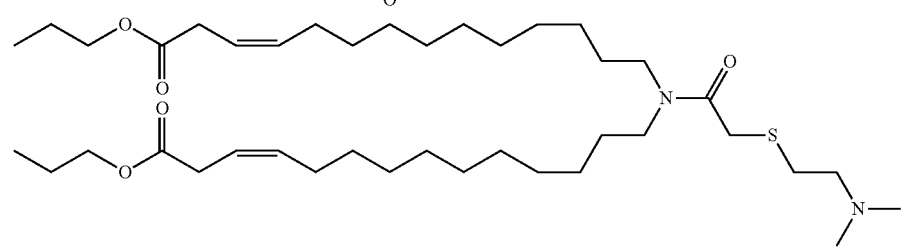
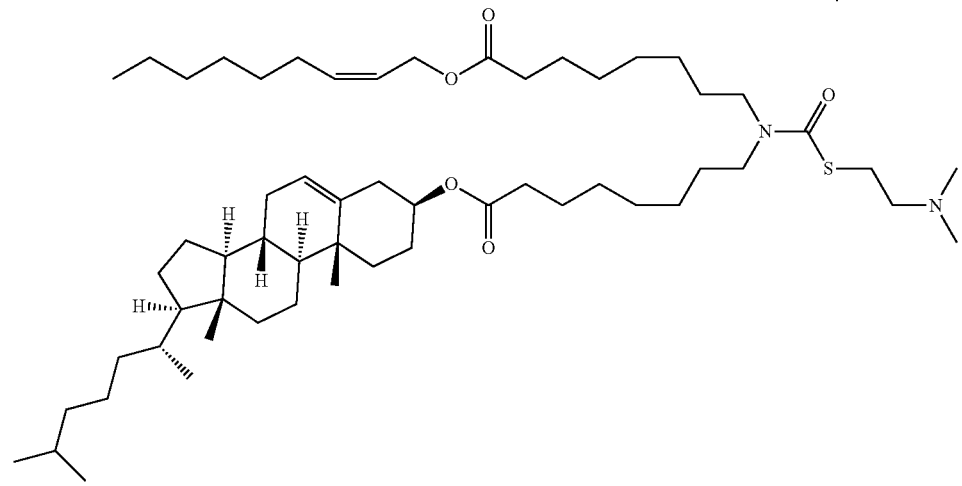
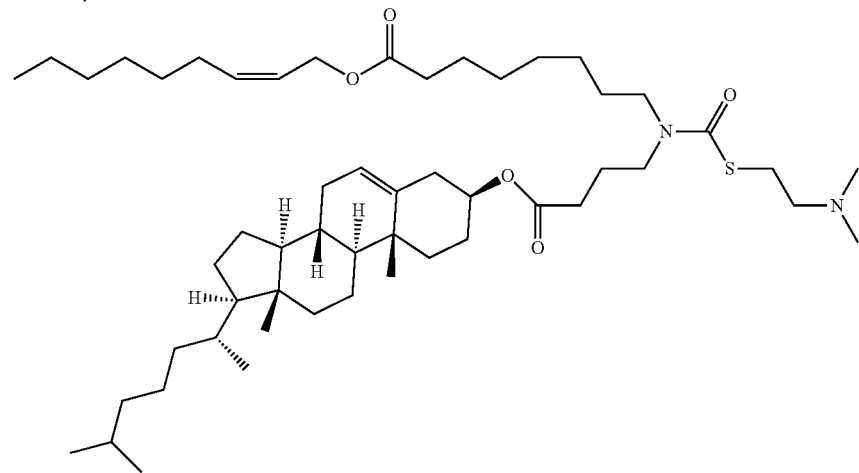

-continued
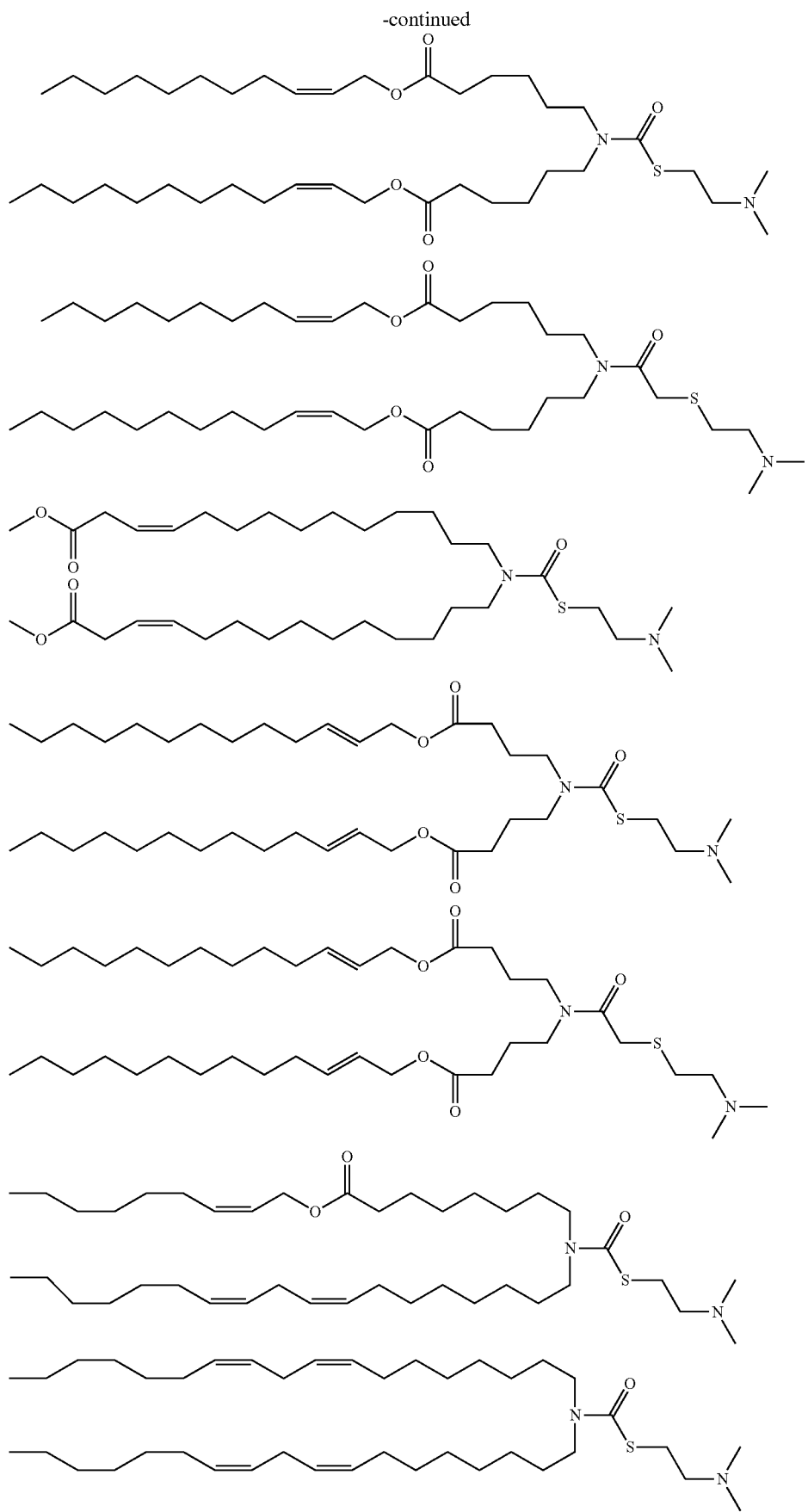

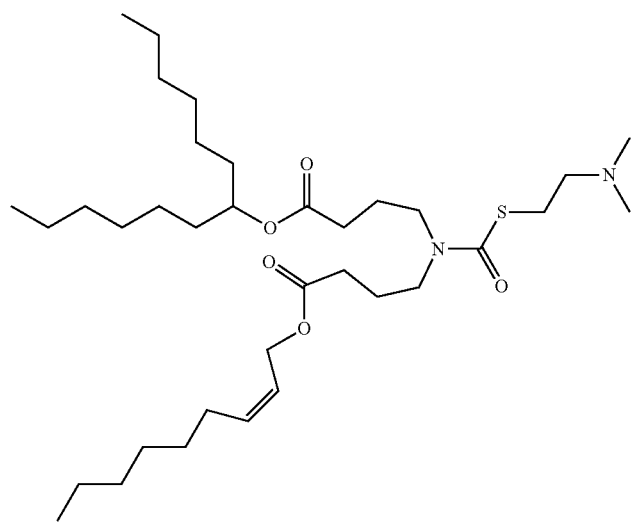
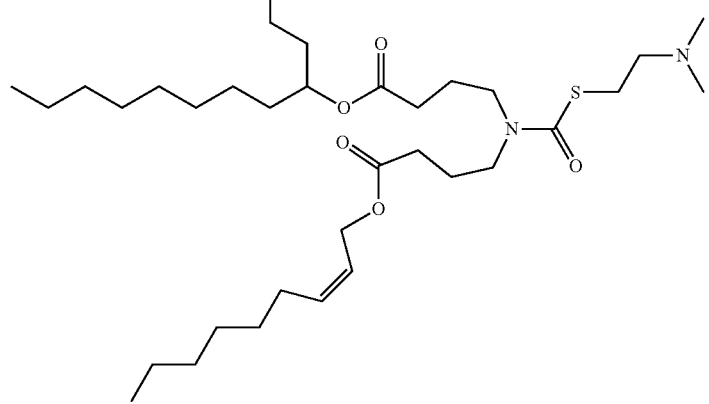
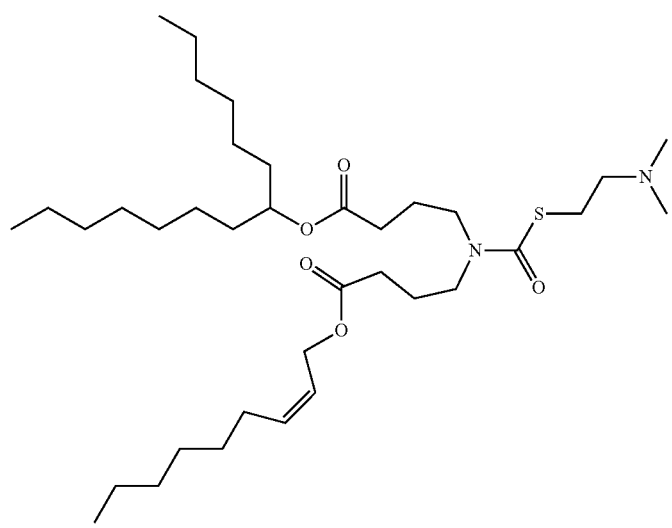

-continued
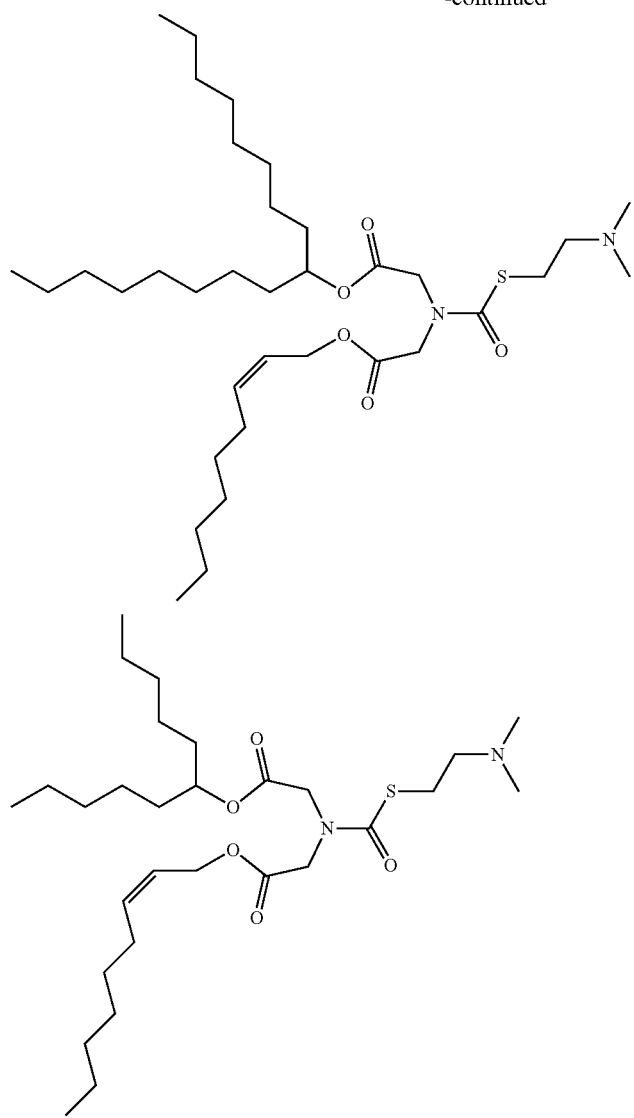
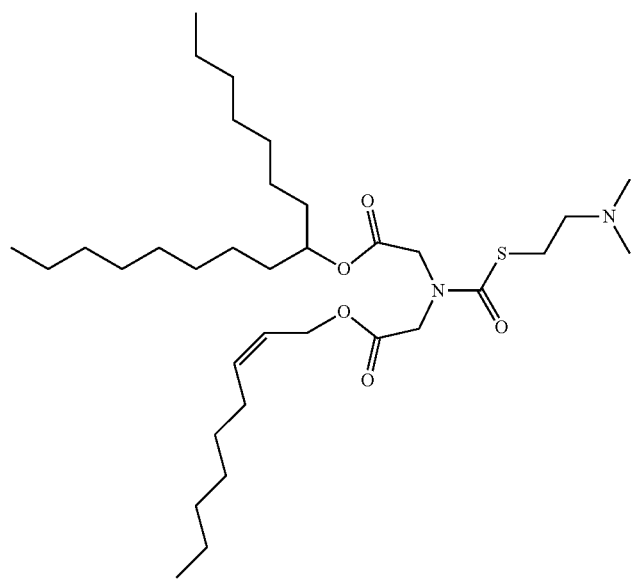

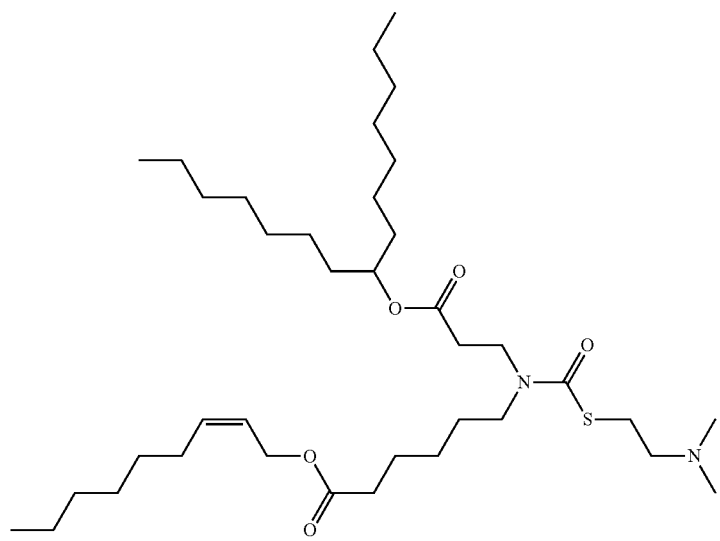
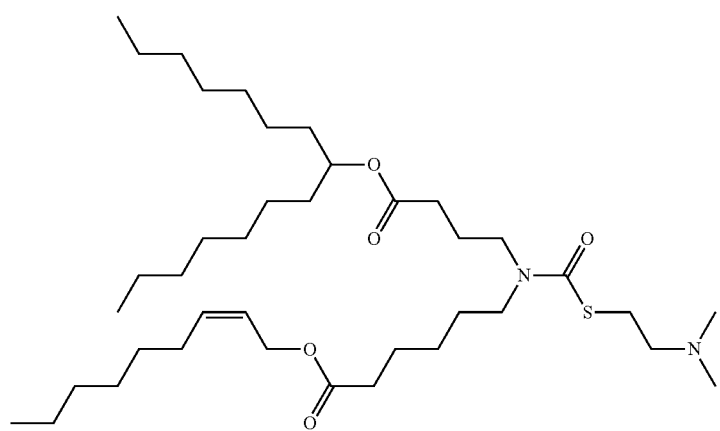
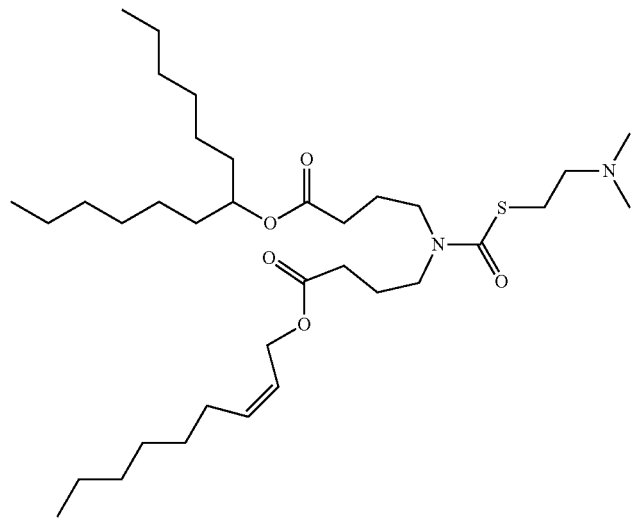

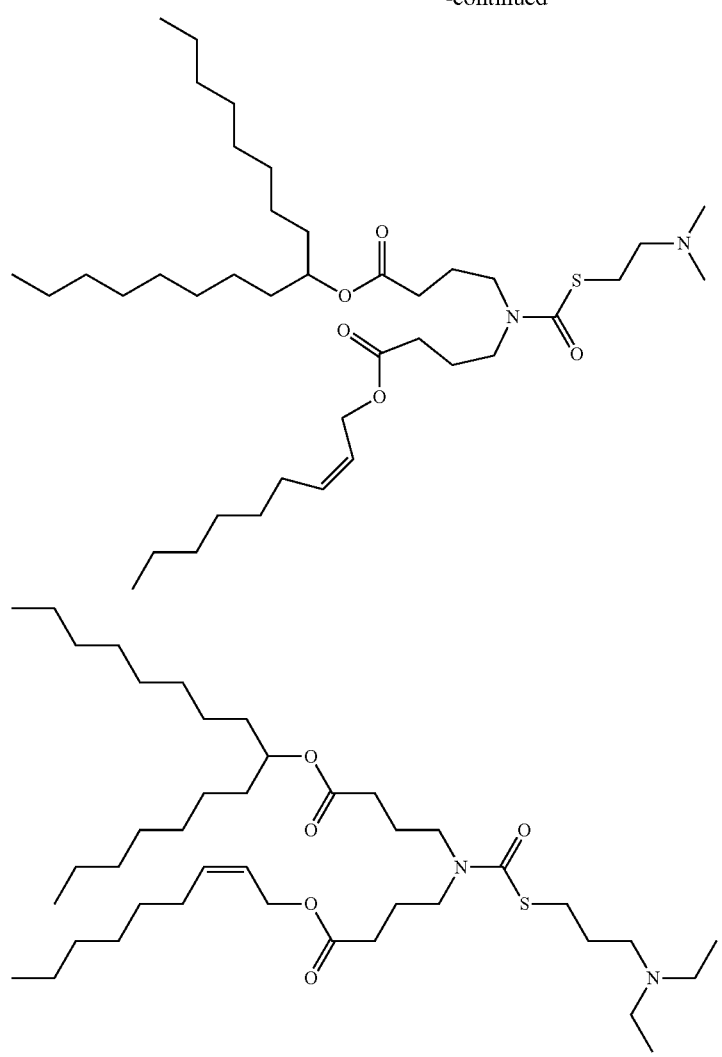
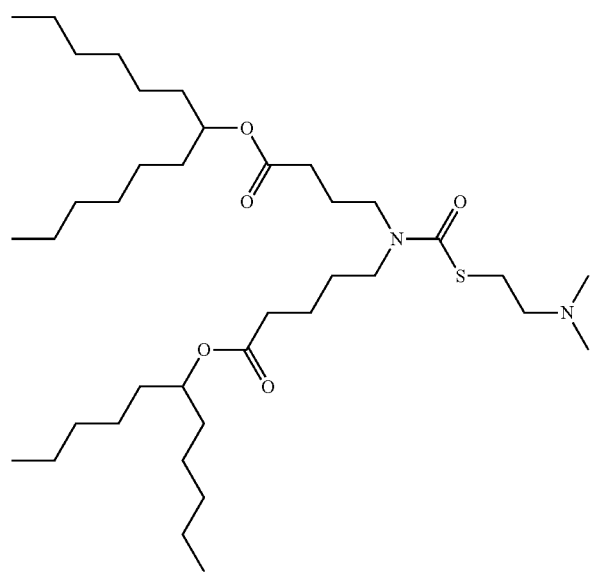

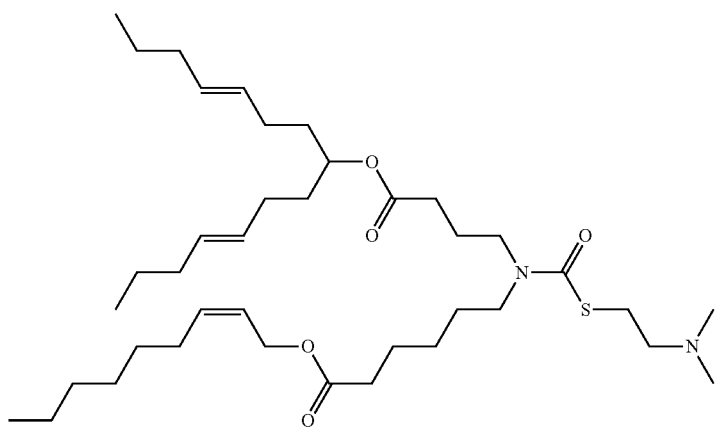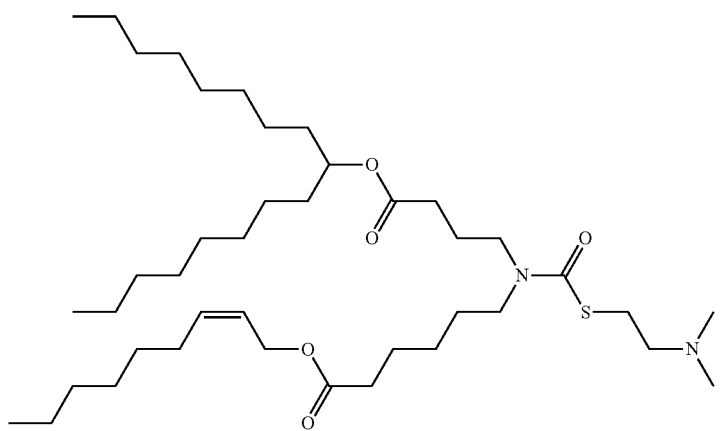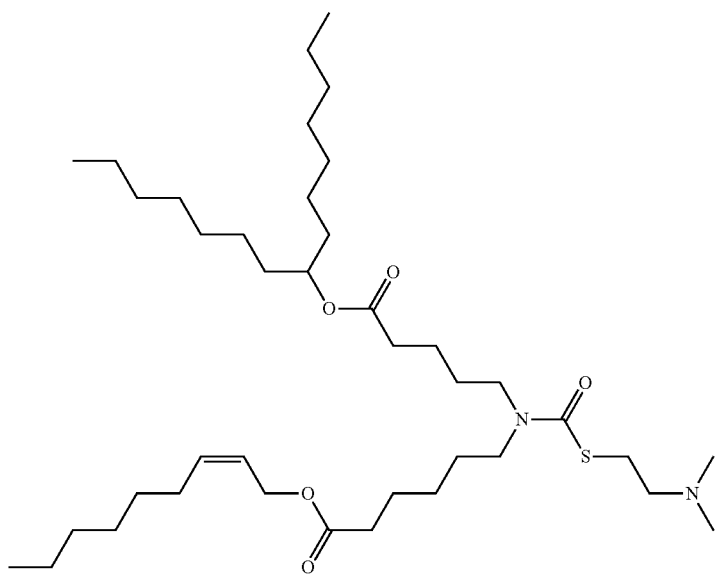

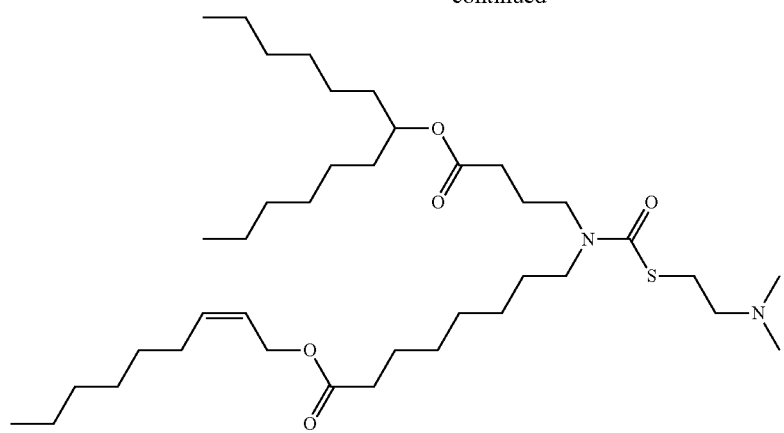
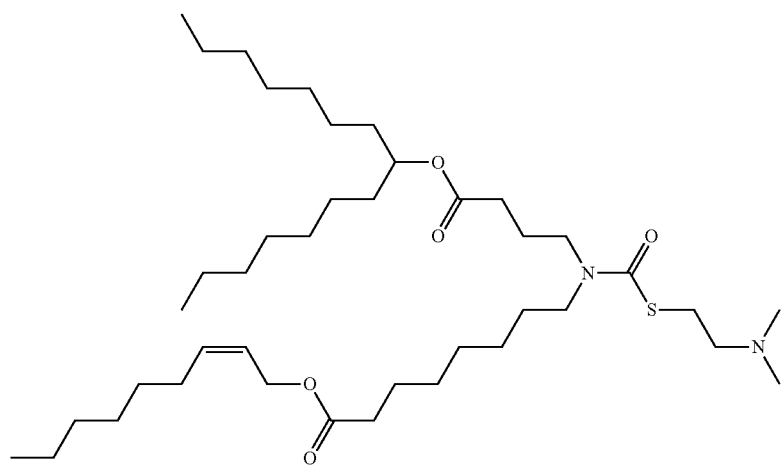
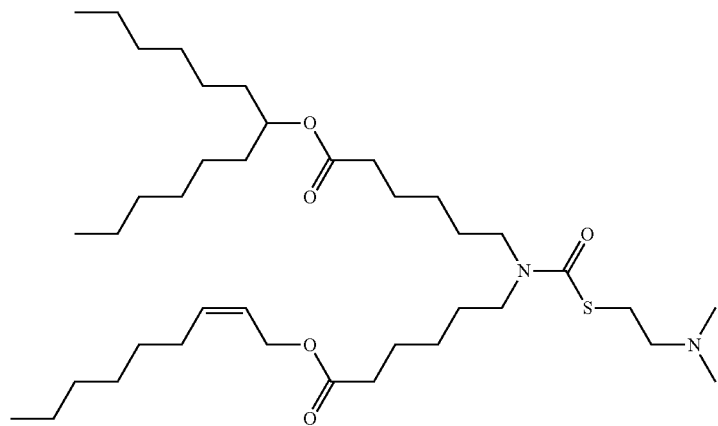

-continued
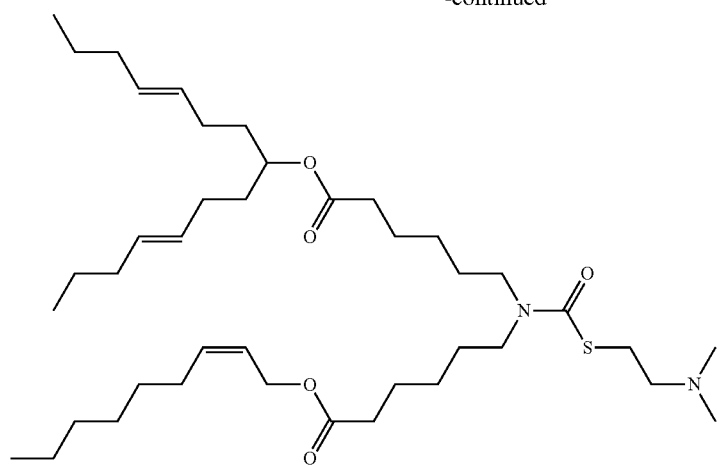
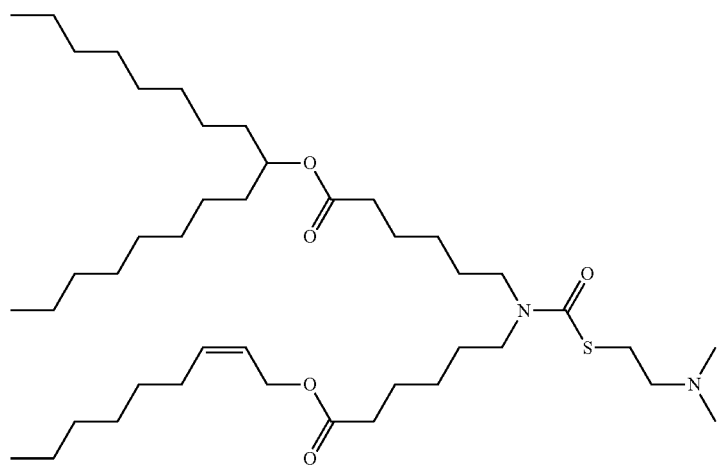
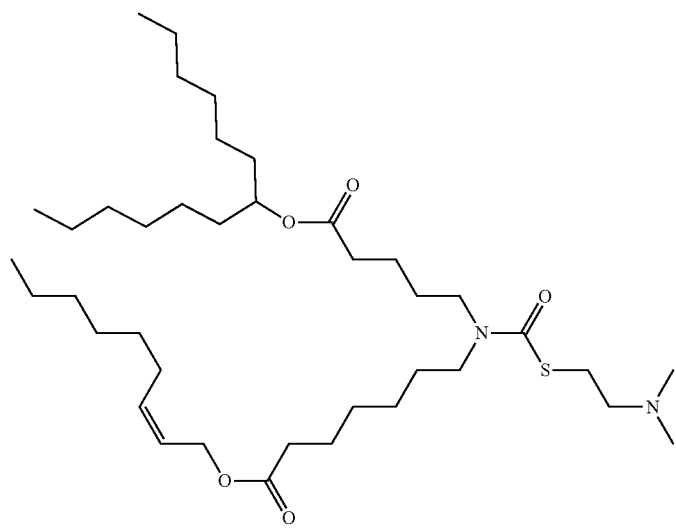

-continued
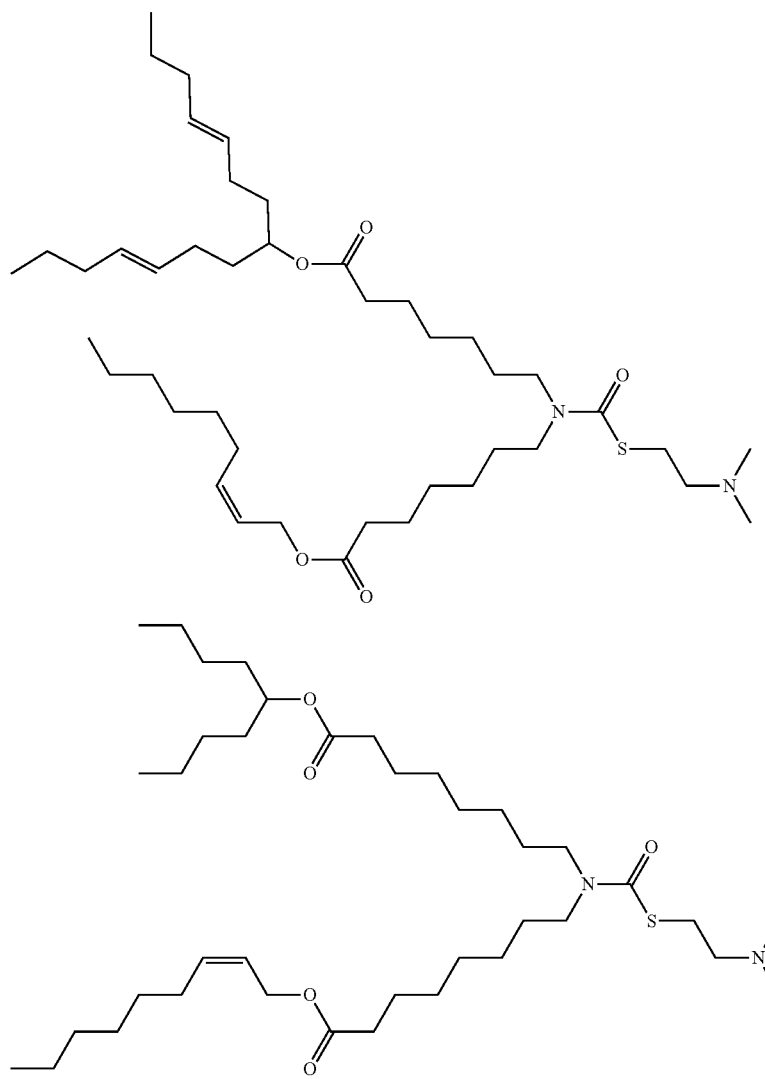
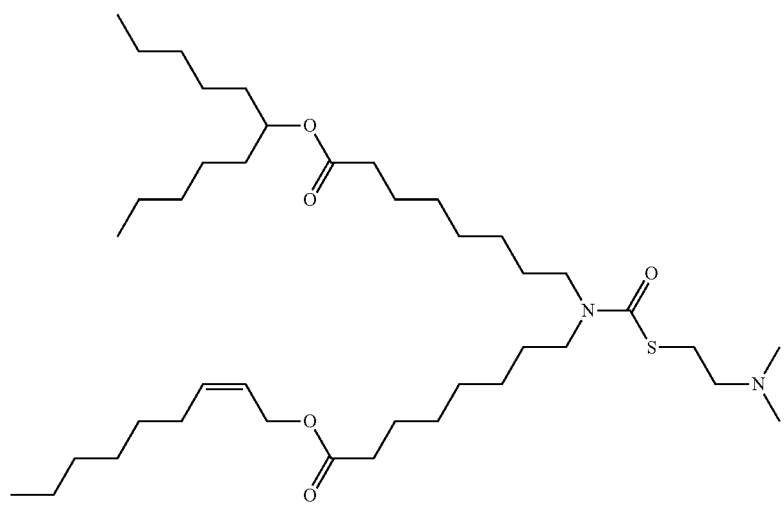

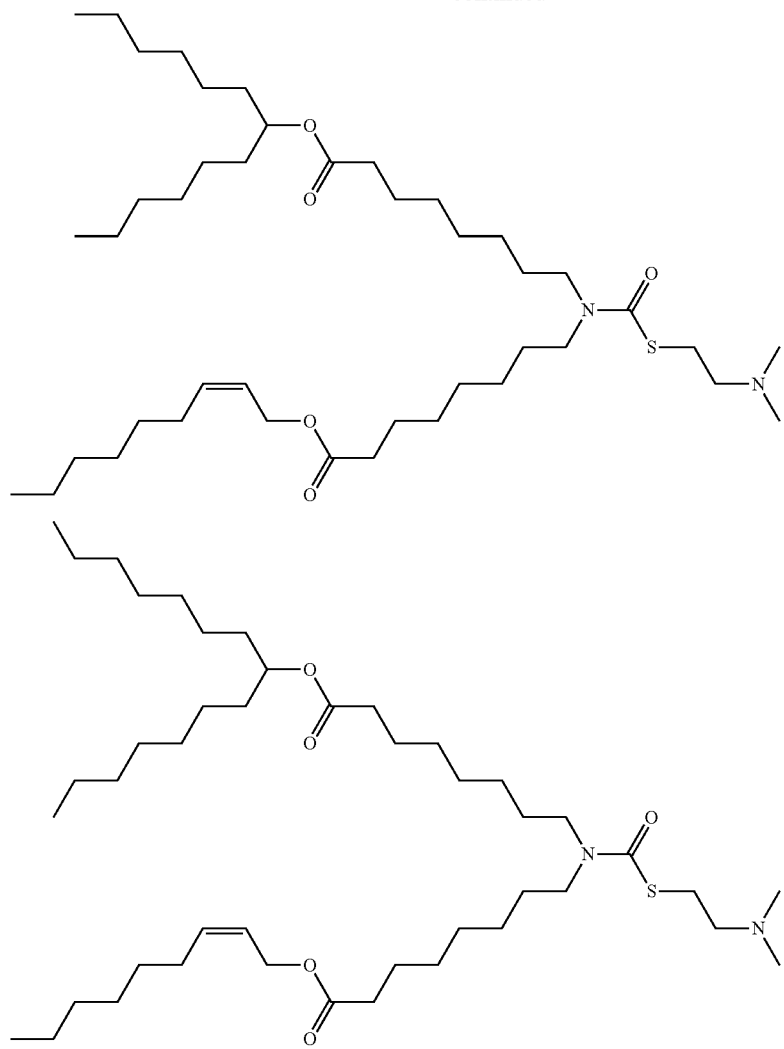
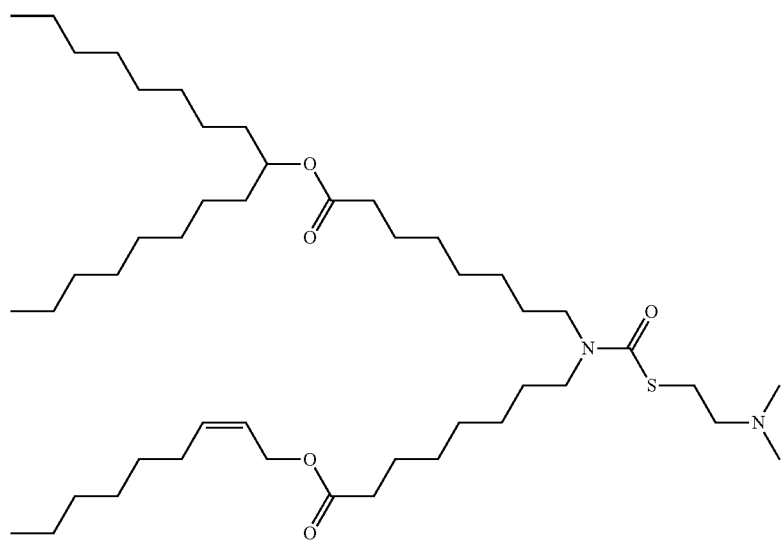

-continued
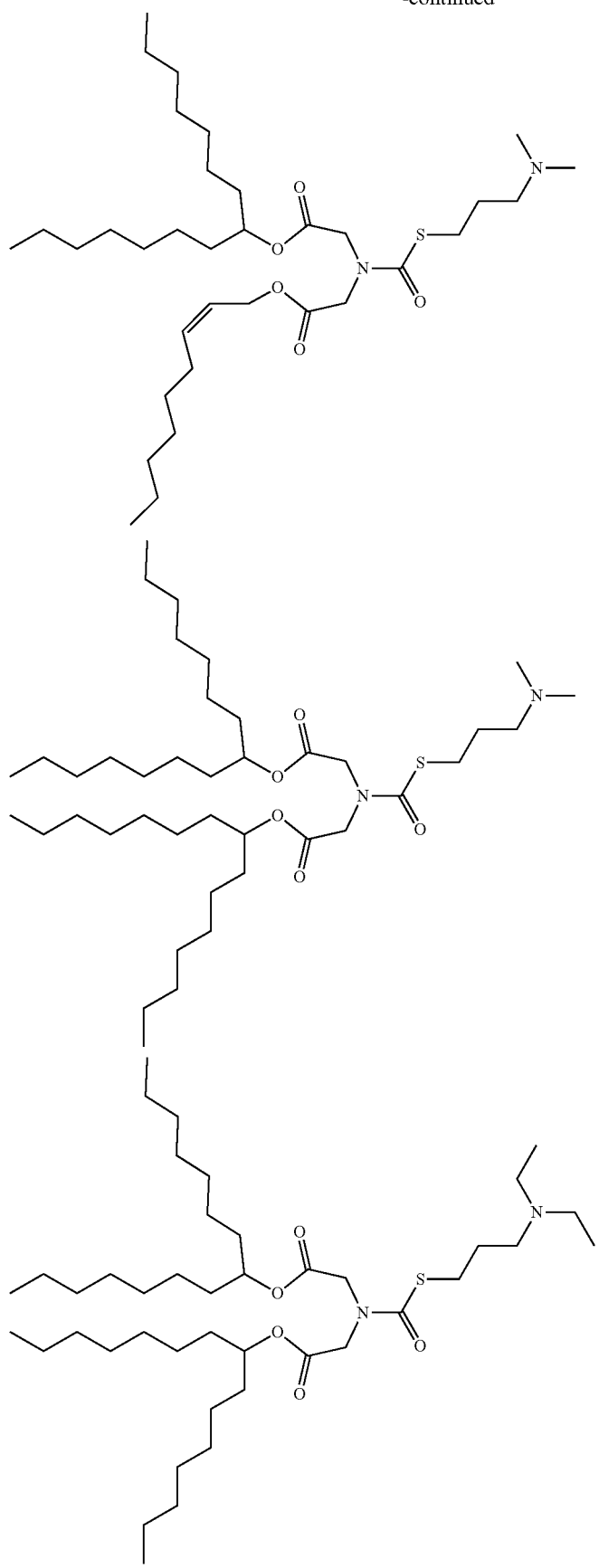

-continued
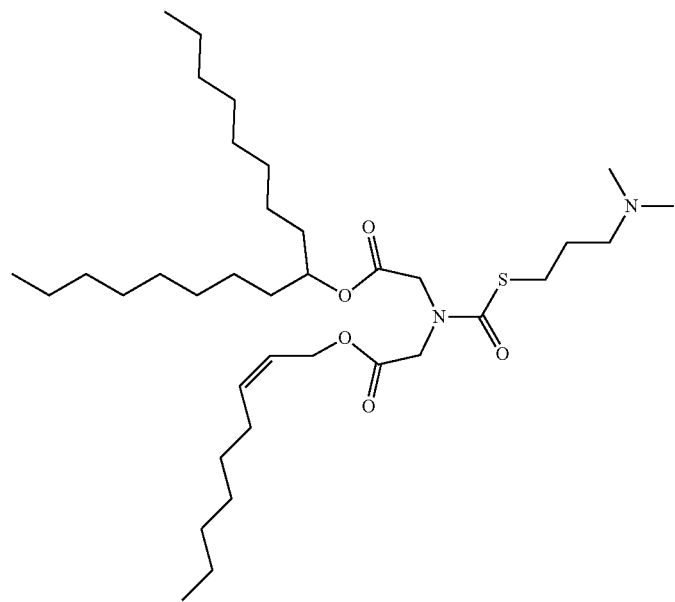
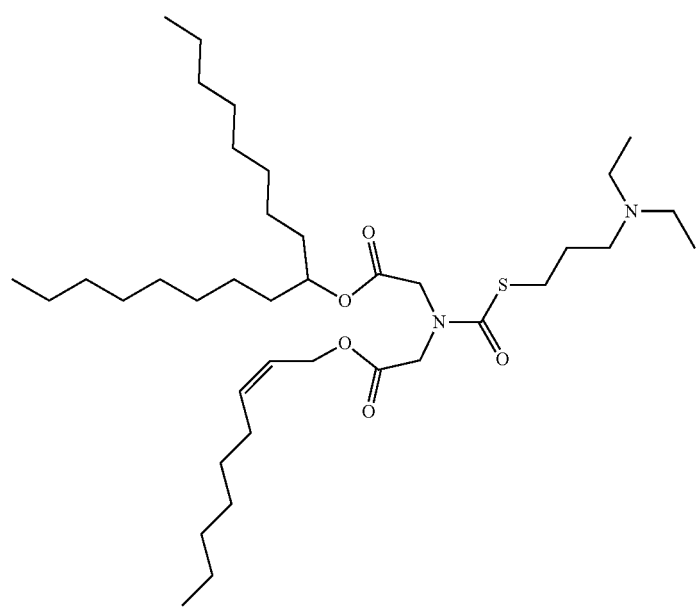

-continued
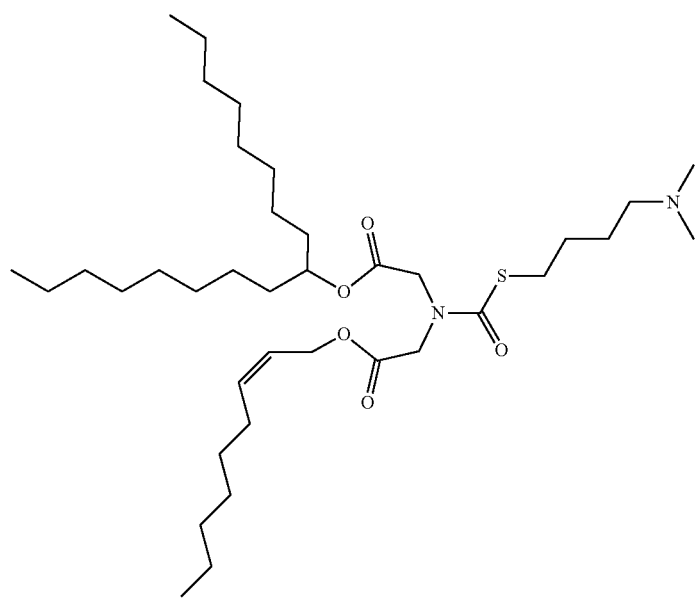
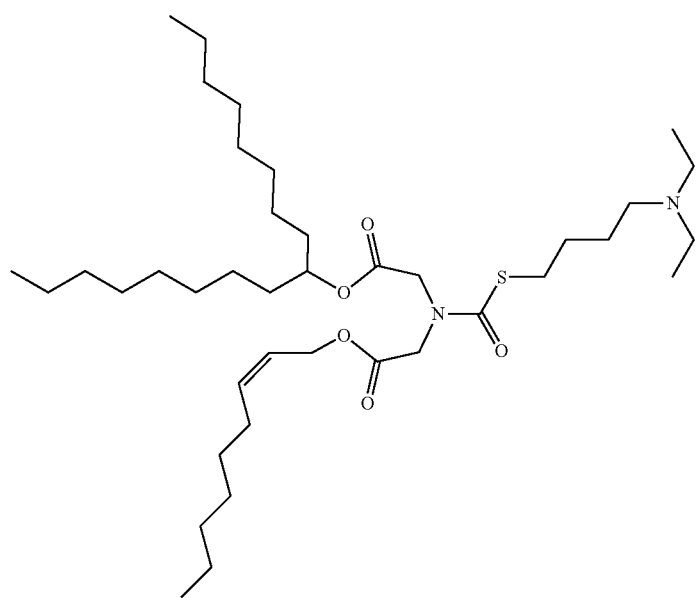

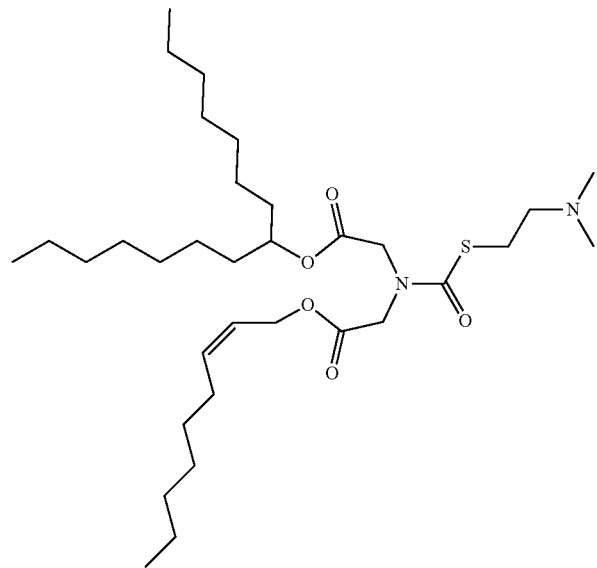
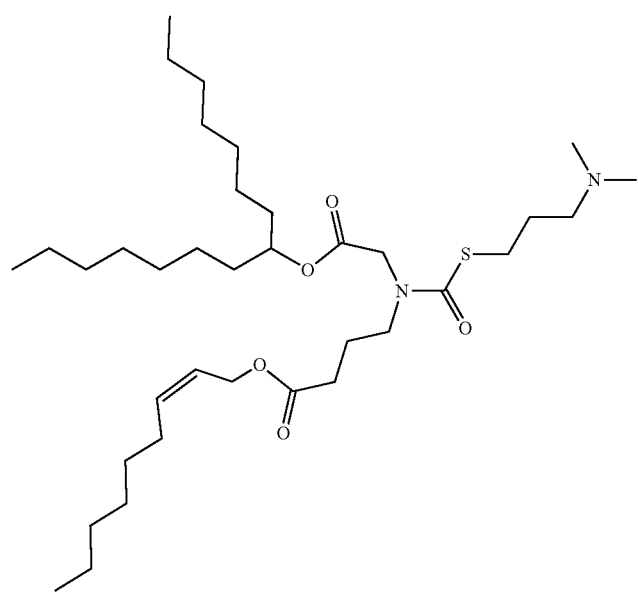

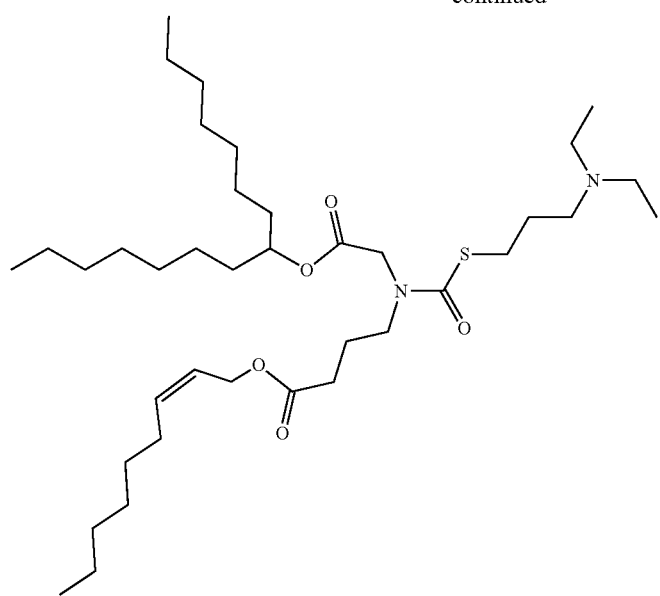
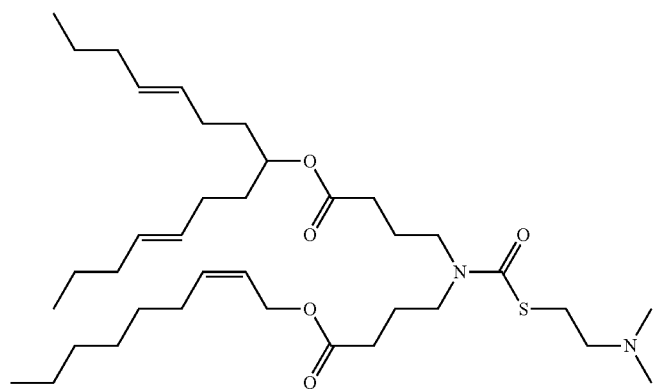
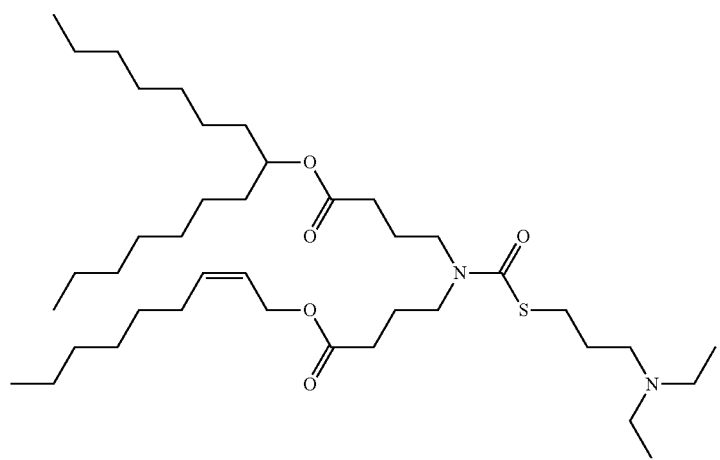

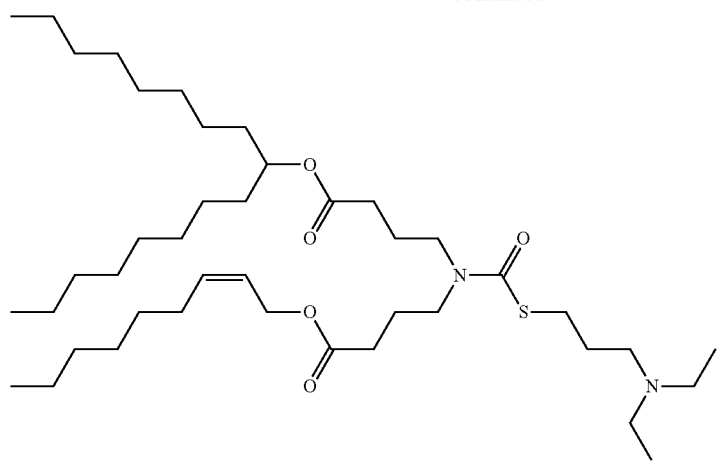
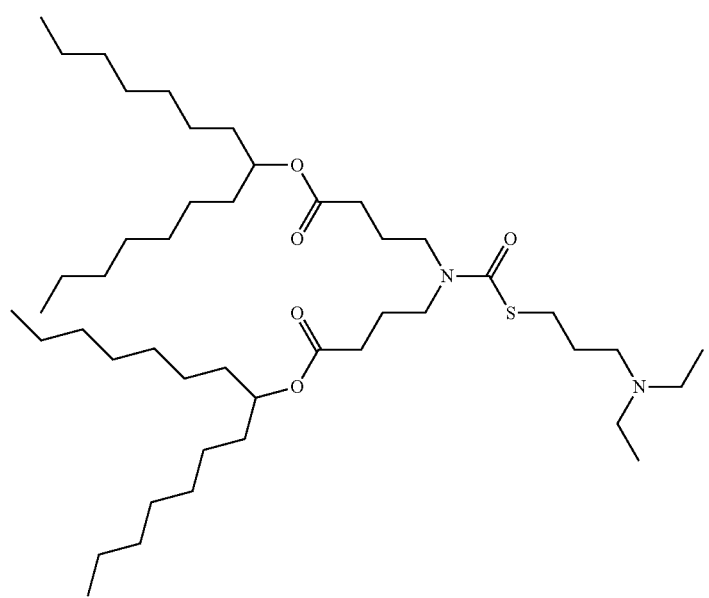
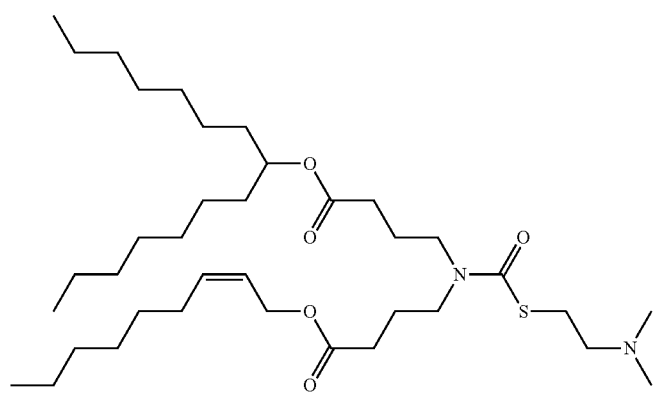

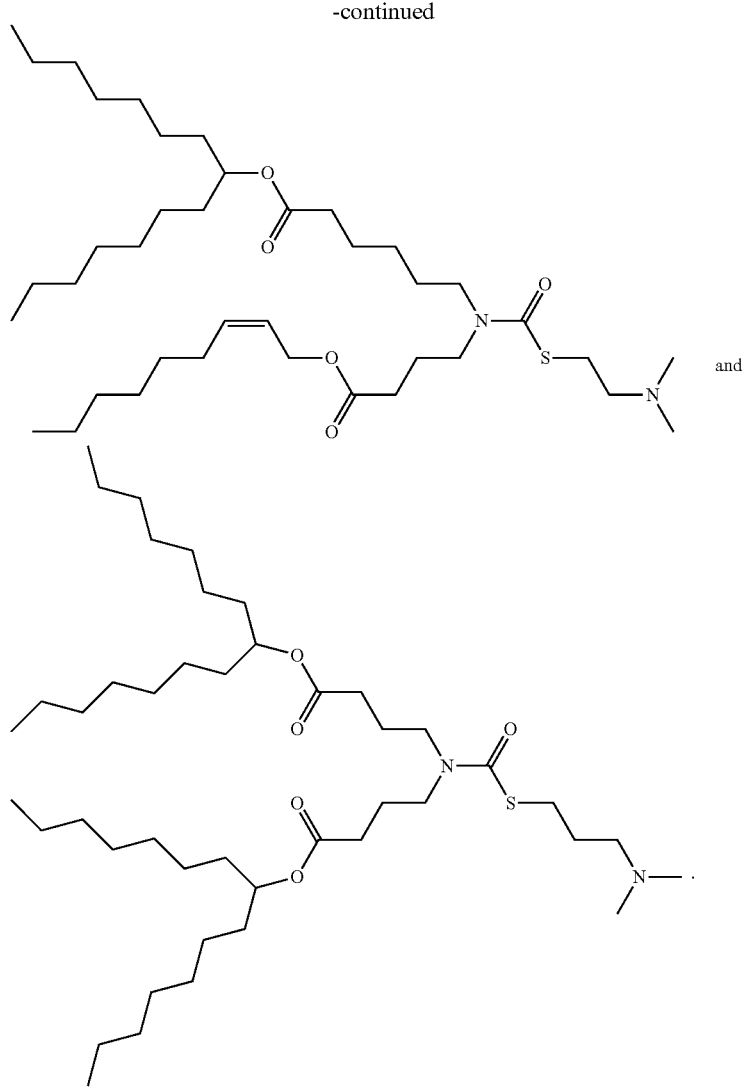

and

In some embodiments, any one or more lipids recited herein may be expressly excluded.

Helper Lipids and Sterols

The mRNA-lipid formulations of the present disclosure can comprise a helper lipid, which can be referred to as a neutral lipid, a neutral helper lipid, non-cationic lipid, non-cationic helper lipid, anionic lipid, anionic helper lipid, or a zwitterionic lipid. It has been found that lipid formulations, particularly cationic liposomes and lipid nanoparticles have increased cellular uptake if helper lipids are present in the formulation. (Curr. Drug Metab. 2014; 15(9):882-92). For example, some studies have indicated that neutral and zwitterionic lipids such as 1,2-dioleoyl-sn-glycero-3-phosphatidylcholine (DOPC), Di-Oleoyl-Phosphatidyl-Ethanoalamine (DOPE) and 1,2-DiStearoyl-sn-glycero-3-PhosphoCholine (DSPC), being more fusogenic (i.e., facilitating fusion) than cationic lipids, can affect the polymorphic features of lipid-nucleic acid complexes, promoting the transition from a lamellar to a hexagonal phase, and thus inducing fusion and a disruption of the cellular membrane. (Nanomedicine (Lond). 2014 January; 9(1):105-20). In addition, the use of helper lipids can help to reduce any potential detrimental effects from using many prevalent cationic lipids such as toxicity and immunogenicity.

Non-limiting examples of non-cationic lipids suitable for lipid formulations of the present disclosure include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, di stearoylphosphatidylcholine (DSPC), diol eoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleoyl-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having $C_{10}$-$C_{24}$ carbon chains, e.g., lauroyl, myristoyl, palmitoyl, stearoyl, or oleoyl.

Additional examples of non-cationic lipids include sterols such as cholesterol and derivatives thereof. One study concluded that as a helper lipid, cholesterol increases the spacing of the charges of the lipid layer interfacing with the nucleic acid making the charge distribution match that of the nucleic acid more closely. (J. R. Soc. Interface. 2012 Mar 7; 9(68): 548-561). Non-limiting examples of cholesterol derivatives include polar analogues such as 5α-cholestanol, 5α-coprostanol, cholesteryl-(2'-hydroxy)-ethyl ether, cholesteryl-(4'-hydroxy)-butyl ether, and 6-ketocholestanol; non-polar analogues such as 5α-cholestane, cholestenone, 5α-cholestanone, 5α-cholestanone, and cholesteryl decanoate; and mixtures thereof. In preferred embodiments, the cholesterol derivative is a polar analogue such as cholesteryl-(4'-hydroxy)-butyl ether.

In some embodiments, the helper lipid present in the lipid formulation comprises or consists of a mixture of one or more phospholipids and cholesterol or a derivative thereof. In other embodiments, the helper lipid present in the lipid formulation comprises or consists of one or more phospholipids, e.g., a cholesterol-free lipid formulation. In yet other embodiments, the helper lipid present in the lipid formulation comprises or consists of cholesterol or a derivative thereof, e.g., a phospholipid-free lipid formulation.

Other examples of helper lipids include nonphosphorous containing lipids such as, e.g., stearylamine, dodecylamine, hexadecylamine, acetyl palmitate, glycerol ricinoleate, hexadecyl stearate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, and sphingomyelin.

In some embodiments, the helper lipid comprises from about 20 mol % to about 50 mol %, from about 22 mol % to about 48 mol %, from about 24 mol % to about 46 mol %, about 25 mol % to about 44 mol %, from about 26 mol % to about 42 mol %, from about 27 mol % to about 41 mol %, from about 28 mol % to about 40 mol %, or about 29 mol %, about 30 mol %, about 31 mol %, about 32 mol %, about 33 mol %, about 34 mol %, about 35 mol %, about 36 mol %, about 37 mol %, about 38 mol %, or about 39 mol % (or any fraction thereof or the range therein) of the total lipid present in the lipid formulation.

In some embodiments, the total of helper lipid in the formulation comprises two or more helper lipids and the total amount of helper lipid comprises from about 20 mol % to about 50 mol %, from about 22 mol % to about 48 mol %, from about 24 mol % to about 46 mol %, about 25 mol % to about 44 mol %, from about 26 mol % to about 42 mol %, from about 27 mol % to about 41 mol %, from about 28 mol % to about 40 mol %, or about 29 mol %, about 30 mol %, about 31 mol %, about 32 mol %, about 33 mol %, about 34 mol %, about 35 mol %, about 36 mol %, about 37 mol %, about 38 mol %, or about 39 mol % (or any fraction thereof or the range therein) of the total lipid present in the lipid formulation. In some embodiments, the helper lipids are a combination of DSPC and DOTAP. In some embodiments, the helper lipids are a combination of DSPC and DOTMA.

The cholesterol or cholesterol derivative in the lipid formulation may comprise up to about 40 mol %, about 45 mol %, about 50 mol %, about 55 mol %, or about 60 mol % of the total lipid present in the lipid formulation. In some embodiments, the cholesterol or cholesterol derivative comprises about 15 mol % to about 45 mol %, about 20 mol % to about 40 mol %, about 30 mol % to about 40 mol %, or about 35 mol %, about 36 mol %, about 37 mol %, about 38 mol %, about 39 mol %, or about 40 mol % of the total lipid present in the lipid formulation.

The percentage of helper lipid present in the lipid formulation is a target amount, and the actual amount of helper lipid present in the formulation may vary, for example, by ±5 mol %.

A lipid formulation containing a cationic lipid compound or ionizable cationic lipid compound may be on a molar basis about 20-40% cationic lipid compound, about 25-40% cholesterol, about 25-50% helper lipid, and about 0.5-5% of a polyethylene glycol (PEG) lipid, wherein the percent is of the total lipid present in the formulation. In some embodiments, the composition is about 22-30% cationic lipid compound, about 30-40% cholesterol, about 30-40% helper lipid, and about 0.5-3% of a PEG-lipid, wherein the percent is of the total lipid present in the formulation.

Lipid Conjugates

The lipid formulations described herein may further comprise a lipid conjugate. The conjugated lipid is useful for preventing the aggregation of particles. Suitable conjugated lipids include, but are not limited to, PEG-lipid conjugates, cationic-polymer-lipid conjugates, and mixtures thereof. Furthermore, lipid delivery vehicles can be used for specific targeting by attaching ligands (e.g., antibodies, peptides, and carbohydrates) to its surface or to the terminal end of the attached PEG chains (Front. Pharmacol. 2015 Dec. 1; 6:286).

In a preferred embodiment, the lipid conjugate is a PEG-lipid. The inclusion of polyethylene glycol (PEG) in a lipid formulation as a coating or surface ligand, a technique referred to as PEGylation, helps protect nanoparticles from the immune system and their escape from RES uptake (Nanomedicine (Lond). 2011 June; 6(4):715-28). PEGylation has been widely used to stabilize lipid formulations and their payloads through physical, chemical, and biological mechanisms. Detergent-like PEG lipids (e.g., PEG-DSPE) can enter the lipid formulation to form a hydrated layer and steric barrier on the surface. Based on the degree of PEGylation, the surface layer can be generally divided into two types, brush-like and mushroom-like layers. For PEG-DSPE-stabilized formulations, PEG will take on the mushroom conformation at a low degree of PEGylation (usually less than 5 mol %) and will shift to brush conformation as the content of PEG-DSPE is increased past a certain level (J. Nanomaterials. 2011; 2011:12). It has been shown that increased PEGylation leads to a significant increase in the circulation half-life of lipid formulations (Annu. Rev. Biomed. Eng. 2011 Aug. 15; 130:507-30; J. Control Release. 2010 Aug. 3; 145(3): 178-81).

Suitable examples of PEG-lipids include, but are not limited to, PEG coupled to dialkyloxypropyls (PEG-DAA), PEG coupled to diacylglycerol (PEG-DAG), PEG coupled to phospholipids such as phosphatidylethanolamine (PEG-PE), PEG conjugated to ceramides, PEG conjugated to cholesterol or a derivative thereof, and mixtures thereof.

PEG is a linear, water-soluble polymer of ethylene PEG repeating units with two terminal hydroxyl groups. PEGs are classified by their molecular weights and include the following: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH$_2$), monomethoxypolyethylene glycol-tresylate (MePEG-TRES), monomethoxypolyethylene glycol-imidazolyl-carbonyl (MePEG-IM), as well as such compounds containing a terminal hydroxyl group instead of a terminal methoxy group (e.g., HO-PEG-S, HO-PEG-S-NHS, HO-PEG-NH$_2$).

The PEG moiety of the PEG-lipid conjugates described herein may comprise an average molecular weight ranging from about 550 daltons to about 10,000 daltons. In certain instances, the PEG moiety has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons). In preferred embodiments, the PEG moiety has an average molecular weight of about 2,000 daltons or about 750 daltons. The average molecular weight may be any value or subvalue within the recited ranges, including endpoints.

In certain instances, the PEG monomers can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester-containing linker moieties and ester-containing linker moieties. In a preferred embodiment, the linker moiety is a non-ester-containing linker moiety. Suitable non-ester-containing linker moieties include, but are not limited to, amido (—C(O)NH—), amino (—NR—), carbonyl (—C(O)—), carbamate (—NHC(O)O—), urea (—NHC(O)NH—), disulfide (—S—S—), ether (—O—), succinyl (—(O)CCH$_2$CH$_2$C(O)—), succinamidyl (—NHC(O)CH$_2$CH$_2$C(O)NH—), ether, as well as combinations thereof (such as a linker containing both a carbamate linker moiety and an amido linker moiety). In a preferred embodiment, a carbamate linker is used to couple the PEG to the lipid.

In other embodiments, an ester-containing linker moiety is used to couple the PEG to the lipid. Suitable ester-containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form the lipid conjugate. Such phosphatidylethanolamines are commercially available or can be isolated or synthesized using conventional techniques known to those of skill in the art. Phosphatidylethanolamines containing saturated or unsaturated fatty acids with carbon chain lengths in the range of $C_{10}$ to $C_{20}$ are preferred. Phosphatidylethanolamines with mono- or di-unsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoyl-phosphatidylethanolamine (DOPE), and distearoyl-phosphatidylethanolamine (DSPE).

In some embodiments, the PEG-DAA conjugate is a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, or a PEG-distearyloxypropyl ($C_{18}$) conjugate. In these embodiments, the PEG preferably has an average molecular weight of about 750 to about 2,000 daltons. In particular embodiments, the terminal hydroxyl group of the PEG is substituted with a methyl group.

In addition to the foregoing, other hydrophilic polymers can be used in place of PEG. Examples of suitable polymers that can be used in place of PEG include, but are not limited to, polyvinylpyrroli done, polymethyloxazoline, polyethyloxazoline, polyhydroxypropyl, methacrylamide, polymethacrylamide, and polydimethylacrylamide, polylactic acid, polyglycolic acid, and derivatized celluloses such as hydroxymethylcellulose or hydroxyethylcellulose.

In some embodiments, the lipid conjugate (e.g., PEG-lipid) comprises from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 0.9 mol % to about 1.6 mol %, from about 0.9 mol % to about 1.8 mol %, from about 1 mol % to about 1.8 mol %, from about 1 mol % to about 1.7 mol %, from about 1.2 mol % to about 1.8 mol %, from about 1.2 mol % to about 1.7 mol %, from about 1.3 mol % to about 1.6 mol %, or from about 1.4 mol % to about 1.6 mol % (or any fraction thereof or range therein) of the total lipid present in the lipid formulation. In other embodiments, the lipid conjugate (e.g., PEG-lipid) comprises about 0.5%, 0.6%, 0.7%, 0.8%, 0.9%, 1.0%, 1.2%, 1.3%, 1.4%, 1.5%, 1.6%, 1.7%, 1.8%, 1.9%, 2.0%, 2.5%, 3.0%, 3.5%, 4.0%, 4.5%, or 5%, (or any fraction thereof or range therein) of the total lipid present in the lipid formulation. The amount may be any value or subvalue within the recited ranges, including endpoints.

In some preferred embodiments, the PEG-lipid is PEG550-PE. In some preferred embodiments, the PEG-lipid is PEG750-PE. In some preferred embodiments, the PEG-lipid is PEG2000-DMG The percentage of lipid conjugate (e.g., PEG-lipid) present in the lipid formulations of the disclosure is a target amount, and the actual amount of lipid conjugate present in the formulation may vary, for example, by ±0.5 mol %. One of ordinary skill in the art will appreciate that the concentration of the lipid conjugate can be varied depending on the lipid conjugate employed and the rate at which the lipid formulation is to become fusogenic.

Mechanism of Action for Cellular Uptake of Lipid Formulations

Lipid formulations for the intracellular delivery of nucleic acids, particularly liposomes, cationic liposomes, and lipid nanoparticles, are designed for cellular uptake by penetrating target cells through exploitation of the target cells' endocytic mechanisms where the contents of the lipid delivery vehicle are delivered to the cytosol of the target cell. (Nucleic Acid Therapeutics, 28(3):146-157, 2018). Specifically, in the case of a mRNA-lipid formulation targeting hepatocytes described herein, the mRNA-lipid formulation enters hepatocytes through receptor mediated endocytosis. Prior to endocytosis, functionalized ligands such as PEG-lipid at the surface of the lipid delivery vehicle are shed from the surface, which triggers internalization into the target cell. During endocytosis, some part of the plasma membrane of the cell surrounds the vector and engulfs it into a vesicle that then pinches off from the cell membrane, enters the cytosol and ultimately undergoes the endolysosomal pathway. For ionizable cationic lipid-containing delivery vehicles, the increased acidity as the endosome ages results in a vehicle with a strong positive charge on the surface. Interactions between the delivery vehicle and the endosomal membrane then result in a membrane fusion event that leads to cytosolic delivery of the payload. For mRNA payloads, the cell's own internal translation processes will then translate the mRNA into the encoded protein. The encoded protein can further undergo post-translational processing, including transportation to a targeted organelle or location within the cell.

By controlling the composition and concentration of the lipid conjugate, one can control the rate at which the lipid conjugate exchanges out of the lipid formulation and, in turn, the rate at which the lipid formulation becomes fusogenic. In addition, other variables including, e.g., pH, temperature, or ionic strength, can be used to vary and/or control the rate at which the lipid formulation becomes fusogenic. Other methods which can be used to control the rate at which the lipid formulation becomes fusogenic will become apparent to those of skill in the art upon reading this disclosure. Also, by controlling the composition and concentration of the lipid conjugate, one can control the liposomal or lipid particle size.

Lipid Formulation Manufacture

There are many different methods for the preparation of lipid formulations comprising a nucleic acid. (Curr. Drug Metabol. 2014, 15, 882-892; Chem. Phys. Lipids 2014, 177, 8-18; Int. J. Pharm. Stud. Res. 2012, 3, 14-20). The techniques of thin film hydration, double emulsion, reverse phase evaporation, microfluidic preparation, dual asymmetric centrifugation, ethanol injection, detergent dialysis, spontaneous vesicle formation by ethanol dilution, and encapsulation in preformed liposomes are briefly described herein.

Thin Film Hydration

In Thin Film Hydration (TFH) or the Bangham method, the lipids are dissolved in an organic solvent, then evaporated through the use of a rotary evaporator leading to a thin lipid layer formation. After the layer hydration by an aqueous buffer solution containing the compound to be loaded, Multilamellar Vesicles (MLVs) are formed, which can be reduced in size to produce Small or Large Unilamellar vesicles (LUV and SUV) by extrusion through membranes or by the sonication of the starting MLV.

Double Emulsion

Lipid formulations can also be prepared through the Double Emulsion technique, which involves lipids dissolution in a water/organic solvent mixture. The organic solution, containing water droplets, is mixed with an excess of aqueous medium, leading to a water-in-oil-in-water (W/O/W) double emulsion formation. After mechanical vigorous shaking, part of the water droplets collapse, giving Large Unilamellar Vesicles (LUVs).

Reverse Phase Evaporation

The Reverse Phase Evaporation (REV) method also allows one to achieve LUVs loaded with nucleic acid. In this technique a two-phase system is formed by phospholipids dissolution in organic solvents and aqueous buffer. The resulting suspension is then sonicated briefly until the mixture becomes a clear one-phase dispersion. The lipid formulation is achieved after the organic solvent evaporation under reduced pressure. This technique has been used to encapsulate different large and small hydrophilic molecules including nucleic acids.

Microfluidic Preparation

The Microfluidic method, unlike other bulk techniques, gives the possibility of controlling the lipid hydration process. The method can be classified in continuous-flow microfluidic and droplet-based microfluidic, according to the way in which the flow is manipulated. In the microfluidic hydrodynamic focusing (MHF) method, which operates in a continuous flow mode, lipids are dissolved in isopropyl alcohol which is hydrodynamically focused in a microchannel cross junction between two aqueous buffer streams. Vesicles size can be controlled by modulating the flow rates, thus controlling the lipids solution/buffer dilution process. The method can be used for producing oligonucleotide (ON) lipid formulations by using a microfluidic device consisting of three-inlet and one-outlet ports.

Dual Asymmetric Centrifugation

Dual Asymmetric Centrifugation (DAC) differs from more common centrifugation as it uses an additional rotation around its own vertical axis. An efficient homogenization is achieved due to the two overlaying movements generated: the sample is pushed outwards, as in a normal centrifuge, and then it is pushed towards the center of the vial due to the additional rotation. By mixing lipids and an NaCl-solution a viscous vesicular phospholipid gel (VPC) is achieved, which is then diluted to obtain a lipid formulation dispersion. The lipid formulation size can be regulated by optimizing DAC speed, lipid concentration and homogenization time.

Ethanol Injection

The Ethanol Injection (EI) method can be used for nucleic acid encapsulation. This method provides the rapid injection of an ethanolic solution, in which lipids are dissolved, into an aqueous medium containing nucleic acids to be encapsulated, through the use of a needle. Vesicles are spontaneously formed when the phospholipids are dispersed throughout the medium.

Detergent Dialysis

The Detergent dialysis method can be used to encapsulate nucleic acids. Briefly lipid and plasmid are solubilized in a detergent solution of appropriate ionic strength, after removing the detergent by dialysis, a stabilized lipid formulation is formed. Unencapsulated nucleic acid is then removed by ion-exchange chromatography and empty vesicles by sucrose density gradient centrifugation. The technique is highly sensitive to the cationic lipid content and to the salt concentration of the dialysis buffer, and the method is also difficult to scale.

Spontaneous Vesicle Formation by Ethanol Dilution

Stable lipid formulations can also be produced through the Spontaneous Vesicle Formation by Ethanol Dilution method in which a stepwise or dropwise ethanol dilution provides the instantaneous formation of vesicles loaded with nucleic acid by the controlled addition of lipid dissolved in ethanol to a rapidly mixing aqueous buffer containing the nucleic acid.

Encapsulation in Preformed Liposomes

The entrapment of nucleic acids can also be obtained starting with preformed liposomes through two different methods: (1) a simple mixing of cationic liposomes with nucleic acids which gives electrostatic complexes called "lipoplexes", where they can be successfully used to transfect cell cultures, but are characterized by their low encapsulation efficiency and poor performance in vivo; and (2) a liposomal destabilization, slowly adding absolute ethanol to a suspension of cationic vesicles up to a concentration of 40% v/v followed by the dropwise addition of nucleic acids achieving loaded vesicles; however, the two main steps characterizing the encapsulation process are too sensitive, and the particles have to be downsized.

Lipid-Encapsulated RNA Nanoparticle Formation

FIG. 1 provides an example of a representative flow chart of a general method described herein of producing lipid-encapsulated RNA nanoparticles.

The geometry of the mixing layer consists of a first tube for transporting the aqueous solution having an inner diameter as described herein; and a second tube for transporting the ethanol (organic) solution consisting of a ID as described herein; when a mixinb module as described herein is used the second (organic) tube intersects the first (aqueous) tube at or near a perpendicular angle.

The method described herein provides an aqueous RNA solution comprising a therapeutic large RNA, e.g., prepared under Good Manufacturing Practice (GMP), solubilized in an aqueous solution comprising a buffer, e.g., citrate. The present method also provides an organic solution comprising one or more lipids, e.g., clinical grade lipids synthesized under GMP, produced by solubilizing lipid in a water-miscible organic solvent. In the method described herein, the water-miscible organic solvent, preferably is a lower alkanol, e.g., ethanol. Preferably, both solutions are filter sterilized and their concentrations are adjusted.

The organic lipid solution is mixed with the aqueous solution comprising a nucleic acid to form a lipid-encapsulated RNA nanoparticle having a lamellar morphology, i.e., including a lipid bilayer. In one aspect, the nucleic acid is encapsulated in the lipid-encapsulated RNA nanoparticles with formation of the lamellar structure.

The method described herein is directed to continuously introducing a lipid solution into the aqueous solution in a mixing environment, preferably perpendicularly in a mixing module. The mixing dilutes the lipid solution with the aqueous solution to 10% to 75% v/v ethanol, 12% to 70% v/v ethanol, 14% to 65% v/v ethanol, 16% to 60% v/v ethanol, 18% to 50% v/v ethanol, 20% to 45% v/v ethanol, or 22% to 30% v/v ethanol, and causes formation of lipid-encapsulated RNA nanoparticles in a turbulent flow.

After formation of the lipid-encapsulated RNA nanoparticles, the mixture is continuously diluted by a buffer to about 1 to about 10% v/v ethanol, or 7.5%, 10%, 12.5%, or 15%, preferably to less than 12.5% ethanol, which further stabilizes the lipid-encapsulated RNA nanoparticles and increases encapsulation of nucleic acid.

The lipid-encapsulated RNA nanoparticles are concentrated by tangential flow filtration, preferably by hollow fiber filters. The concentrated lipid-encapsulated RNA nanoparticles are subjected to an ultrafiltration step to remove the alkanol and substitute the buffer. The nucleic acid concentration is adjusted by dilution. The resulting formulation is filter sterilized and filled in vials. The process will now be discussed in more detail herein below using the steps as set forth in FIG. 1.

Lipid Solubilization and RNA Dissolution

In one embodiment, the lipid-encapsulated RNA nanoparticles produced by the method described herein are in the form of multimolecular assemblies of RNA and lipids, in which the RNA is encapsulated at least in part by ionic pairing with cationic lipids.

In certain aspects, the lipid nanoparticles of the description herein include four lipid components: a helper lipid; cholesterol; a PEG-lipid; and a cationic lipid. Preferably, the helper lipid is DSPC, the PEG-lipid is PEG-DMG, and the cationic lipid is an ionizable cationic lipid. In certain embodiments, the organic solvent concentration in which the lipids are solubilized is about 45% v/v to about 90% v/v. In certain preferred aspects, the organic solvent is a lower alkanol. Suitable lower alkanols include, e.g., methanol, ethanol, propanol, butanol, pentanol, their isomers and combinations thereof. The solvent is preferably ethanol with a concentration of about 50-90% v/v. The lipids may occupy a volume of about 1 mL/g to about 5 mL/g or as otherwise described in the examples below.

The lipids are solubilized using for example, an overhead stirrer at a suitable temperature.In certain preferred aspects, the RNA is included in an aqueous solution (e.g., buffer) and is diluted to a final concentration.

Lipid-Encapsulated RNA Nanoparticle Formation Step

After the organic solution and the aqueous solutions are prepared, they can be mixed together using the apparatus described in detail below. Briefly, the apparatus consists of a first tube for transporting the aqueous RNA solution and a second tube for transporting the organic lipid solution, in which the second tube intersects the first tube perpendicularly within the mixing module. The two solutions are pumped through the respective tubes by separate HPLC pumps and mixed in the region of the first tube perpendicularly within the mixing module. The aqueous RNA solution is pumped at a rate that is 0.2 to 1 times greater than the organic lipid solution. Upon mixing the two solutions in the mixing area, lipid-encapsulated RNA nanoparticles are formed.

The pump speeds and the size of the first tube in the region of the mixing module provides for a mixing process that involves turbulent flow. In fluid dynamics, turbulence or turbulent flow is fluid motion characterized by chaotic changes in pressure and flow velocity. It is in contrast to a laminar flow, which occurs when a fluid flows in parallel layers, with no disruption between those layers. Turbulent flows are always highly irregular, and the readily available supply of energy in turbulent flows tends to accelerate the homogenization (mixing) of fluid mixtures. The characteristic which is responsible for the enhanced mixing and increased rates of mass, momentum and energy transports in a flow is called "diffusivity". Other characteristics of a turbulent flow include "rotationality" as turbulent flows have a strong three-dimensional vortex generation mechanism known as vortex stretching and "dissipation" as turbulence dissipates rapidly as the kinetic energy is converted into internal energy by viscous shear stress. Turbulent mixing is dominated by small scale (compared to the parent flow) random movements of parcels within a fluid that bring them into closer or more distant relationship and may more finely divide and intermingle them. The processes described herein for mixing of the lipid solution and the aqueous solution provides for encapsulation of RNA in the lipid nanoparticles formed coincident with their formation with an encapsulation efficiency of greater than 95%.

The continuous process described herein is fully scalable. In one aspect, lipid-encapsulated RNA nanoparticles are formed having a mean diameter of less than about 90 nm, without mechanical-energy processes such as membrane extrusion, sonication or microfluidization.

Lipid-Encapsulated RNA Nanoparticles

The lipid-encapsulated RNA nanoparticles disclosed herein comprise a nanoparticle or a bilayer of lipid molecules. In addition to the cationic lipid (e.g., an ionizable cationic lipid), the lipid-encapsulated RNA nanoparticle comprises a neutral lipid or a polymer.

In some embodiments, the RNA is fully encapsulated within the lipid portion of the lipid nanoparticle such that the RNA in the lipid-encapsulated RNA nanoparticles is resistant in aqueous solution to nuclease degradation. In other embodiments, the lipid-encapsulated RNA nanoparticles described herein are substantially non-toxic to mammals such as humans. The lipid-encapsulated RNA nanoparticles typically have a mean diameter of from 30 nm to 150 nm, from 40 nm to 150 nm, from 50 nm to 150 nm, from 60 nm to 130 nm, from 70 nm to 110 nm, or from 70 to 90 nm. The lipid-encapsulated RNA nanoparticles described herein also typically have a lipid:RNA ratio (mass/mass ratio) of from 1:1 to 100:1, from 1:1 to 50:1, from 5:1 to 45:1, from 10:1 to 40:1, from 12:1 to 38:1, or from 15:1 to 45:1, or from 25:1 to 40:1, or from 30:1 to 40:1. In some embodiments, the composition has a total lipid:RNA weight ratio of between about 50:1 and 10:1. In some embodiments, the composition has a total lipid:RNA weight ratio of between about 40:1 and 20:1. In some embodiments, the composition has a total lipid:RNA weight ratio of between about 45:1 and 30:1. In some embodiments, the composition has a total lipid:RNA weight ratio of between about 38:1 and 30:1.

In preferred embodiments, the lipid particles comprise an RNA, a cationic lipid (e.g., one or more cationic lipids or salts thereof described herein), a phospholipid, and a conjugated lipid that inhibits aggregation of the particles (e.g., one or more PEG-lipid conjugates). The lipid-encapsulated RNA nanoparticles can also include cholesterol. The lipid-encapsulated RNA nanoparticles may comprise at least 1, 2, 3, 4, 5, 6, 7, 8, 9, 10, or more different RNA that express one or more polypeptides.

In the lipid-encapsulated RNA nanoparticles the RNA may be fully encapsulated within the lipid portion of the particle, thereby protecting the RNA from nuclease degradation. In preferred embodiments, the lipid-encapsulated RNA nanoparticles comprise an RNA that is fully encapsulated within the lipid portion of the particle, thereby protecting the RNA from nuclease degradation. In certain instances, the RNA in the lipid particle is not substantially degraded after exposure of the particle to a nuclease at 37° C. for at least 20, 30, 45, or 60 minutes. In certain other instances, the RNA in the lipid particle is not substantially degraded after incubation of the particle in serum at 37° C. for at least 30, 45, or 60 minutes or at least 2, 3, 4, 5, 6, 7, 8, 9, 10, 12, 14, 16, 18, 20, 22, 24, 26, 28, 30, 32, 34, or 36 hours. In other embodiments, the RNA is complexed with the cationic lipid of the lipid-encapsulated RNA nanoparticles. One of the benefits of the formulations of the present disclosure is that the lipid-encapsulated RNA nanoparticles are substantially non-toxic to mammals such as humans.

The lipid particle comprises RNA that is fully encapsulated within the lipid portion of the particles, such that from 30% to 100%, from 40% to 100%, from 50% to 100%, from 60% to 100%, from 70% to 100%, from 80% to 100%, from 90% to 100%, from 30% to 95%, from 40% to 95%, from 50% to 95%, from 60% to 95%, from 70% to 95%, from 80% to 95%, from 85% to 95%, from 90% to 95%, from 30% to 90%, from 40% to 90%, from 50% to 90%, from 60% to 90%, from 70% to 90%, from 80% to 90%, or at least 30%, 35%, 40%, 45%, 50%, 55%, 60%, 65%, 70%, 75%, 80%, 85%, 90%, 91%, 92%, 93%, 94%, 95%, 96%, 97%, 98%, or 99% (or any fraction thereof or range therein) of the particles have the RNA encapsulated therein.

Depending on the intended use of the lipid-encapsulated RNA nanoparticles, the proportions of the components can be varied and the delivery efficiency of a particular formulation can be measured using assays know in the art.

Dilution of the Lipid-Encapsulated RNA Nanoparticles

After mixing the organic lipid solution into the aqueous RNA solution, the extent of RNA encapsulation can be enhanced if the suspension of lipid-encapsulated RNA nanoparticles is further diluted prior to removal of free RNA. This can be done via one or more buffer dilutions, for example, via one or more Y-connectors that flow into the output line. The buffers flowing into the one or more Y-connectors do not have to be the same.

The diluted lipid-encapsulated RNA nanoparticles can then be optionally collected in a vessel maintained at 15-20° C. and allowed to incubate from a few minutes to two hours prior to a further dilution step or a concentration step.

Sample Concentration

Diluted lipid-encapsulated RNA nanoparticles can be concentrated, e.g., by tangential flow filtration (TFF) using hollow fiber membranes (mPES Kros membranes, Spectrum Laboratories, Inc., Rancho Dominguez, Calif.), optionally via a peristaltic pump or a 4-piston-diaphragm pump or a centrifugal pump (based on principle of magnetic levitation). Methods for such concentration techniques are known in the art and would be readily apparent to a person of ordinary skill.

Removal of Free RNA and Buffer Replacement

Concentration can be followed by diafiltration against 7-10 volumes of 10 mM Tris, 50 mM NaCl, 9% sucrose, pH 7.5 to remove organic solvent and unbound RNA. Preferably, the diafiltration buffer is added via a heat exchanger such that product temperature is maintained at 15-20° C. The formulation can be further concentrated to target a total formulated RNA concentration of >3 mg/mL.

Sterile Filtration and Fill

The RNA concentration in the formulation of lipid-encapsulated RNA nanoparticles can then be measured by IPRP-HPLC (Ion Pair Reverse Phase-High Performance Liquid Chromatography) and adjusted to ~2 mg/mL (1.85 to 2.3 mg/mL) by diluting with a buffer as described hereinbelow optionally containing glycerol such that the final concentration of glycerol in the formulation is 5%. The diafiltered lipid-encapsulated RNA nanoparticles are sterile filtered through a 0.2 µm sterilizing grade filter (PES). The filtered formulation can then be aseptically filled into glass vials, stoppered, capped and placed at −20 or −70±5° C.

Apparatus

Figure 2:
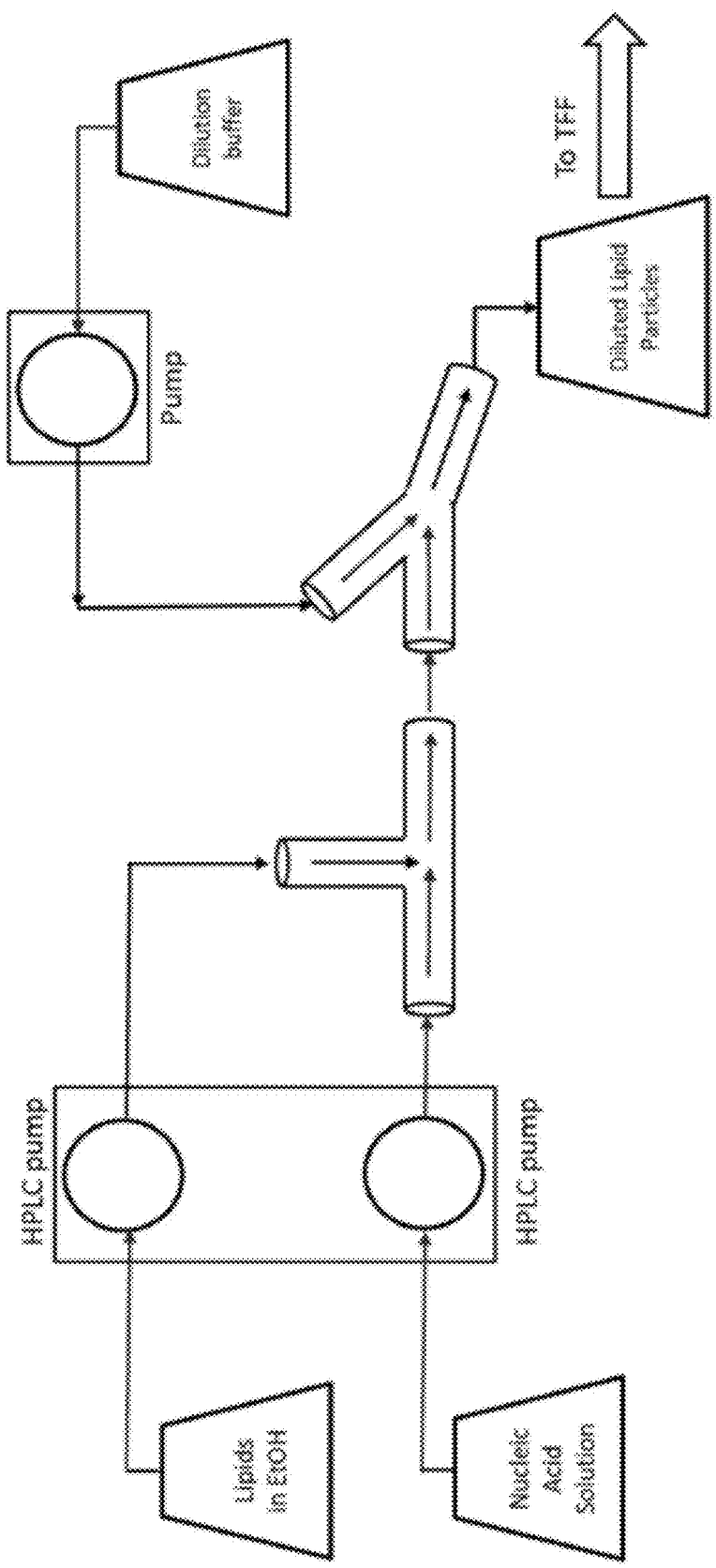
FIG. 2 shows an apparatus for producing lipid-encapsulated RNA nanoparticles. The aqueous solution comprising RNA is transported by an HPLC pump through tubing, and the organic solution comprising lipids is transported by an HPLC pump through separate tubing. The organic solution can be pumped into the aqueous solution at a 90 degree angle in the mixing area. The outlet tubing transports the mixed lipid-RNA outlet to a polypropylene tubing, which merges at a 45 degree angle with dilution buffer in the dilution area. The tubing which merges at a 45 degree angle with dilution buffer in the dilution area can be diluted in series to include 1, 2, 3 or 4 dilution areas of tubing each at a 45 degree angle for the dilution process. After the dilution process, the diluted particles can be collected in a stainless steel jacketed vessel maintained at 15-20° C. The particles are further processed by tangential flow filtration using a peristaltic, diaphragm or centrifugal pump.

The description herein provides an apparatus for carrying out the processes described above. FIG. 2 provides an example of a representative schematic of an apparatus according to one embodiment of the description herein.

The aqueous solution comprising RNA is transported by an HPLC pump through tubing. The organic solution comprising lipids is transported by an HPLC pump through separate tubing. The organic solution is pumped into the aqueous solution at a 90-degree angle in the mixing module. Thus, the organic solution comprising lipids is introduced into the aqueous solution with flow that is perpendicular to the flow of the aqueous solution. This introduction at right angles of flow direction occurs in a mixing module such as that illustrated in FIG. 3, and results in a turbulent mixing, under conditions that are carefully tuned to ensure that lipid nanoparticle encapsulation of the RNA is formed in an acceptable manner regarding particle size, dispersion, and encapsulation efficiency. The tubing containing the mixed lipid-RNA then transports the lipid-encapsulated RNA nanoparticles to a second mixing region, e.g., via polypropylene tubing which merges at a 45 degree angle with dilution buffer in the dilution area, and the diluted lipid-encapsulated RNA nanoparticles are collected in a stainless steel-jacketed vessel maintained at 15-20° C. The particles are further processed, e.g., by tangential flow filtration using a diaphragm or centrifugal pump.

The mixing area is in one embodiment, a mixing module in which the organic lipid solution is delivered into a stream of the aqueous RNA solution, preferably at an angle of about 90°. A first stainless steel tube transporting the aqueous RNA solution has a hole in its wall midway between its ends. A second tube is perpendicularly mounted by a filling through the hole in the wall of the first tube that allows transport of liquid from the second tube to the interior of the first tube (See FIG. 3). In preferred aspects, the lipid-encapsulated RNA nanoparticles' well-defined shape and reproducible size are prepared using a flow rate of the aqueous RNA solution that reduces shear forces and allows the integrity of the large RNA to be preserved. Vesicles having a well-defined shape and reproducible size are also prepared by changing the flow rate of the fluid lines, e.g., to ensure sufficient mixing in some cases.

Figure 3:
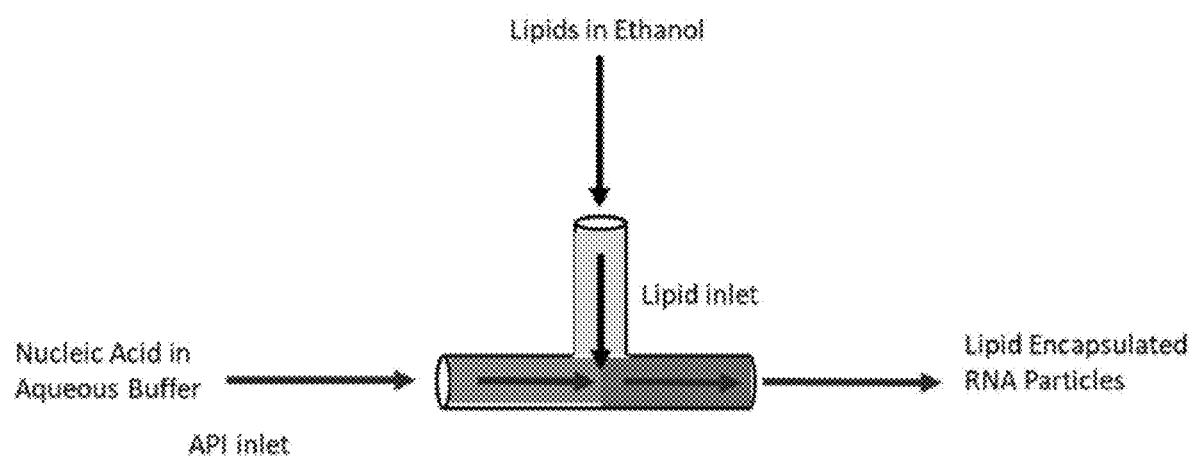
FIG. 3 shows the mixing module in more detail. The nucleic acids in buffer are transported through an input arm of a 1st stainless steel tube. The lipids in ethanol (or other suitable organic solvent/solvent mixture) are transported through a 2nd stainless steel tube that is perpendicularly attached to the 1st tube. A hole in the wall of the first tube allows transport of liquid from the 2nd tube to the interior of the 1st tube. Lipid-encapsulated RNA nanoparticles resulting from mixing exit through an output arm of the 1st tube.

FIG. 3 shows a mixing module and associated flow dynamics according to one embodiment.

The description herein provides an apparatus having tangential flow filtration using hollow fiber membranes (mPES Kros membranes, Spectrum Laboratories, Inc., Rancho Dominguez, Calif.) and 4-piston-diaphragm pumps or centrifugal pump.

DEFINITIONS

The term "anionic lipid" means a lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

The term "cationic lipid" means amphiphilic lipids and salts thereof having a positive, hydrophilic head group; one, two, three, or more hydrophobic fatty acid or fatty alkyl chains; and a connector between these two domains. An ionizable or protonatable cationic lipid is typically protonated (i.e., positively charged) at a pH below its $pK_a$ and is substantially neutral at a pH above the $pK_a$. Preferred ionizable cationic lipids are those having a pKa that is less than physiological pH, which is typically about 7.4. The cationic lipids of the disclosure may also be termed titratable cationic lipids. The cationic lipids can be an "amino lipid" having a protonatable tertiary amine (e.g., pH-titratable) head group. Some amino exemplary amino lipid can include $C_{18}$ alkyl chains, wherein each alkyl chain independently has 0 to 3 (e.g., 0, 1, 2, or 3) double bonds; and ether, ester, or ketal linkages between the head group and alkyl chains. Such cationic lipids include, but are not limited to, DSDMA, DODMA, DLinDMA, DLenDMA, γ-DLenDMA, DLin-K-DMA, DLin-K-C2-DMA (also known as DLin-C2K-DMA, XTC2, and C2K), DLin-K-C3-DM A, DLin-K-C4-DMA, DLen-C2K-DMA, y-DLen-C2K-DMA, DLin-M-C2-DMA (also known as MC2), DLin-M-C3-DMA (also known as MC3) and (DLin-MP-DMA)(also known as 1-B1 1).

The term "complementary nucleotide bases" means a pair of nucleotide bases that form hydrogen bonds with each other. Adenine (A) pairs with thymine (T) or with uracil (U) in RNA, and guanine (G) pairs with cytosine (C). Complementary segments or strands of nucleic acid that hybridize (i.e. join by hydrogen bonding) with each other. By "complementary" is meant that a nucleic acid can form hydrogen bond(s) with another nucleic acid sequence either by traditional Watson-Crick or by other non-traditional modes of binding.

The term "fully encapsulated" means that the nucleic acid (e.g., mRNA) in the nucleic acid-lipid particle is not significantly degraded after exposure to serum or a nuclease assay that would significantly degrade free RNA. When fully encapsulated, preferably less than 25% of the nucleic acid in the particle is degraded in a treatment that would normally degrade 100% of free nucleic acid, more preferably less than 10%, and most preferably less than 5% of the nucleic acid in the particle is degraded. "Fully encapsulated" also means that the nucleic acid-lipid particles do not rapidly decompose into their component parts upon in vivo administration.

The term "nucleic acid" means deoxyribonucleotides or ribonucleotides and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2'-O-methyl ribonucleotides, peptide-nucleic acids (PNAs).

The term "delivery" refers to the act or manner of delivering a compound, substance, entity, moiety, cargo or payload.

The term "delivery agent" refers to any substance which facilitates, at least in part, the in vivo delivery of a polynucleotide to targeted cells.

The term "engineered" refers to a molecule designed to have a feature or property, whether structural or chemical, that varies from a starting point, wild type or native molecule.

The term "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

The term "hydrophobic lipids" means compounds having apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N-N-dialkylamino, 1,2-diacyloxy-3-aminopropane, and 1,2-dialkyl-3-aminopropane.

The term "lipid" means an organic compound that comprises an ester of fatty acid and is characterized by being insoluble in water, but soluble in many organic solvents. Lipids are usually divided into at least three classes: (1) "simple lipids," which include fats and oils as well as waxes; (2) "compound lipids," which include phospholipids and glycolipids; and (3) "derived lipids" such as steroids.

The term "lipid delivery vehicle" means a lipid formulation that can be used to deliver a therapeutic nucleic acid (e.g., mRNA) to a target site of interest (e.g., cell, tissue, organ, and the like). The lipid delivery vehicle can be a nucleic acid-lipid particle, which can be formed from a cationic lipid, a non-cationic lipid (e.g., a phospholipid), a conjugated lipid that prevents aggregation of the particle (e.g., a PEG-lipid), and optionally cholesterol. Typically, the therapeutic nucleic acid (e.g., mRNA) may be encapsulated in the lipid portion of the particle, thereby protecting it from enzymatic degradation.

The term "lipid encapsulated" means a lipid particle that provides a therapeutic nucleic acid such as an mRNA with full encapsulation, partial encapsulation, or both. In a preferred embodiment, the nucleic acid (e.g., mRNA) is fully encapsulated in the lipid particle.

The term "lipid conjugate" means a conjugated lipid that inhibits aggregation of lipid particles. Such lipid conjugates include, but are not limited to, PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides, cationic PEG lipids, polyoxazoline (POZ)-lipid conjugates, polyamide oligomers, and mixtures thereof. PEG or POZ can be conjugated directly to the lipid or may be linked to the lipid via a linker moiety. Any linker moiety suitable for coupling the PEG or the POZ to a lipid can be used including, e.g., non-ester-containing linker moieties and ester-containing linker moieties. In certain preferred embodiments, non-ester-containing linker moieties, such as amides or carbamates, are used.

The term "amphipathic lipid" or "amphiphilic lipid" means the material in which the hydrophobic portion of the lipid material orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids, and sphingolipids.

The term "messenger RNA" (mRNA) refers to any polynucleotide which encodes a protein or polypeptide of interest and which is capable of being translated to produce the encoded protein or polypeptide of interest in vitro, in vivo, in situ or ex vivo.

The term "modified" refers to a changed state or structure of a molecule of the disclosure. Molecules may be modified in many ways including chemically, structurally, and functionally. In one embodiment, the mRNA molecules of the present disclosure are modified by the introduction of non-natural nucleosides and/or nucleotides, e.g., as it relates to the natural ribonucleotides A, U, G, and C. Noncanonical nucleotides such as the cap structures are not considered "modified" although they may differ from the chemical structure of the A, C, G, U ribonucleotides.

The term "nucleotide" means natural bases (standard) and modified bases well known in the art. Such bases are generally located at the 1' position of a nucleotide sugar moiety. Nucleotides generally comprise a base, sugar, and a phosphate group. The nucleotides can be unmodified or modified at the sugar, phosphate, and/or base moiety, (also referred to interchangeably as nucleotide analogs, modified nucleotides, non-natural nucleotides, non-standard nucleotides and other; see, for example, Usman and McSwiggen, supra; Eckstein, et al., International PCT Publication No. WO 92/07065; Usman, et al., International PCT Publication No. WO 93/15187; Uhlman & Peyman, supra, all are hereby incorporated by reference herein). There are several examples of modified nucleic acid bases known in the art as summarized by Limbach, et al, Nucleic Acids Res. 22:2183, 1994. Some of the non-limiting examples of base modifications that can be introduced into nucleic acid molecules include: inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkyl cytidines (e.g., 5-methylcytidine), 5-alkyluridines (e.g., ribothymidine), 5-halouridine (e.g., 5-bromouridine) or 6-azapyrimidines or 6-alkylpyrimidines (e.g., 6-methyluridine), propyne, and others (Burgin, et al., Biochemistry 35:14090, 1996; Uhlman & Peyman, supra). By "modified bases" in this aspect is meant nucleotide bases other than adenine, guanine, cytosine, thymine and uracil at 1' position or their equivalents.

The term "open reading frame" or "ORF" to a nucleic acid sequence (DNA or RNA) which is capable of encoding a polypeptide of interest. ORFs often begin with the start codon ATG, and end with a nonsense or termination codon or signal.

The term "RNA" means a molecule comprising at least one ribonucleotide residue. By "ribonucleotide" is meant a nucleotide with a hydroxyl group at the 2' position of a β-D-ribo-furanose moiety. The terms includes double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution, and/or alteration of one or more nucleotides. Such alterations can include addition of non-nucleotide material, such as to the end(s) of an interfering RNA or internally, for example at one or more nucleotides of the RNA. Nucleotides in the RNA molecules of the instant disclosure can also comprise non-standard nucleotides, such as non-naturally occurring nucleotides or chemically synthesized nucleotides or deoxynucleotides. These altered RNAs can be referred to as analogs or analogs of naturally-occurring RNA. As used herein, the terms "ribonucleic acid" and "RNA" refer to a molecule containing at least one ribonucleotide residue, including siRNA, antisense RNA, single stranded RNA, microRNA, mRNA, noncoding RNA, and multivalent RNA.

The term "targeted cells" refers to any one or more cells of interest. The cells may be found in vitro, in vivo, in situ or in the tissue or organ of an organism. The organism may be an animal, preferably a mammal, more preferably a human and most preferably a patient.

The term "therapeutic agent" refers to any agent that, when administered to a subject, has a therapeutic, diagnostic, and/or prophylactic effect and/or elicits a desired biological and/or pharmacological effect.

The term "monomer" refers to a single unit, e.g., a single nucleic acid, which may be joined with another molecule of the same or different type to form an oligomer. In some embodiments, a monomer may be an unlocked nucleic acid, i.e., a UNA monomer.

The term "neutral lipid" means a lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

The term "non-cationic lipid" means an amphipathic lipid or a neutral lipid or anionic lipid and is described herein.

The term "oligomer" may be used interchangeably with "polynucleotide" and refers to a molecule comprising at least two monomers and includes oligonucleotides such as DNAs and RNAs. In the case of oligomers containing RNA monomers and/or unlocked nucleic acid (UNA) monomers, the oligomers of the present disclosure may contain sequences in addition to the coding sequence (CDS). These additional sequences may be untranslated sequences, i.e., sequences which are not converted to protein by a host cell. These untranslated sequences can include a 5' cap, a 5' untranslated region (5' UTR), a 3' untranslated region (3' UTR), and a tail region, e.g., a poly-A tail region. As described in further detail herein, any of these untranslated sequences may contain one or more UNA monomers—these UNA monomers are not capable of being translated by a host cell's machinery. In the context of the present disclosure, a "mRNA sequence", a "mRNA sequence", "translatable polynucleotide", or "translatable compound" refers to a sequence that comprises a region, e.g. , the coding region of an RNA, that is capable of being converted to a protein or a fragment thereof.

The term "translatable" may be used interchangeably with the term "expressible" and refers to the ability of polynucleotide, or a portion thereof, to be converted to a polypeptide by a host cell. As is understood in the art, translation is the process in which ribosomes in a cell's cytoplasm create polypeptides. In translation, messenger RNA (mRNA) is decoded by tRNAs in a ribosome complex to produce a specific amino acid chain, or polypeptide. Furthermore, the term "translatable" when used in this specification in reference to an oligomer, means that at least a portion of the oligomer, e.g., the coding region of an oligomer sequence (also known as the coding sequence or CDS), is capable of being converted to a protein or a fragment thereof.

The term "translation efficiency" refers to a measure of the production of a protein or polypeptide by translation of an mRNA sequence in vitro or in vivo. [0080] This disclosure provides a range of mRNA sequence molecules, which can contain one or more UNA monomers, and a number of nucleic acid monomers, wherein the mRNA sequence can be expressible to provide a polypeptide or protein.

Therapeutically effective outcome: As used herein, the term "therapeutically effective outcome" means an outcome that is sufficient in a subject suffering from or susceptible to an infection, disease, disorder, and/or condition, to treat, improve symptoms of, diagnose, prevent, and/or delay the onset of the infection, disease, disorder, and/or condition.

EXAMPLES

Additional embodiments of the present disclosure are illustrated in further detail in the following examples, which are not in any way intended to limit the scope of the claims.

Example 1: Large RNA Encapsulated Lipid Nanoparticle Manufacture

RNA and Lipid Excipients Dissolution

This example outlines some general conditions used for LNP encapsulated large RNA production. The lipid excipients (Ionizable cationic lipid/cationic lipid: phosphate lipid: cholesterol: PEG-lipid) are weighed and dissolved in 200 proof ethanol (at a molar ratio of 50:X:48.5-X:1.5, X=7, 10 or 13) at 40° C. until complete dissolution, with the dissolution time not exceeding four hours. After visible dissolution, the temperature of solution is equilibrated to room temperature followed by filtration of the solution through a 0.2 μm polyethersulfone (PES) filter into a jacketed glass or stainless-steel vessel. The nominal lipid concentration at this stage is 5-125 mg/mL.

The RNA is diluted in 5 mM citrate pH 4.0 buffer containing 0-300mM NaCl. The solution is then filtered through a 0.2 μm PES. The concentration of large RNA at this stage is about 0.096-0.765 mg/mL.

Nanoparticle Formation by a T Shape Stainless-Steel Mixing Module

Large RNA encapsulated lipid nanoparticles are formed by mixing the ethanolic solution of lipids with the aqueous solution of RNA at a controlled rate via a T-shaped stainless-steel mixing module ("T-Module"). The mixing comprises flowing the ethanol solution and the aqueous solution into the mixing module consisting of the 2nd tube perpendicularly joined to the 1st tube. An output solution comprising a mixture of the two solutions is produced flowing in the direction of the original RNA stream.

Total lipid to mRNA weight ratio is set to be about 35.88:1, however this weight ratio can vary depending on the exact size fo the large RNA being used and the lipid composition desired. A person of skill in the art will appreciate that the processes described herein are applicable to lipid compositions comprising any suitable combination of lipids in any suitable molar ratio and weight ration to the RNA. The rate of addition for each solution is controlled using a high-pressure piston pump (Knauer) with the lipid and mRNA solutions being added at a flow rate of 30-75 and 90-225 mL/min, respectively. The two streams converge in a stainless-steel mixing module at a total flow rate of 120-300 mL/min. Peek tubing are used for the high-pressure piston pump with 0.03-0.08 inch ID for RNA stream and 0.01-0.03 inch ID for lipid stream.

Nanoparticle Formation a Multi-Inlet Vortex Mixer

Large RNA encapsulated lipid nanoparticles are formed by mixing the ethanolic solution of lipids with the aqueous solution of RNA at a controlled rate via a multi-inlet vortex mixer (MIVM, Holland).

Total lipid to mRNA weigh ratio is 35.88:1. The rate of addition for each solution is controlled using an HPLC pump with the lipid and mRNA solutions being added at a flow rate of 20-50 mL/min per stream, respectively. The four streams converge in a stainless-steel mixing module at a total flow rate of 80-200 mL/min. Peek tubing are used for the high-pressure piston pump with 0.02-0.8 inch ID for RNA stream and 0.01-0.03 inch for lipid stream.

Nanoparticle Stablization by Stepwise Dilutions

The nanoparticles thus formed are stabilized by sequential in-line dilutions with buffers: first with 45 mM phosphate pH 6.5 buffer fed at a flow rate of 80-600 mL/min, followed by 50 mM HEPES or Tris, 50 mM NaCl, 9% (w/v) sucrose pH 8.0 buffer fed at a flow rate of 240-2700 mL/min.

Concentration and Buffer Exchange

The diluted nanoparticle formulation obtained as described above is concentrated and diafiltered against 50 mM HEPES/20mM Tris, 50 mM NaCl, 9% (w/v) sucrose pH 8.0 buffer by tangential flow filtration using modified PES hollow-fiber membranes with a 100 kDa MWCO. This process step ensures ethanol removal and buffer exchange. The temperature of the formulation during concentration and diafiltration is maintained at 16 to 25° C. Once ethanol removal is confirmed by Alco-Screen Alcohol Test Strips analysis, the concentrated solution is then filtered through a 0.2 µm PES filter into a glass bottle to remove potential larger particulates and microbiological contaminants. A sample of this filtered bulk product is collected for in-process RNA concentration analysis. The bulk product is stored at 2 to 8° C. until concentration adjustment.

Concentration Adjustment, Filling and Freezing

The concentration of RNA in the formulation is adjusted to the target concentration of 0.2 mg/mL by the addition of 50 mM HEPES/20 mM Tris, 50 mM NaCl, 9% (w/v) sucrose pH 8.0 buffer containing glycerol such that final concentration of glycerol in the buffer is 6.3% (w/v).

Following concentration adjustment, the adjusted bulk product is filtered through a 0.2 PES sterilizing-grade filter into a sterile collection vessel.

The product is aseptically filled to a fill volume of 1 mL (with a 0.2 mL overfill) in 2-mL Type I borosilicate glass vials, stoppered and capped. All vials are frozen at a controlled rate of 0.5° C. per minute to ≤−55° C. using a freezer drier or frozen directly at −70° C. The vials are stored in a freezer maintained at −70±10° C.

Concentration Adjustment, LYO Excipient Addition, Filling and Lyophilization The concentration of RNA in the formulation is adjusted to the target concentration of 0.1-0.2 mg/mL by the addition of 50 mM HEPES/20mM Tris, 50 mM NaCl, 9% (w/v) sucrose pH 8.0 buffer containing proper LYO excipients, and then can be stored at 2-8° C., −20° C. or −70 ±10° C. prior to lyophilization process or directly lyophilized.

Dynamic Light Scattering

The average particle size (z) and polydispersity index (PDI) of lipid nanoparticle formulations used in the Examples was measured by dynamic light scattering on a Malvern Zetasizer Nano ZS (United Kingdom).

RiboGreen Assay

The encapsulation efficiency of the lipid nanoparticle formulations was characterized using the RiboGreen fluorometric assay. RiboGreen is a proprietary fluorescent dye (Molecular Probes/Invitrogen a division of Life Technologies, now part of Thermo Fisher Scientific of Eugene, Oreg., United States) that is used in the detection and quantification of nucleic acids, including both RNA and DNA. In its free form, RiboGreen exhibits little fluorescence and possesses a negligible absorbance signature. When bound to nucleic acids, the dye fluoresces with an intensity that is several orders of magnitude greater than the unbound form. The fluorescence can be then be detected by a sensor (fluorimeter) and the nucleic acid can be quantified.

Acceptable LNP Physicochemical Characteristics

Further experiments were conducted as described in the examples below to evaluate the effects of various reagents, process parameters and appraturus configurations on the quality of LNP-encapsulated large RNA formulations. The quality of these formulations was assessed by analyzing the formulations for acceptable particle size (Z or Z-average), polydispersity (PDI) and encapsulation efficiency (% Encap). The various compositions tested were screened as to whether a threshold of properties was met including acceptable particle size (less than 150 nm, but most preferred is less than 120 nm), PDI (<0.2), and high encapsulation efficiency (>85%).

Example 2: LNP Comprising Large RNA-Initial Study

In an initial run, a Precision Nano Assembler (A benchtop formulation system, Precision Nanosystems, Inc., Vancouver, BC, Canada) was used to generate LNPs. The composition included a cationic lipid: DSPC: cholesterol: PEG-lipid at a molar ratio of 50:7:41.5:1.5. The mRNA was diluted in 5 mM pH 4.0 citrate buffer. The total lipid: RNA weight ratio was 35.2, and the total flow rate of both streams was 12 mL/min with a 1:3 EtOH to water ratio. Dilution, purification and concentration steps are as described in example 1, $1^{st}$ dilution ratio was 1:2 and $2^{nd}$ dilution ratio was 1:3. Initial results comparing a typical small and large nucleotide sequence are shown below in Table 1.

TABLE 1

| RNA | In-process | | |
|---|---|---|---|
| | Diameter (nm) | PDI | % Encap |
| Small mRNA (construct mARM2016, 1328 nt) | 74.8 | 0.053 | 94.9 |
| Luciferace self-replicating RNA (construct pARM2807, 9693 nt) | 93.99 | 0.358 | 88 |

As seen in Table 1, using the same process, encapsulation of the larger RNA resulted in a larger particle size, with higher polydispersity (PDI) and lower percentage of encapsulation efficiency (% encap).

Example 3: Effect of Salt Addition

In this Example, improved quality was observed for large RNA encapsulated lipid nanoparticles with the use of NaCl in citrate buffer. The composition, formulation module and mRNA were the same as described in Example 2. The results are summarized in Table 2 below.

In the table below, "[Lipid IP] mM" is the total lipid in-process concentration aftering mixing two streams without dilutions.

TABLE 2

| | Citrate Buffer | | Bulk | | | |
|---|---|---|---|---|---|---|
| [Lipid IP] mM | [Citrate] mM | pH | NaCl (mM) | Z-Ave (nm) | PDI | % Encap |
| 4 | 5 | 3.5 | 10 | 75 | 0.2 | 87 |
| 4 | 5 | 3.5 | 20 | 61 | 0.11 | 86 |
| 4 | 5 | 3.5 | 30 | 61 | 0.13 | 82 |
| 4 | 5 | 3.5 | 50 | 61 | 0.1 | 78 |
| 4 | 5 | 3.5 | 100 | 65 | 0.1 | 72 |
| 4 | 5 | 4 | 0 | 95 | 0.25 | 91 |
| 4 | 5 | 4 | 10 | 82 | 0.23 | 89 |
| 4 | 5 | 4 | 20 | 66 | 0.14 | 82 |

With these process improvements, pH 4.0 citrate buffer with 10 mM NaCl was chosen for further development because the pH 4.0 buffer also maintained better mRNA purity and integrity.

The effect of salt addition in citrate buffer worked across formulation compositions and different large self-replicating RNAs. It was also found that this buffer composition was easy to transfer to a medium scale formulation system including with the use of a multi-inlet vortex mixer. However, the buffer composition was not yet amenable to a large scale formulation system, such as those using a T-shaped mixing module. These further results are summarized below in Tables 3-5.

For formulations using a multi-inlet vortex mixer in this example, the four streams converge in a stainless-steel mixing module at a total flow rate of 120 mL/min as described in Example 1, with a lipids:RNA flow rate ratio ofs 1:3. Peek tubing were used for the high-pressure piston pump with 0.03 inch ID for RNA stream and 0.01 inch ID for lipid stream. The dilution ratio was 1:2 and 1:3, and purification and concentration steps were as described in Example 1.

For formulations using a scalable T-Module in this example, the two streams converge in the stainless-steel mixing module at a total flow rate of 300 mL/min as described in Example 1, with a lipids:RNA flow rate ratio of 1:3. Peek tubing was used for the high-pressure piston pump with 0.03 inch ID for the RNA stream and 0.01 inch ID for the lipid stream. Purification and concentration steps were conducted as described in Example 1.

TABLE 3

| Module Description | Lipid Comp. Cationic lipid: DSPC: CHOL: PEG-Lipid (molar ratio) | RNA | Z-ave (nm) | PDI | % Encap | Batch size |
|---|---|---|---|---|---|---|
| Medium scale, multi-inlet vortex mixer | 50:7:41.5:1.5 | Luciferace self-replicating RNA (construct no. pARM2807, 9693 nt) | 64.22 | 0.077 | 90.1 | 1.5 mg |
| | 50:10:38.5:1.5 | | 62.22 | 0.078 | 89.6 | |
| | 50:13:35.5:1.5 | | 62.97 | 0.078 | 89.8 | |

TABLE 4

| Module Description | Lipid Comp. Cationic lipid: DSPC:CHOL: PEG-Lipid (molar ratio) | RNA | Z-ave (nm) | PDI | % Encap | Batch size |
|---|---|---|---|---|---|---|
| Medium scale, multi-inlet vortex mixer | 50:10:38.5:1.5 | self-replicating RNA, 11,665 nt | 66.52 | 0.180 | 95.9 | 1.5 mg |
| | 50:13:35.5:1.5 | | 65.85 | 0.095 | 94.7 | |

TABLE 5

| Module Description | Lipid Comp. Cationic lipid: DSPC:CHOL: PEG-Lipid (molar ratio) | RNA | Z-ave (nm) | PDI | % Encap | Batch size |
|---|---|---|---|---|---|---|
| T-Module | 50:7:41.5:1.5 | Luciferace self-replicating RNA, pARM2807, 9693nt | 95.35 | 0.236 | 90.3 | 3 mg |
| | 50:10:38.5:1.5 | | 91.48 | 0.238 | 89.8 | |
| | 50:13:35.5:1.5 | | 92.11 | 0.231 | 88.1 | |

Example 4: Effffect of Salt Addition and pH of the $1^{st}$ Dilution Buffer

To improve the process, evaluation of salt addition and pH of the $1s^t$ dilution buffer (45 mM phosphate buffer) was conducted. Formulation composition and process was as described in Example 2 using a Precision Nano Assembler.

As shown in Table 6, NaCl addition in phosphate buffer did not further improve the LNP quality, resulting a large particle size, with higher polydispersity (PDI) and lower percentage of encapsulation efficiency (% encap).

TABLE 6

| [Lipid IP] | Citrate | | Phosphate Buffer | | Bulk | | |
|---|---|---|---|---|---|---|---|
| | [Citrate] | pH | NaCl (mM) | pH | PS | PDI | % Encap |
| 4 | 5 | 3.5 | 0 | 6.0 | 78.8 | 0.221 | 90.2 |
| 4 | 5 | 3.5 | 25 | 6.0 | 86.7 | 0.246 | 90.1 |
| 4 | 5 | 3.5 | 50 | 6.0 | 88.7 | 0.254 | 86.6 |
| 4 | 5 | 3.5 | 100 | 6.0 | 89.9 | 0.272 | 88.2 |

Further evaluation, including pH change of phosphate buffer, was conducted. A pH of 6.5 was selected based on the pKa of the ionizable cationic lipid in this formulation (~6.4). This change dramatically improved encapsulation efficiency of the lipid nanoparticles as shown in Table 7. A composition of Ionizable Cationic Lipid: DSPC: CHOL: PEG-DMG2000=50:13:35.5:1.5 molar ratio was used in this formulation.

TABLE 7

| [Lipid IP] | Citrate | | Phosphate Buffer | | Bulk | | |
|---|---|---|---|---|---|---|---|
| | [Citrate] | pH | NaCl (mM) | pH | PS | PDI | % Encap |
| 4 | 5 | 4 | 10 | 6.5 | 71.03 | 0.202 | 95.8 |

Example 5: Effect of Flow Rate in MIVM and T-Module Systems

A composition of Ionizable Cationic Lipid: DSPC: CHOL: PEG-DMG2000=50:10:38.5:1.5 molar ratio with a total lipid: RNA weight ratio of about 35.78:1 was used in this example. Luciferace self-replicating RNA (construct no. pARM2807, 9693 nt) was used. The formulation process for the MIVM system and the T-Module system were as described in Example 3, respectively.

Surprisingly, a lower flow rate worked better for large RNA encapsulated formulations for both the MIVM system and the formulation-Module system. With the lower flow rate, particle size (Z-ave) and PDI were smaller, and % encap was higher. (Shown in Table 8 and Table 9). Striving to attain both acceptable manufacturing rate and acceptable LNP quality, 100 ml/min for the MIVM system and 160 ml/min for the T-Module system were chosen for further development.

TABLE 8

| Formulation system | Total flow rate (ml/min) | Bulk | | |
|---|---|---|---|---|
| | | PS | PDI | % Encap |
| MIVM | 100 | 73.33 | 0.117 | 94.4 |
| | 120 | 75.16 | 0.132 | 94.8 |
| | 160 | 82.13 | 0.152 | 93.4 |

TABLE 9

| Formulation system | Total flow rate (ml/min) | Bulk | | |
|---|---|---|---|---|
| | | PS | PDI | % Encap |
| ARC | 120 | 79.75 | 0.15 | 94.1 |
| | 160 | 82.21 | 0.161 | 95.4 |
| | 200 | 87.70 | 0.205 | 94.3 |
| | 333 | 103.3 | 0.242 | 91.9 |

The finding in this example was the opposite of what was observed for small RNA encapsulated lipid nanoparticle formulations as shown in Table 10. Higher flow rates provided smaller particle size and lower PDI for small RNA encapsulated lipid nanoparticles. For the process having the results for small RNA encapsulated LNPs in Table 10, a siRNA with 23 nt length was used.

TABLE 10

| RNA | Formulation system | Total flow rate (ml/min) | Bulk | | |
|---|---|---|---|---|---|
| | | | Z-Ave (nm) | PDI | % Encap |
| siRNA (23 nt) | T-Module | 100 | 106.9 | 0.087 | 99.1 |
| | | 200 | 75.7 | 0.080 | 99.4 |
| | | 300 | 71.2 | 0.066 | 99.3 |
| | | 333 | 69.7 | 0.063 | 99.5 |

Example 6: Large RNA Encapsulated Lipid Nanoparticle Manufacture in Scalable MIVM and Formulation-Module System With all the improvements mentioned in Examples 2-5, the formulation process for LNP encapsulated large RNA (Luciferace self-replicating RNA, pARM2807, 9693 nt; and another self-replicating RNA, 11,665 nt) across scalable formulation systems (MIVM and T-Module) was developed, and it is applicable to different compositions (Table 11). The formulation conditions and process in this example were as described in earlier examples, unless otherwise pointed out.

TABLE 11

| Module Description | Lipid Comp. Cationic lipid: DSPC:CHOL: PEG-Lipid (molar ratio) | RNA | Z-ave (nm) | PDI | % Encap | Batch Volume for 1 g RNA (L) |
|---|---|---|---|---|---|---|
| MIVM | 50:7:41.5:1.5 | Luciferace self-replicating RNA, pARM2807, 9693 nt | 75.02 | 0.163 | 93.3 | 167.5 |
|  | 50:10:38.5:1.5 |  | 74.54 | 0.18 | 93.1 |  |
|  | 50:13:35.5:1.5 |  | 78.34 | 0.184 | 91 |  |
| T-Module | 50:7:41.5:1.5 |  | 89.17 | 0.217 | 92 |  |
|  | 50:10:38.5:1.5 |  | 88.74 | 0.196 | 91.3 |  |
|  | 50:13:35.5:1.5 |  | 89.47 | 0.195 | 90.5 |  |

To meet manufacturing requirements, the possibility of an all-in-line set-up for continuous manufacturing was tested. Long tubing between 1st and 2nd dilutions was used to prolong the holding time between both dilutions. This was based on learnings from previous examples. As shown in Table 12, the quality of large RNA encapsulated LNP was not affected by an all-in-line set-up.

particle size, PDI and high % encap. But once a threshold was reached, higher NaCl concentrations did not need to be increased any further. A proper NaCl concentration in citrate buffer was needed for large RNA encapsulated lipid nanoparticle manufacture, and this was compatible with an all-in-line set-up, provided the possibility of continuous large-scale manufacture.

TABLE 12

| Module Description | Holding time between 1st and 2nd dilution | Lipid Comp. Cationic lipid:DSPC:CHOL: PEG-Lipid (molar ratio) | RNA | Z-ave (nm) | PDI | % Encap | Batch Volume for 1 g RNA(L) |
|---|---|---|---|---|---|---|---|
| MIVM | 20s | 50:10:38.5:1.5 | Luciferace self-replicating RNA, pARM2807, 9693 nt | 73.11 | 0.133 | 92.2 | 167.5 |
|  | 30s |  |  | 76.48 | 0.173 | 93.3 |  |

Example 7: Scaling-Up of Large RNA Encapsulated Lipid Nanoparticle Manufacturing Process by MIVM and T-Module Formulation System The formulation process described in Example 6 was shown to work well for large RNA encapsulated lipid nanoparticle manufacture, but the batch volume and manufacturing rate showed a need for further improvement. In embodiments in this example, multiple approaches were taken to achieve this goal.

All formulation compositions, conditions and process in this example were the same as Example 6, unless otherwise pointed out.

In-Process Concentration Increasing with NaCl Addition in Citrate Buffer

In this embodiment, in-process concentration was increased for scaling up purpose, and a relationship between the in-process concentration and NaCl concentration in citrate buffer was found (Shown in Table 13 and Table 14), this finding is across different manufacture modules. Higher NaCl concentration in citrate buffer was needed for higher in-process concentration formulation, and it provided small

TABLE 13

| Formulation process | [Lipid IP] | NaCal conc. In Citrate buffer (mM) | PS (nm) | PDI | % Encap | Batch Volume (L/g mRNA) |
|---|---|---|---|---|---|---|
| MIVM | 4 | 10 | 73.3 | 0.117 | 94.4 | 167.5 |
|  | 8 | 10 | 86.7 | 0.176 | 94.3 | 83.8 |
|  | 12 | 10 | 93.8 | 0.179 | 95.6 | 55.8 |
|  | 12 | 30 | 82.5 | 0.152 | 95.1 |  |
|  | 12 | 50 | 79.12 | 0.126 | 95.6 |  |
| MIVM, all-in-line, 30 sec holding time | 12 | 50 | 81.01 | 0.148 | 95.7 |  |

TABLE 14

| Formulation process | [Lipid IP] | NaCal conc. In Citrate buffer (mM) | PS (nm) | PDI | % Encap | Batch Volume (L/g mRNA) |
|---|---|---|---|---|---|---|
| T-Module | 16 | 50 | 83.91 | 0.156 | 96.4 | 41.9 |
|  | 12 | 50 | 71.35 | 0.125 | 96 | 55.8 |
| T-Module all-in-line | 12 | 50 | 71.59 | 0.094 | 96.1 |  |

Dilution Ratio Reduction for Scaling-Up

To further reduce the batch volume, the dilution ratio reduction was evaluated. As described in Example 1, a 2-step dilution was needed for large RNA encapsulated lipid nanoparticle manufacture process. In all the previous examples, 1:2 dilution with 45 mM phosphate buffer and 1:3 dilution with pH 8.0, 50 mM HEPES buffer containing 50 mM NaCl and 9% sucrose was conducted. In this embodiment, a lower dilution ratio was tested in a range maintaining the proper ethanol concentration and pH in the diluted formulation. 8 hours holding time prior to purification process (TFF) was also tested to ensure the stability of the formulation during large scale manufacture purification process (Table 15).

As shown in Table 15, the physicochemical properties of the formulation were not affected by reducing the dilution ratios of the process. After 8 hours holding, physicochemical properties of the formulation were also maintained. In this example, mRNA purity and integrity was also tested by Fragment analyzer to ensure the mRNA potency can be maintained during manufacture. The mRNA purity and integrity are reported relative to the purity and integrity of the mRNA prior to encapsulation.

At 12 mM lipid [IP], with 50 mM NaCl in 5 mM pH 4.0 citrate buffer, 1:1.5 phosphate dilution followed by 1:2.5 HEPES buffer dilution, the LNP had good quality and was stable in physicochemical properties and mRNA purity for at least 8 hours before beginning the purification process (TFF), which ensured the LNP stability during manufacturing process.

TABLE 15

| 1st Dilut. | 2nd Dilut. | Process Description | Holding time before TFF (hr) | Diameter (nm) | PDI | % Encap | mRNA Purity (%) | Batch Volume (L/g mRNA) |
|---|---|---|---|---|---|---|---|---|
| 1:1 | 1:2.5 | T-Module, 160 | 0 | 67.97 | 0.105 | 92 | 90.8 | 32.6 |
| 1:1.5 | 1:2 | mL/min, 12 mM | 0 | 71.46 | 0.114 | 94 | 89.2 | 34.9 |
| 1:1.5 | 1:2.5 | lipid IP, 5 mM | 0 | 70.91 | 0.069 | 95 | 87.7 | 40.7 |
| 1:2 | 1:2 | citrate pH 4.0 + 50 | 0 | 70.81 | 0.085 | 90 | 90.8 | 42 |
| 1:1.5 | 1:2.5 | mM NaCl; All | 0 | 76.75 | 0.111 | 96 | 92.3 | 40.7 |
| 1:1.5 | 1:2.5 | In-line (30 sec hold). | 8 | 77.65 | 0.108 | 95 | 96.9 | |

Example 8: Tubing Configuration and Backpressure for Large RNA Encapsulated Lipid Nanoparticle Manufacture For smaller RNA encapsulated lipid nanoparticle manufacture, to bring up the back pressure for the high-pressure piston pump used in the module, smaller tubing (0.01, 0.02 inch ID) was often used. To avoid pulsation of the RNA stream, a clamp on the tubing which connects the peek tubing and the mixing module was often used. This example showed a point of failure using the manufacture process developed in Example 7 but using 0.02 inch ID peek tubing for RNA stream and a clamp on the tubing between peek tubing and T-Module. Afterwards, an evaluation of the effect of tubing configuration and backpressure was conducted. (Table 16). In this example, all formulation composition, conditions and process were the same as Example 7, unless mentioned otherwise.

TABLE 16

| Pump Tubing (ID in inch and length in cm) | Pump Back Pressures | Z-Ave | PDI | % Encap |
|---|---|---|---|---|
| Original development set-up: RNA 0.03 (27 cm); Lipid 0.03 (30 cm) | RNA 18 psi; Lipid 55-60 psi | 80.96 | 0.153 | 94.1 |
| Manufacture set-up 1: RNA 0.02 (50 cm); Lipid: 0.01 (30 cm) | RNA 250 psi; Lipid 395-405 psi | 99.80 | 0.247 | 81.4 |
| Investigation set-up: RNA 0.03 (50 cm); Lipid: 0.01 (30 cm) | RNA 19-21 psi; Lipid 395-405 psi | 82.13 | 0.152 | 95.2 |

As shown in Table 16, the particle size and PDI was surprisingly higher while the % encap was surprisingly low when using a 0.02 inch peek tubing for RNA stream and 0.01 inch tubing for lipid stream during manufacture. In order to understand which line made the difference, an investigation set-up: RNA 0.03 (50 cm); Lipid: 0.01 (30 cm) was used and produced good quality LNPs. Comparing these 3 set-ups, the results clearly showed that the RNA stream tubing had an important effect on LNP quality. However, it was not known whether the tubing ID, the high pressure, or both were the cause.

Thus, a set of tests with different RNA stream tubing length and size was conducted (Table 17). The results showed that LNP qualities were affected when using 0.02 inch tubing, even for extremely short lengths.

TABLE 17

| Pump Tubing (ID in inch and length in cm) | Pump Back Pressures (psi) | Z-Ave | PDI | % Encap |
|---|---|---|---|---|
| RNA: 0.03 (27 cm); Lipid: 0.01 (30 cm) | RNA 19-21; Lipid 395-405 | 82.13 | 0.152 | 95.2 |
| RNA: 0.02 (40 cm); Lipid: 0.01 (30 cm) | RNA 152; LIPID 412 | 97.91 | 0.230 | 77.1 |
| RNA: 0.02 (25 cm); Lipid: 0.01 (30 cm) | RNA 104; LIPID 401 | 99.57 | 0.294 | 76.0 |
| RNA: 0.02 (10 cm); Lipid: 0.01 (30 cm) | RNA 61; LIPID 415 | 97.6 | 0.238 | 80.9 |
| RNA: 0.03 (27 cm) + 0.02 (5 cm); Lipid: 0.01-30 cm) | RNA 60; LIPID 396 | 95.1 | 0.194 | 88.5 |

Further investigation was done with results shown in Table 18. Removal of the clamp was good for the formulation. However, when using 0.03 inch ID tubing for both lines and long tubing in the RNA line (90 cm) to avoid pulsation, the results were not favorable. When an intermediate length tube was used (48 cm) with a clamp in the RNA line through the mixing module to maintain the backpressue while mixing in combination with smaller tubing for the lipid stream (0.01 inch ID) was good for the formulation. A pressure of about 70 psi was safe for the formulation.

TABLE 18

| Pump Tubing (ID in inch and length in cm) | Pump Back Pressures (psi) | Z-Ave | PDI | % Encap |
|---|---|---|---|---|
| RNA 0.03 (27 cm); Lipid 0.03 (30 cm) | RNA 30 psi; Lipid 53 psi | 68.69 | 0.138 | 98 |
| RNA 0.03 (90 cm) to increase the pressure and avoid pulsation; Lipid 0.03 (30 cm) | RNA 64 psi; Lipid 50 psi | 88.9 | 0.166 | 96.1 |
| RNA 0.03 (48 cm) + clamp; Lipid 0.01 (30 cm) to avoid pulsation for both streams | RNA 68 psi; Lipid 487 psi | 75.37 | 0.158 | 95.6 |

Example 9: Possible Mechanism of the Findings of Examples 1-8

With all the findings above, a possible mechanism is discussed in this example. Since all these findings only apply to large RNA (~6000-13000 nt), and large RNA encapsulated lipid nanoparticle quality was affected by RNA concentration in citrate buffer, NaCl concentration in citrate buffer, tubing size of RNA+citrate stream and flow rate of the RNA stream. A hypothesis is that the large RNA (~6000-13000 nt) is more sensitive to shear stress and shear rate.

Such findings can be explained using the formulas below:
Shear rate:

$$\dot{\gamma} = \frac{4Q}{\pi r^3}$$

Volumetric flow rate Q; inner pipe radius r.

Shear stress: For a Newtonian fluid wall, shear stress ($\tau_W$) can be related to shear rate by $\tau_W = \dot{\gamma}_X \mu$, where $\mu$ is the dynamic viscosity of the fluid. Thus, shear stress will increase as either shear rate or dynamic viscosity increases. In turn, shear rate is inversely proportional to inner pipe radius while dynamic viscosity will be affected by buffer and fluid conditions as well as the RNA size.

Further dynamic viscosity of the fluid and calculation can be evaluated, as will be appreciated by those skilled in the art.

Example 10: Further Improvement and Scaling-Up of the Large RNA Encapsulated Lipid Nanoparticle Manufacture Process In this example, all formulation conditions and process were the same as Example 7, ID of peek tubing size of RNA stream was 0.04 inch in this example, unless pointed out.

With the learnings from Examples 1-9, further improvement was achieved by design. In this achievement, batch volume was dramatically decreased, and the manufacture rate was greatly improved, large RNA encapsulated lipid nanoparticle quality was improved. Applying the clamp only on the RNA stream to avoid pulsation can be used when the total flow rate is high enough (300 ml/min). Pressure on RNA stream at ~80 psi was shown to be a safe condition, but higher than 100 psi will adversely affect the lipid nanoparticle quality.

Table 19 and Table 20 showed the significant improvement of the large RNA encapsulated lipid nanoparticle manufacture process by the design based on the learning through Examples 1-9. LNP quality was well maintained, batch volume was dramatically decreased by the combination of increased flow rate, NaCl concentration in citrate buffer and RNA stream tubing ID. With 300 ml/min as total flow rate, the clamp on the RNA stream was not required.

TABLE 19

| In-process concentration | Total flow rate (ml/min) | NaCl in citrate buffer (mM) | RNA stream tubing ID (in) | Backpressue on T-Module by clamp | Z-ave (nm) | PDI | % Encap |
|---|---|---|---|---|---|---|---|
| 12 | 160 | 50 | 0.03 | Yes | 78.25 | 0.141 | 95.7 |
| 12 | 240 | 50 | 0.04 | Yes | 76.72 | 0.138 | 95.8 |
| 16 | 240 | 50 | 0.04 | Yes | 86.72 | 0.2 | 97.9 |
| 16 | 240 | 75 | 0.04 | Yes | 70.74 | 0.122 | 98.4 |
| 16 | 240 | 100 | 0.04 | Yes | 68.9 | 0.125 | 98.2 |
| 20 | 300 | 100 | 0.04 | Yes | 76.37 | 0.139 | 98.9 |
| 20 | 300 | 150 | 0.04 | Yes | 72.02 | 0.113 | 98 |
| 20 | 300 | 150 | 0.04 | No | 70.67 | 0.113 | 98.7 |
| 20 | 240 | 100 | 0.04 | Yes | 70.55 | 0.116 | 98.5 |
| 24 | 300 | 150 | 0.04 | Yes | 78.34 | 0.134 | 98.6 |
| 24 | 300 | 100 | 0.04 | Yes | 80.87 | 0.157 | 97.9 |
| 24 | 240 | 100 | 0.04 | Yes | 78.61 | 0.132 | 98.5 |
| 24 | 240 | 150 | 0.04 | Yes | 76.78 | 0.124 | 98.7 |
| 24 | 300 | 200 | 0.04 | Yes | 76.11 | 0.125 | 98.7 |

TABLE 20

| Lipid [IP] | NaCl concentration in citrate buffer | Dilution ratios | 1 gram Batch Size (L) | Z-ave (nm) | PDI | Purity by fragment (% relative to initial RNA stock) | % Encap |
|---|---|---|---|---|---|---|---|
| 20 mM | 150 mM NaCl | 1:1.5; 1:1.5 | 17.5 | 75.12 | 0.17 | 82.9 | 98.5 |
| 24 mM | 150 mM NaCl | 1:1.5; 1:1.5 | 14.5 | 87.89 | 0.19 | 97.1 | 97.7 |
| 24 mM | 200 mM NaCl | 1:1.5; 1.5 | 14.5 | 76.78 | 0.13 | 98.5 | 98.7 |
| 28 mM | 200 mM NaCl | 1:1.5; 1.5 | 12.5 | 82.40 | 0.13 | 94.1 | 98.1 |
| 28 mM | 250 mM NaCl | 1:1.5; 1.5 | 12.5 | 80.21 | 0.10 | 92.6 | 98.2 |
| 32 mM | 250 mM NaCl | 1:1.5; 1.5 | 10.9 | 88.49 | 0.107 | 86.5 | 97.3 |
| 32 mM | 300 mM NaCl | 1:1.5; 1.5 | 10.9 | 89.55 | 0.13 | 82.4 | 97.4 |

Example 11: Further Improvement and Scaling-Up of the Large RNA Encapsulated Lipid Nanoparticle Manufacturing Process in Another Buffer System The production fo lyophilized RNA encapsulated LNPs is important for providing drug products with stability in certain environments. One part of the lyophilization process involves preparing a suspension of LNPs in the proper matrix. U.S. application Ser. No. 17/402,077 describes methods of lyophilizing lipid nanoparticle encapsulated RNAs and is incorporated herein by reference. To develop a lyophilized large RNA encapsulated lipid nanoparticle drug product, a large RNA encapsulated lipid nanoparticle manufacturing process in Tris buffer system was developed based on the learnings from Examples 1-10. The formulation conditions and process set-up were the same as Example 10 with all-in-line set-up at a holding time between 15 seconds to 25 seconds. The only differences were that the 2nd dilution buffer was pH 8.0, 50 mM Tris containing 50 mM NaCl and 9% sucrose, and the diafiltration buffer was pH 8.0, 20 mM Tris containing 50 mM NaCl and 9% sucrose. (Table 21)

All learnings from Examples 1-10 were applicable for Tris buffer system formulation.

Example 12: EDTA Eddition During Dilution and Final Confirmation of the Large RNA Encapsulated Lipid Nanoparticle Manufacture Process In this example, all formulation conditions and process set-up were the same as Example 11, unless stated otherwise. The effect of EDTA addition during the second dilution and removing during diafiltration were tested in this example, and the final highly scaled up manufacturing process was confirmed as 28 mM lipid IP concentration with holding time between 1st and 2nd dilution as 20 seconds, dilution ratio as 1:1.5, 1:2, with or without EDTA addition to produce high quality large RNA encapsulated lipid nanoparticles. (Table 22)

TABLE 21

| Holding time prior to TFF | Lipid [IP] | NaCl concentration in citrate buffer | Dilution ratios | 1 gram Batch Size (L) | Z-ave | PDI | Purity by fragment (% relative to initial RNA stock) | % Encap |
|---|---|---|---|---|---|---|---|---|
| T-0 | 20 mM | 150 mM | 1:1.5; 1:1.5 | 17.2 | 72.43 | 0.143 | 89.2 | 98 |
| T = 8 | | | | | 71.99 | 0.16 | 86.3 | 96.9 |
| T-0 | 24 mM | 200 mM | 1:1.5; 1:1.5 | 14.5 | 75 | 0.195 | 86.5 | 97.2 |
| T = 8 | | | | | 74.1 | 0.122 | 89.0 | 97.5 |
| T-0 | 28 mM | 200 mM | 1:1.5; 1:1.5 | 12.5 | 78.44 | 0.13 | 93.2 | 98.4 |
| T = 8 | | | | | 79.55 | 0.122 | 89.0 | 97.6 |
| T-0 | 32 mM | 250 mM | 1:1.5; 1:1.5 | 10.9 | 82.62 | 0.115 | 89.2 | 97.5 |
| T = 8 | | | | | 83.51 | 0.09 | 86.3 | 97.6 |
| T-0 | 32 mM | 250 mM | 1:1.5; 1:2 | 13.08 | 85.95 | 0.1 | 93.2 | 98 |
| T = 8 | | | | | 87.68 | 0.129 | 86.3 | 97.4 |

TABLE 22

| Hold Time | IP [mM] | NaCl in Citrate | Holding btw 1st and 2nd dil | Dil Ratios | EDTA addition? | Diameter (nm) | PDI | % Encap |
|---|---|---|---|---|---|---|---|---|
| T-0 | 28 mM | 200 mM NaCl | 15 sec | 1:1.5; 1:1.5 | No | 81.6 | 0.121 | 98.2 |
| T = 8 | 28 mM | 200 mM NaCl | | | | 79.44 | 0.116 | 98.2 |
| T-0 | 28 mM | 200 mM NaCl | 25 sec | | | 81.66 | 0.094 | 98.5 |
| T = 8 | 28 mM | 200 mM NaCl | | | | 79.39 | 0.149 | 98.8 |
| T-0 | 28 mM | 200 mM NaCl | 15 sec | 1:1.5; 1:2 | | 82.19 | 0.163 | 98.1 |
| T = 8 | 28 mM | 200 mM NaCl | | | | 77.5 | 0.125 | 98.3 |
| T-0 | 28 mM | 200 mM NaCl | 15 sec | 1:1.5; 1:2.5 | | 84.21 | 0.155 | 98 |
| T = 8 | 28 mM | 200 mM NaCl | | | | 79.34 | 0.128 | 98.5 |
| T-0 | 28 mM | 200 mM NaCl | 15 sec | 1:1.5; 1:1.5 | Yes | 78.38 | 0.13 | 98.4 |
| T = 8 | 28 mM | 200 mM NaCl | | | | 79.37 | 0.125 | 98.7 |
| T-0 | 28 mM | 200 mM NaCl | 25 sec | | | 78.98 | 0.09 | 98.4 |
| T = 8 | 28 mM | 200 mM NaCl | | | | 79.39 | 0.151 | 98.8 |

Figure 4:
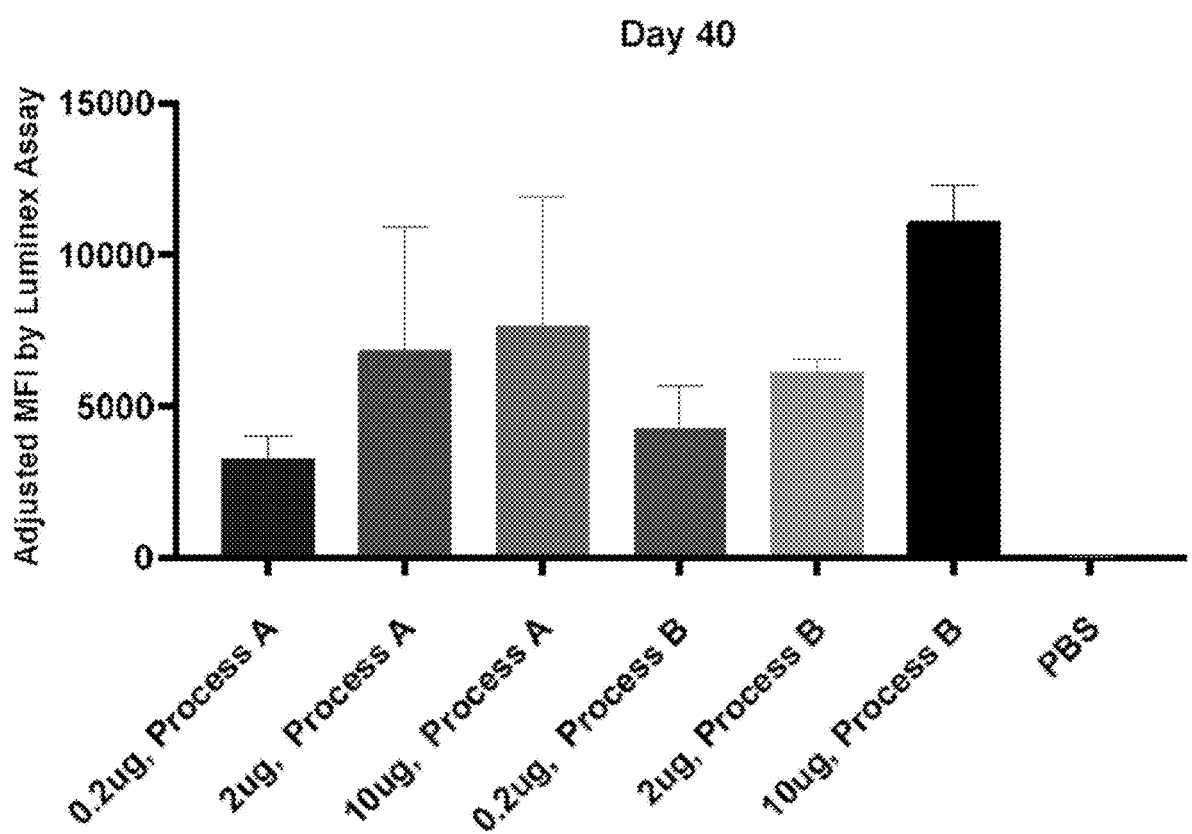
FIG. 4 shows adjusted mean-fluorescent intensity (MFI) for varying dose levels of lipid nanoparticle formulations described in Example 13, corresponding to anti-COVID19 Spike Protein antibody levels developed in response to the lipid nanoparticle administration to mice.

Example 13: Effect of the Large RNA Encapsulated Lipid Nanoparticle Manufacturing Process Improvement on In Vivo Efficacy In this embodiment, FIG. 4 showed that not only the large RNA encapsulated lipid nanoparticle physicochemical properties were well maintained and improved by using the scaled-up processes described herein, but also the in vivo efficacy was maintained and improved. Table 23 showed the manufacture difference of these two processes, other than what is described in Table 23, all formulation conditions and other process set-up were the same as Example 7.

In this embodiment, 50 µl of the large RNA encapsulated lipid nanoparticles with RNA encoding COVID spike protein were injected on both legs of Balb/c mice intramuscularly to 2. A method of producing a lipid-encapsulated RNA nanoparticle, comprising the steps
   a) flowing an aqueous solution comprising an RNA through a $1^{st}$ tube having a first inner diameter (ID); wherein the RNA comprises from about 6,000 to about 13,000 nucleotides;
   b) flowing an ethanol solution comprising lipids through a $2^{nd}$ tube having a second inner diameter (ID), at a flow rate of about 0.2 to about 1 times a flow rate of the aqueous solution through the $1^{st}$ tube, wherein the lipids comprise a cationic lipid; and
   c) mixing the ethanol solution with the aqueous solution; wherein the first ID and second ID and flow rates through the $1^{st}$ tube and $2^{nd}$ tube are selected to produce a shear force sufficiently low to preserve the integrity of the RNA;
      wherein the mixing produces an output solution flowing in the $1^{st}$ tube comprising a turbulent flow of the RNA and the lipids in between about 10% to 75% ethanol v/v; and
      wherein the lipid-encapsulated RNA nanoparticles have a bilayer structure.

3. The method of claim 1, wherein the mixing comprises flowing the ethanol solution and the aqueous solution into a mixing module consisting of the $2^{nd}$ tube perpendicularly joined to the $1^{st}$ tube.

4. The method of claim 1, wherein the mixing comprises flowing the ethanol solution and the aqueous solution into a multi-inlet vortex mixer.

5. The method of claim 1, wherein a concentration of RNA in the aqueous solution is in a range from about 85 micrograms/mL to about 2100 micrograms/mL.

6. The method of claim 1, wherein a concentration of lipid in the ethanol solution is in a range from about 5.0 mg/mL to about 125 mg/mL.

7. The method of claim 1, wherein the aqueous solution is pumped through the $1^{st}$ tube by a $1^{st}$ pump with a back pressure of not more than about 200 psi, and the ethanol solution is pumped through the $2^{nd}$ tube by a $2^{nd}$ pump.

8. The method of claim 1, wherein the $1^{st}$ tube has an ID in a range from about 0.02 inches to about 0.03 inches and the $2^{nd}$ tube has an ID in a range from about 0.01 inches to about 0.02 inches.

9. The method of claim 1, wherein the aqueous solution is pumped at a flow rate in a range from about 40 mL/min. to about 375 mL/min.

10. The method of claim 1, wherein the aqueous, ethanol, and output solutions are maintained in a temperature range from about 10° C. to about 25° C.

11. The method of claim 1, further comprising pumping a first dilution buffer and mixing the dilution buffer with the output solution by introducing the dilution buffer to the output solution to produce a first diluted output solution.

12. The method of claim 11, further comprising pumping a second dilution buffer into the first diluted output solution thereby forming a final diluted output solution, wherein there is a delay between pumping the first dilution buffer and second dilution buffer.

13. The method of claim 11, wherein the first dilution buffer comprises:
   a) a buffering agent having a pH from about 5.5 to about 7.0; and
   b) optionally a sodium chloride concentration up to about 100 mM; and the second dilution buffer comprises:
   a) a buffering agent having a pH between about 7.4 and 8.0; and
   b) optionally a sodium chloride concentration up to about 100 mM.

14. The method of claim 12, wherein the second buffer comprises sucrose up to about 15% w/v, an antioxidant up to about 0.5% w/v, up to 20 mM of a chelating agent, or any combination of the foregoing.

15. The method of claim 11, wherein the first diluted output solution comprises about 1.0% to about 10.0% ethanol.

16. The method of claim 11, wherein the first dilution buffer is pumped at a flow rate from about 80 mL/min. to about 900 mL/min and the second dilution buffer is pumped at a flow rate from about 240 mL/min to about 5400 mL/min.

17. The method of claim 1, wherein the lipid-encapsulated RNA nanoparticle has an average particle size in a range from about 50 nm to about 120 nm.

18. The method of claim 1, wherein the lipid portion of the lipid-encapsulated RNA nanoparticle further comprises one or more agents selected from the group consisting of a helper lipid, a cholesterol, and a PEG lipid conjugate.

19. The method of claim 1, wherein the RNA is self-replicating RNA.

20. The method of claim 1, further comprising lyophilizing the final diluted output solution.

* * * * *